US012565486B2

(12) United States Patent
Li et al.

(10) Patent No.: US 12,565,486 B2
(45) **Date of Patent: *Mar. 3, 2026**

(54) NON-PLATINUM METAL COMPLEXES FOR EXCIMER BASED SINGLE DOPANT WHITE ORGANIC LIGHT EMITTING DIODES

(71) Applicant: Arizona Board of Regents on behalf of Arizona State University, Scottsdale, AZ (US)

(72) Inventors: Jian Li, Tempe, AZ (US); Liang Huang, Mesa, AZ (US); Tyler Fleetham, Gilbert, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/758,770

(22) Filed: Jun. 28, 2024

(65) Prior Publication Data

US 2024/0368124 A1 Nov. 7, 2024

Related U.S. Application Data

(63) Continuation of application No. 17/019,817, filed on Sep. 14, 2020, now Pat. No. 12,043,611, which is a (Continued)

(51) Int. Cl.

*C07D 401/14* (2006.01)
*C07F 1/12* (2006.01)
*C07F 7/08* (2006.01)
*C07F 9/50* (2006.01)
*C07F 15/00* (2006.01)
(Continued)

(52) U.S. Cl.

CPC .............. *C07D 401/14* (2013.01); *C07F 1/12* (2013.01); *C07F 7/0803* (2013.01); *C07F 9/5045* (2013.01); *C07F 15/0033* (2013.01); *C07F 15/006* (2013.01); *C07F 15/0073* (2013.01); *C09K 11/06* (2013.01); *H10K 59/10* (2023.02); *H10K 85/341* (2023.02); *H10K 85/654* (2023.02); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1074* (2013.01); *C09K 2211/1096* (2013.01); *C09K 2211/18* (2013.01); *C09K 2211/185* (2013.01); *H10K 50/11* (2023.02); *H10K 85/324* (2023.02); *H10K 2101/10* (2023.02); *Y02E 10/549* (2013.01)

(58) Field of Classification Search

CPC .. H10K 85/371; H10K 85/342; H10K 85/341; H10K 85/346; C07F 15/006; C07F 1/12; C07F 15/0033; C07F 15/0073

See application file for complete search history.

(56) References Cited

U.S. PATENT DOCUMENTS 4,769,292 A 9/1988 Tang
5,451,674 A 9/1995 Silver
(Continued)

FOREIGN PATENT DOCUMENTS

CN 1680366 A 10/2005
CN 1777663 5/2006
(Continued)

OTHER PUBLICATIONS

IUPAC—Compendium of Chemical Terminology, Gold Book, p. 203 (2012) (Year: 2012).*
(Continued)

*Primary Examiner* — Alexander R Pagano
(74) *Attorney, Agent, or Firm* — Riverside Law LLP

(57) ABSTRACT

Complexes and devices, such as organic light emitting devices and full color displays, including a compound of the formula:

General Formula I

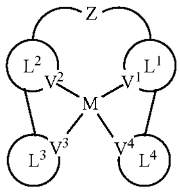

wherein:

M is $Pd^{2+}$, $Ir^{+}$, $Rh^{+}$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

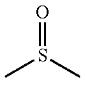 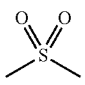 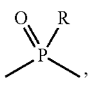 , or 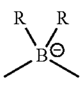 , where each R is independently substituted or unsubstituted $C_1$-$C_4$ alkyl or substituted or unsubstituted aryl.

14 Claims, 12 Drawing Sheets

Related U.S. Application Data continuation of application No. 15/503,690, filed as application No. PCT/US2015/045416 on Aug. 14, 2015, now Pat. No. 10,793,546.

(60) Provisional application No. 62/037,802, filed on Aug. 15, 2014.

(51) Int. Cl.

| | |
|---|---|
| ***C09K 11/06*** | (2006.01) |
| ***H10K 59/10*** | (2023.01) |
| ***H10K 85/30*** | (2023.01) |
| ***H10K 85/60*** | (2023.01) |
| *H10K 50/11* | (2023.01) |
| *H10K 101/10* | (2023.01) |

(56) References Cited

U.S. PATENT DOCUMENTS 5,641,878 A 6/1997 Dandliker
5,707,745 A 1/1998 Forrest
5,844,363 A 12/1998 Gu
6,200,695 B1 3/2001 Arai
6,303,238 B1 10/2001 Thompson
6,780,528 B2 8/2004 Tsuboyama
7,002,013 B1 2/2006 Chi
7,037,599 B2 5/2006 Culligan
7,064,228 B1 6/2006 Yu
7,268,485 B2 9/2007 Tyan
7,279,704 B2 10/2007 Walters
7,332,232 B2 2/2008 Ma
7,442,797 B2 10/2008 Itoh
7,501,190 B2 3/2009 Ise
7,635,792 B1 12/2009 Cella
7,655,322 B2 2/2010 Forrest
7,854,513 B2 12/2010 Quach
7,947,383 B2 5/2011 Ise
8,106,199 B2 1/2012 Jabbour
8,133,597 B2 3/2012 Yasukawa
8,389,725 B2 3/2013 Li
8,617,723 B2 12/2013 Stoessel
8,669,364 B2 3/2014 Li
8,778,509 B2 7/2014 Yasukawa
8,816,080 B2 8/2014 Li
8,846,940 B2 9/2014 Li
8,871,361 B2 10/2014 Xia
8,927,713 B2 1/2015 Li
8,933,622 B2 1/2015 Kawami
8,946,417 B2 2/2015 Jian
8,987,451 B2 3/2015 Tsai
9,059,412 B2 6/2015 Zeng
9,076,974 B2 7/2015 Li
9,082,989 B2 7/2015 Li
9,203,039 B2 12/2015 Li
9,221,857 B2 12/2015 Li
9,224,963 B2 12/2015 Li
9,238,668 B2 1/2016 Li
9,312,502 B2 4/2016 Li
9,312,505 B2 4/2016 Brooks
9,318,725 B2 4/2016 Li
9,324,957 B2 4/2016 Li
9,382,273 B2 7/2016 Li
9,385,329 B2 7/2016 Li
9,425,415 B2 8/2016 Li
9,461,254 B2 10/2016 Tsai
9,493,698 B2 11/2016 Beers
9,502,671 B2 11/2016 Jian
9,550,801 B2 1/2017 Li
9,598,449 B2 3/2017 Li
9,617,291 B2 4/2017 Li
9,666,822 B2 5/2017 Forrest
9,673,409 B2 6/2017 Li
9,698,359 B2 7/2017 Li
9,711,739 B2 7/2017 Li
9,711,741 B2 7/2017 Li
9,711,742 B2 7/2017 Li
9,735,397 B2 8/2017 Riegel
9,755,163 B2 9/2017 Li
9,818,959 B2 11/2017 Li
9,865,825 B2 1/2018 Li
9,879,039 B2 1/2018 Li
9,882,150 B2 1/2018 Li
9,899,614 B2 2/2018 Li
9,920,242 B2 3/2018 Li
9,923,155 B2 3/2018 Li
9,941,479 B2 4/2018 Li
9,947,881 B2 4/2018 Li
9,985,224 B2 5/2018 Li
10,020,455 B2 7/2018 Li
10,033,003 B2 7/2018 Li
10,056,564 B2 8/2018 Li
10,056,567 B2 8/2018 Li
10,158,091 B2 12/2018 Li
10,177,323 B2 1/2019 Li
10,211,411 B2 2/2019 Li
10,211,414 B2 2/2019 Li
10,263,197 B2 4/2019 Li
10,294,417 B2 5/2019 Li
10,392,387 B2 8/2019 Li
10,411,202 B2 9/2019 Li
10,414,785 B2 9/2019 Li
10,516,117 B2 12/2019 Li
10,566,553 B2 2/2020 Li
10,566,554 B2 2/2020 Li
10,615,349 B2 4/2020 Li
10,622,571 B2 4/2020 Li
10,727,422 B2 7/2020 Li
10,745,615 B2 8/2020 Li
10,790,457 B2 9/2020 Li
10,793,546 B2 * 10/2020 Li .......................... C09K 11/06
10,804,475 B2 10/2020 Zeng
10,804,476 B2 10/2020 Li
10,822,363 B2 11/2020 Li
10,836,785 B2 11/2020 Li
10,851,106 B2 12/2020 Li
10,886,478 B2 1/2021 Li
10,930,865 B2 2/2021 Li
10,937,976 B2 3/2021 Li
10,944,064 B2 3/2021 Li
10,964,897 B2 3/2021 Li
10,991,897 B2 4/2021 Li
10,995,108 B2 5/2021 Li
11,011,712 B2 5/2021 Li
11,063,228 B2 7/2021 Li
11,101,435 B2 8/2021 Li
11,114,626 B2 9/2021 Li
11,121,328 B2 9/2021 Li
11,145,830 B2 10/2021 Li
11,183,670 B2 11/2021 Li
11,335,865 B2 5/2022 Li
11,594,688 B2 * 2/2023 Li ........................ H10K 85/346
12,043,611 B2 * 7/2024 Li ........................ H10K 85/654
2001/0019782 A1 9/2001 Igarashi
2002/0068190 A1 6/2002 Tsuboyama
2003/0062519 A1 4/2003 Yamazaki
2003/0180574 A1 9/2003 Huang
2003/0186077 A1 10/2003 Chen
2004/0230061 A1 11/2004 Seo
2005/0037232 A1 2/2005 Tyan
2005/0139810 A1 6/2005 Kuehl
2005/0170207 A1 8/2005 Ma
2005/0260446 A1 * 11/2005 Mackenzie ............ H05B 33/14
313/506
2006/0024522 A1 2/2006 Thompson
2006/0032528 A1 2/2006 Wang
2006/0066228 A1 3/2006 Antoniadis
2006/0073359 A1 4/2006 Ise
2006/0094875 A1 5/2006 Itoh
2006/0127696 A1 6/2006 Stossel
2006/0182992 A1 8/2006 Nii
2006/0202197 A1 9/2006 Nakayama
2006/0210831 A1 9/2006 Sano
2006/0255721 A1 11/2006 Igarashi
2006/0263635 A1 11/2006 Ise

(56) References Cited

U.S. PATENT DOCUMENTS

| | | | | |
|---|---|---|---|---|
| 2006/0286406 | A1* | 12/2006 | Igarashi | H10K 85/346 313/506 |
| 2007/0057630 | A1 | 3/2007 | Nishita | |
| 2007/0059551 | A1 | 3/2007 | Yamazaki | |
| 2007/0082284 | A1 | 4/2007 | Stoessel | |
| 2007/0103060 | A1 | 5/2007 | Itoh | |
| 2007/0160905 | A1 | 7/2007 | Morishita | |
| 2007/0252140 | A1 | 11/2007 | Limmert | |
| 2008/0001530 | A1 | 1/2008 | Ise | |
| 2008/0036373 | A1 | 2/2008 | Itoh | |
| 2008/0054799 | A1 | 3/2008 | Satou | |
| 2008/0079358 | A1 | 4/2008 | Satou | |
| 2008/0102310 | A1 | 5/2008 | Thompson | |
| 2008/0111476 | A1 | 5/2008 | Choi | |
| 2008/0241518 | A1 | 10/2008 | Satou | |
| 2008/0241589 | A1 | 10/2008 | Fukunaga | |
| 2008/0269491 | A1 | 10/2008 | Jabbour | |
| 2008/0315187 | A1 | 12/2008 | Bazan | |
| 2009/0026936 | A1 | 1/2009 | Satou | |
| 2009/0026939 | A1 | 1/2009 | Kinoshita | |
| 2009/0032989 | A1 | 2/2009 | Karim | |
| 2009/0039768 | A1 | 2/2009 | Igarashi | |
| 2009/0079340 | A1 | 3/2009 | Kinoshita | |
| 2009/0126796 | A1 | 5/2009 | Yang | |
| 2009/0128008 | A1 | 5/2009 | Ise | |
| 2009/0136779 | A1 | 5/2009 | Cheng | |
| 2009/0153045 | A1 | 6/2009 | Kinoshita | |
| 2009/0167157 | A1 | 7/2009 | Murakami | |
| 2009/0167167 | A1 | 7/2009 | Aoyama | |
| 2009/0205713 | A1 | 8/2009 | Mitra | |
| 2009/0218561 | A1 | 9/2009 | Kitamura | |
| 2009/0261721 | A1 | 10/2009 | Murakami | |
| 2009/0267500 | A1 | 10/2009 | Kinoshita | |
| 2010/0000606 | A1 | 1/2010 | Thompson | |
| 2010/0013386 | A1 | 1/2010 | Thompson | |
| 2010/0043876 | A1 | 2/2010 | Tuttle | |
| 2010/0093119 | A1 | 4/2010 | Shimizu | |
| 2010/0127246 | A1 | 5/2010 | Nakayama | |
| 2010/0141127 | A1 | 6/2010 | Xia | |
| 2010/0147386 | A1 | 6/2010 | Benson-Smith | |
| 2010/0171111 | A1 | 7/2010 | Takada | |
| 2010/0171418 | A1 | 7/2010 | Kinoshita | |
| 2010/0200051 | A1 | 8/2010 | Triani | |
| 2010/0204467 | A1 | 8/2010 | Lamarque | |
| 2010/0270540 | A1 | 10/2010 | Chung | |
| 2010/0288362 | A1 | 11/2010 | Hatwar | |
| 2010/0297522 | A1 | 11/2010 | Creeth | |
| 2010/0301315 | A1 | 12/2010 | Masui | |
| 2010/0307594 | A1 | 12/2010 | Zhu | |
| 2011/0028723 | A1 | 2/2011 | Li | |
| 2011/0049496 | A1 | 3/2011 | Fukuzaki | |
| 2011/0062858 | A1 | 3/2011 | Yersin | |
| 2011/0132440 | A1 | 6/2011 | Sivarajan | |
| 2011/0217544 | A1 | 9/2011 | Young | |
| 2011/0227058 | A1 | 9/2011 | Masui | |
| 2011/0301351 | A1 | 12/2011 | Li | |
| 2012/0024383 | A1 | 2/2012 | Kaiho | |
| 2012/0025588 | A1 | 2/2012 | Humbert | |
| 2012/0039323 | A1 | 2/2012 | Hirano | |
| 2012/0095232 | A1 | 4/2012 | Li | |
| 2012/0108806 | A1 | 5/2012 | Li | |
| 2012/0146012 | A1 | 6/2012 | Limmert | |
| 2012/0181528 | A1 | 7/2012 | Takada | |
| 2012/0199823 | A1 | 8/2012 | Molt | |
| 2012/0202997 | A1 | 8/2012 | Parham | |
| 2012/0204960 | A1 | 8/2012 | Kato | |
| 2012/0215001 | A1 | 8/2012 | Li | |
| 2012/0223634 | A1 | 9/2012 | Xia | |
| 2012/0264938 | A1 | 10/2012 | Li | |
| 2012/0273736 | A1 | 11/2012 | James | |
| 2012/0302753 | A1 | 11/2012 | Li | |
| 2013/0048963 | A1 | 2/2013 | Beers | |
| 2013/0082245 | A1 | 4/2013 | Kottas | |
| 2013/0137870 | A1 | 5/2013 | Li | |
| 2013/0168656 | A1 | 7/2013 | Tsai | |
| 2013/0172561 | A1 | 7/2013 | Tsai | |
| 2013/0200340 | A1 | 8/2013 | Otsu | |
| 2013/0203996 | A1 | 8/2013 | Li | |
| 2013/0237706 | A1 | 9/2013 | Li | |
| 2013/0341600 | A1 | 12/2013 | Lin | |
| 2014/0014922 | A1 | 1/2014 | Lin | |
| 2014/0014931 | A1 | 1/2014 | Riegel | |
| 2014/0027733 | A1 | 1/2014 | Zeng | |
| 2014/0042475 | A1 | 2/2014 | Park | |
| 2014/0066628 | A1 | 3/2014 | Li | |
| 2014/0073798 | A1 | 3/2014 | Li | |
| 2014/0084261 | A1 | 3/2014 | Brooks | |
| 2014/0114072 | A1 | 4/2014 | Li | |
| 2014/0147996 | A1 | 5/2014 | Vogt | |
| 2014/0148594 | A1 | 5/2014 | Li | |
| 2014/0191206 | A1 | 7/2014 | Cho | |
| 2014/0203248 | A1 | 7/2014 | Zhou | |
| 2014/0249310 | A1 | 9/2014 | Li | |
| 2014/0326960 | A1 | 11/2014 | Kim | |
| 2014/0330019 | A1 | 11/2014 | Li | |
| 2014/0364605 | A1 | 12/2014 | Li | |
| 2014/0374728 | A1 | 12/2014 | Adamovich | |
| 2015/0008419 | A1 | 1/2015 | Li | |
| 2015/0018558 | A1 | 1/2015 | Li | |
| 2015/0028323 | A1 | 1/2015 | Xia | |
| 2015/0060804 | A1 | 3/2015 | Kanitz | |
| 2015/0069334 | A1 | 3/2015 | Xia | |
| 2015/0105556 | A1 | 4/2015 | Li | |
| 2015/0123047 | A1 | 5/2015 | Maltenberger | |
| 2015/0162552 | A1 | 6/2015 | Li | |
| 2015/0194616 | A1 | 7/2015 | Li | |
| 2015/0207086 | A1 | 7/2015 | Li | |
| 2015/0228914 | A1 | 8/2015 | Li | |
| 2015/0274762 | A1 | 10/2015 | Li | |
| 2015/0287938 | A1 | 10/2015 | Li | |
| 2015/0311456 | A1 | 10/2015 | Li | |
| 2015/0318500 | A1 | 11/2015 | Li | |
| 2015/0349279 | A1 | 12/2015 | Li | |
| 2015/0380666 | A1 | 12/2015 | Szigethy | |
| 2016/0028028 | A1 | 1/2016 | Li | |
| 2016/0028029 | A1 | 1/2016 | Li | |
| 2016/0043331 | A1 | 2/2016 | Li | |
| 2016/0072082 | A1 | 3/2016 | Brooks | |
| 2016/0130225 | A1 | 5/2016 | Tasaki | |
| 2016/0133861 | A1 | 5/2016 | Li | |
| 2016/0133862 | A1 | 5/2016 | Li | |
| 2016/0181529 | A1 | 6/2016 | Tsai | |
| 2016/0194344 | A1 | 7/2016 | Li | |
| 2016/0197285 | A1 | 7/2016 | Zeng | |
| 2016/0197291 | A1 | 7/2016 | Li | |
| 2016/0204358 | A1 | 7/2016 | Stoessel | |
| 2016/0285015 | A1 | 9/2016 | Li | |
| 2016/0359120 | A1 | 12/2016 | Li | |
| 2016/0359125 | A1 | 12/2016 | Li | |
| 2017/0005278 | A1 | 1/2017 | Li | |
| 2017/0012224 | A1 | 1/2017 | Li | |
| 2017/0040555 | A1 | 2/2017 | Li | |
| 2017/0047533 | A1 | 2/2017 | Li | |
| 2017/0066792 | A1 | 3/2017 | Li | |
| 2017/0069855 | A1 | 3/2017 | Li | |
| 2017/0077420 | A1 | 3/2017 | Li | |
| 2017/0125708 | A1 | 5/2017 | Li | |
| 2017/0267923 | A1 | 9/2017 | Li | |
| 2017/0271611 | A1 | 9/2017 | Li | |
| 2017/0301871 | A1 | 10/2017 | Li | |
| 2017/0305881 | A1 | 10/2017 | Li | |
| 2017/0309943 | A1 | 10/2017 | Angell | |
| 2017/0331056 | A1 | 11/2017 | Li | |
| 2017/0342098 | A1 | 11/2017 | Li | |
| 2017/0373260 | A1 | 12/2017 | Li | |
| 2018/0006246 | A1 | 1/2018 | Li | |
| 2018/0013096 | A1 | 1/2018 | Hamada | |
| 2018/0037812 | A1 | 2/2018 | Pegington | |
| 2018/0052366 | A1 | 2/2018 | Hao | |
| 2018/0053904 | A1 | 2/2018 | Li | |
| 2018/0062084 | A1 | 3/2018 | Watabe | |
| 2018/0130960 | A1 | 5/2018 | Li | |
| 2018/0138428 | A1 | 5/2018 | Li | |
| 2018/0148464 | A1 | 5/2018 | Li | |

(56) References Cited

U.S. PATENT DOCUMENTS

| | | | |
|---|---|---|---|
| 2018/0159051 A1 | 6/2018 | Li | |
| 2018/0166655 A1 | 6/2018 | Li | |
| 2018/0175329 A1 | 6/2018 | Li | |
| 2018/0194790 A1 | 7/2018 | Li | |
| 2018/0198081 A1 | 7/2018 | Zeng | |
| 2018/0219161 A1 | 8/2018 | Li | |
| 2018/0226592 A1 | 8/2018 | Li | |
| 2018/0226593 A1 | 8/2018 | Li | |
| 2018/0230173 A1 | 8/2018 | Ji | |
| 2018/0277777 A1 | 9/2018 | Li | |
| 2018/0301641 A1 | 10/2018 | Li | |
| 2018/0312750 A1 | 11/2018 | Li | |
| 2018/0331307 A1 | 11/2018 | Li | |
| 2018/0334459 A1 | 11/2018 | Li | |
| 2018/0337345 A1 | 11/2018 | Li | |
| 2018/0337349 A1 | 11/2018 | Li | |
| 2018/0337350 A1 | 11/2018 | Li | |
| 2018/0353771 A1 | 12/2018 | Kim | |
| 2019/0013485 A1 | 1/2019 | Li | |
| 2019/0058137 A1 | 2/2019 | Ko | |
| 2019/0067602 A1 | 2/2019 | Li | |
| 2019/0074455 A1 | 3/2019 | Chen | |
| 2019/0109288 A1 | 4/2019 | Li | |
| 2019/0119312 A1 | 4/2019 | Chen | |
| 2019/0157352 A1 | 5/2019 | Li | |
| 2019/0194536 A1 | 6/2019 | Li | |
| 2019/0214584 A1 | 7/2019 | Chen | |
| 2019/0221757 A1 | 7/2019 | Tarran | |
| 2019/0259963 A1 | 8/2019 | Jian | |
| 2019/0276485 A1 | 9/2019 | Li | |
| 2019/0312217 A1 | 10/2019 | Li | |
| 2019/0367546 A1 | 12/2019 | Li | |
| 2019/0389893 A1 | 12/2019 | Li | |
| 2020/0006678 A1 | 1/2020 | Li | |
| 2020/0055885 A1 | 2/2020 | Tarran | |
| 2020/0071330 A1 | 3/2020 | Li | |
| 2020/0075868 A1 | 3/2020 | Li | |
| 2020/0119288 A1 | 4/2020 | Li | |
| 2020/0119289 A1 | 4/2020 | Lin | |
| 2020/0140471 A1 | 5/2020 | Chen | |
| 2020/0152891 A1 | 5/2020 | Li | |
| 2020/0168798 A1 | 5/2020 | Han | |
| 2020/0203636 A1* | 6/2020 | Fleetham | H10K 85/331 |
| 2020/0227656 A1 | 7/2020 | Li | |
| 2020/0227660 A1 | 7/2020 | Li | |
| 2020/0239505 A1 | 7/2020 | Li | |
| 2020/0243776 A1 | 7/2020 | Li | |
| 2020/0287153 A1 | 9/2020 | Li | |
| 2020/0332185 A1 | 10/2020 | Li | |
| 2020/0365819 A1 | 11/2020 | Seo | |
| 2020/0373505 A1 | 11/2020 | Li | |
| 2020/0403167 A1 | 12/2020 | Li | |
| 2020/0411775 A1 | 12/2020 | Chen | |
| 2021/0024526 A1 | 1/2021 | Li | |
| 2021/0024559 A1 | 1/2021 | Li | |
| 2021/0047296 A1 | 2/2021 | Li | |
| 2021/0091316 A1 | 3/2021 | Li | |
| 2021/0095195 A1 | 4/2021 | Ma | |
| 2021/0104687 A1 | 4/2021 | Li | |
| 2021/0111355 A1 | 4/2021 | Jian | |
| 2021/0126208 A1 | 4/2021 | Li | |
| 2021/0193936 A1 | 6/2021 | Li | |
| 2021/0193947 A1 | 6/2021 | Li | |
| 2021/0206785 A1 | 7/2021 | Hamze | |
| 2021/0217973 A1 | 7/2021 | Li | |
| 2021/0230198 A1 | 7/2021 | Li | |
| 2021/0261589 A1 | 8/2021 | Li | |
| 2021/0273182 A1 | 9/2021 | Li | |
| 2021/0292351 A1 | 9/2021 | Macinnis | |
| 2021/0376260 A1 | 12/2021 | Li | |
| 2022/0059786 A1 | 2/2022 | Seo | |

FOREIGN PATENT DOCUMENTS

| | | | |
|---|---|---|---|
| CN | 1894267 | | 1/2007 |
| CN | 1894269 | A | 1/2007 |
| CN | 101142223 | A | 3/2008 |
| CN | 101667626 | | 3/2010 |
| CN | 102449108 | A | 5/2012 |
| CN | 102892860 | A | 1/2013 |
| CN | 102971396 | A | 3/2013 |
| CN | 103102372 | A | 5/2013 |
| CN | 104232076 | A | 12/2014 |
| CN | 104377231 | | 2/2015 |
| CN | 104576934 | | 4/2015 |
| CN | 104693243 | A | 6/2015 |
| CN | 105367605 | A | 3/2016 |
| CN | 105418591 | A | 3/2016 |
| CN | 106783922 | | 5/2017 |
| CN | 109309168 | A | 2/2019 |
| CN | 110066296 | A | 7/2019 |
| CN | 110240606 | A | 9/2019 |
| EP | 1617493 | | 1/2006 |
| EP | 1808052 | A1 | 7/2007 |
| EP | 1874893 | A1 | 1/2008 |
| EP | 1874894 | A1 | 1/2008 |
| EP | 1919928 | A1 | 5/2008 |
| EP | 1968131 | | 9/2008 |
| EP | 2020694 | | 2/2009 |
| EP | 2036907 | A1 | 3/2009 |
| EP | 2096690 | | 9/2009 |
| EP | 2112213 | A2 | 10/2009 |
| EP | 2417217 | A2 | 2/2012 |
| EP | 2684932 | | 1/2014 |
| EP | 2711999 | A2 | 3/2014 |
| EP | 3032293 | | 6/2016 |
| JP | 2002010505 | | 1/2002 |
| JP | 2002105055 | | 4/2002 |
| JP | 2003342284 | | 12/2003 |
| JP | 2005031073 | | 2/2005 |
| JP | 2005267557 | | 9/2005 |
| JP | 2005310733 | A | 11/2005 |
| JP | 2006047240 | A | 2/2006 |
| JP | 2006232784 | A | 9/2006 |
| JP | 2006242080 | | 9/2006 |
| JP | 2006242081 | A | 9/2006 |
| JP | 2006256999 | A | 9/2006 |
| JP | 2006257238 | A | 9/2006 |
| JP | 2006261623 | A | 9/2006 |
| JP | 2006290988 | A | 10/2006 |
| JP | 2006313796 | A | 11/2006 |
| JP | 2006332622 | A | 12/2006 |
| JP | 2006351638 | A | 12/2006 |
| JP | 2007019462 | A | 1/2007 |
| JP | 2007031678 | | 2/2007 |
| JP | 2007042875 | A | 2/2007 |
| JP | 2007051243 | A | 3/2007 |
| JP | 2007053132 | A * | 3/2007 |
| JP | 2007066581 | | 3/2007 |
| JP | 2007073620 | A | 3/2007 |
| JP | 2007073845 | A | 3/2007 |
| JP | 2007073900 | A | 3/2007 |
| JP | 2007080593 | | 3/2007 |
| JP | 2007080677 | A | 3/2007 |
| JP | 2007088105 | | 4/2007 |
| JP | 2007088164 | A | 4/2007 |
| JP | 2007096259 | A | 4/2007 |
| JP | 2007099765 | A | 4/2007 |
| JP | 2007110067 | | 4/2007 |
| JP | 2007110102 | A | 4/2007 |
| JP | 2007519614 | | 7/2007 |
| JP | 2007258550 | A | 10/2007 |
| JP | 2007324309 | A | 12/2007 |
| JP | 2008010353 | A | 1/2008 |
| JP | 2008091860 | A | 4/2008 |
| JP | 2008103535 | A | 5/2008 |
| JP | 2008108617 | A | 5/2008 |
| JP | 2008109085 | | 5/2008 |
| JP | 2008109103 | A | 5/2008 |
| JP | 2008116343 | A | 5/2008 |
| JP | 2008117545 | A | 5/2008 |

(56) References Cited

FOREIGN PATENT DOCUMENTS

| | | | |
|---|---|---|---|
| JP | 2008160087 | A | 7/2008 |
| JP | 2008198801 | A | 8/2008 |
| JP | 2008270729 | A | 11/2008 |
| JP | 2008270736 | | 11/2008 |
| JP | 2008310220 | A | 12/2008 |
| JP | 2009016184 | A | 1/2009 |
| JP | 2009016579 | | 1/2009 |
| JP | 2009032977 | A | 2/2009 |
| JP | 2009032988 | A | 2/2009 |
| JP | 2009059997 | | 3/2009 |
| JP | 2009076509 | | 4/2009 |
| JP | 2009161524 | A | 7/2009 |
| JP | 2009247171 | | 10/2009 |
| JP | 2009266943 | A | 11/2009 |
| JP | 2009267171 | A | 11/2009 |
| JP | 2009267244 | A | 11/2009 |
| JP | 2009272339 | A | 11/2009 |
| JP | 2009283891 | A | 12/2009 |
| JP | 4460952 | B2 | 5/2010 |
| JP | 2010135689 | A | 6/2010 |
| JP | 2010171205 | A | 8/2010 |
| JP | 2011071452 | A | 4/2011 |
| JP | 2012074444 | A | 4/2012 |
| JP | 2012079895 | A | 4/2012 |
| JP | 2012079898 | A | 4/2012 |
| JP | 5604505 | | 9/2012 |
| JP | 2012522843 | | 9/2012 |
| JP | 2012207231 | A | 10/2012 |
| JP | 2012222255 | A | 11/2012 |
| JP | 2012231135 | A | 11/2012 |
| JP | 2013023500 | A | 2/2013 |
| JP | 2013048256 | A | 3/2013 |
| JP | 2013053149 | A | 3/2013 |
| JP | 2013525436 | | 6/2013 |
| JP | 2014019701 | A | 2/2014 |
| JP | 2014058504 | A | 4/2014 |
| JP | 2014520096 | | 8/2014 |
| JP | 2012709899 | | 11/2014 |
| JP | 2014221807 | A | 11/2014 |
| JP | 2014239225 | A | 12/2014 |
| JP | 2015081257 | A | 4/2015 |
| KR | 20060011537 | | 2/2006 |
| KR | 20060015371 | | 2/2006 |
| KR | 20060115371 | | 11/2006 |
| KR | 20070061830 | | 6/2007 |
| KR | 20070112465 | | 11/2007 |
| KR | 20130043460 | A | 4/2013 |
| KR | 101338250 | | 12/2013 |
| KR | 20140052501 | | 5/2014 |
| TW | 200701835 | | 1/2007 |
| TW | 201249851 | | 12/2012 |
| TW | 201307365 | A | 2/2013 |
| TW | 201710277 | | 3/2017 |
| WO | 2000070655 | | 11/2000 |
| WO | 2004003108 | | 1/2004 |
| WO | 2004070655 | | 8/2004 |
| WO | 2004085450 | | 10/2004 |
| WO | 2004108857 | A1 | 12/2004 |
| WO | 2005042444 | A2 | 5/2005 |
| WO | 2005042550 | A1 | 5/2005 |
| WO | 2005113704 | | 12/2005 |
| WO | 2006033440 | A1 | 3/2006 |
| WO | 2006067074 | | 6/2006 |
| WO | 2006081780 | | 8/2006 |
| WO | 2006098505 | A1 | 9/2006 |
| WO | 2006113106 | | 10/2006 |
| WO | 2006115299 | A1 | 11/2006 |
| WO | 2006115301 | | 11/2006 |
| WO | 2007034985 | A1 | 3/2007 |
| WO | 2007069498 | A1 | 6/2007 |
| WO | 2008054578 | | 5/2008 |
| WO | 2008066192 | A1 | 6/2008 |
| WO | 2008066195 | A1 | 6/2008 |
| WO | 2008066196 | A1 | 6/2008 |
| WO | 2008101842 | A1 | 8/2008 |
| WO | 2008117889 | | 10/2008 |
| WO | 2008123540 | | 10/2008 |
| WO | 2008131932 | A1 | 11/2008 |
| WO | 2009003455 | | 1/2009 |
| WO | 2009008277 | | 1/2009 |
| WO | 2009011327 | | 1/2009 |
| WO | 2009017211 | A1 | 2/2009 |
| WO | 2009023667 | | 2/2009 |
| WO | 2009086209 | | 7/2009 |
| WO | 2009111299 | | 9/2009 |
| WO | 2010007098 | A1 | 1/2010 |
| WO | 2010056669 | | 5/2010 |
| WO | 2010093176 | | 8/2010 |
| WO | 2010105141 | | 9/2010 |
| WO | 2010118026 | A2 | 10/2010 |
| WO | 2011064335 | A1 | 6/2011 |
| WO | 2011070989 | A1 | 6/2011 |
| WO | 2011089163 | | 7/2011 |
| WO | 2011137429 | A2 | 11/2011 |
| WO | 2011137431 | A2 | 11/2011 |
| WO | 2012074909 | | 6/2012 |
| WO | 2012112853 | A1 | 8/2012 |
| WO | 2012116231 | A2 | 8/2012 |
| WO | 2012142387 | | 10/2012 |
| WO | 2012162488 | A1 | 11/2012 |
| WO | 2012163471 | A1 | 12/2012 |
| WO | 2013130483 | A1 | 9/2013 |
| WO | 2014009310 | | 1/2014 |
| WO | 2014016611 | | 1/2014 |
| WO | 2014031977 | | 2/2014 |
| WO | 2014047616 | A1 | 3/2014 |
| WO | 2014109814 | | 7/2014 |
| WO | 2014208271 | | 12/2014 |
| WO | 2015027060 | A1 | 2/2015 |
| WO | 2015131158 | | 9/2015 |
| WO | 2016025921 | A1 | 2/2016 |
| WO | 2016029137 | | 2/2016 |
| WO | 2016029186 | | 2/2016 |
| WO | 2016088354 | A1 | 6/2016 |
| WO | 2016197019 | | 12/2016 |
| WO | 2017117935 | | 7/2017 |
| WO | 2018071697 | | 4/2018 |
| WO | 2018140765 | | 8/2018 |
| WO | 2019079505 | | 4/2019 |
| WO | 2019079508 | | 4/2019 |
| WO | 2019079509 | | 4/2019 |
| WO | 2019236541 | | 12/2019 |
| WO | 2020018476 | | 1/2020 |

OTHER PUBLICATIONS

M. Hopkinson et al., 510 Nature, 485-496 (2014) (Year: 2014).*

Pui-Keong Chow et al., "Highly luminescent palladium(II) complexes with sub-millisecond blue to green phosphorescent excited states. Photocatalysis and highly efficient PSF-OLEDs," Chem. Sci., 2016, 7, 6083-6098.

Results from SciFinder Compound Search on Dec. 8, 2016. (17 pages).

Rui Zhu et al., "Color tuning based on a six-membered chelated iridium (III) complex with aza-aromatic ligand," Chemistry Letters, vol. 34, No. 12, 2005, pp. 1668-1669.

Russell J. Holmes et al., "Blue and Near-UV Phosphorescence from Iridium Complexes with Cyclometalated Pyrazolyl or N-Heterocyclic Carbene Ligands," Inorganic Chemistry, 2005, vol. 44, No. 22, pp. 7995-8003.

S. Kunic et al., 54th International Symposium ELMAR-2012, 31-35 (2012) (Year: 2012).

S. Lamansky et al., "Synthesis and Characterization of Phosphorescent Cyclometalated Iridium Complexes", Inorg. Chem., vol. 40, pp. 1704-1711, 2001.

Sajoto, T. et al., "Temperature Dependence of Blue Phosphorescent Cyclometalated Ir(III) Complexes", Journal of the American Chemical Society, Jun. 2009, vol. 131, No. 28, pp. 9813-9822 <DOI:10.1021/ja903317w>.

Sakai, Y. et al., "Simple model-free estimation of orientation order parameters of vacuum-deposited and spin-coated amorphous films

(56) References Cited

OTHER PUBLICATIONS used in organic light-emitting diodes", Applied Physics Express, Aug. 2015, vol. 8, No. 9, pp. 096601-1-096601-4 <DOI:10.7567/APEX.8.096601>.
Saricifci et al. (1993). "Semiconducting polymerbuckminsterfullerene heterojunctions: diodes photodiodes, and photovoltaic cells," Appl. Phys. Lett., 62, 585-87.
Satake et al., "Interconvertible Cationic and Neutral Pyridinylimidazole .eta.3-Allylpalladium Complexes. Structural Assignment by 1H, 13C, and 15N Nmr and X-ray Diffraction, Organometallics", vol. 18, No. 24, 1999, pp. 5108-5111.
Saunders et al. (2008). "Nanoparticle-polymer photovoltaic cells," Advances in Colloid and Interface Science, 138, 1-23.
Senes, A. et al., "Transition dipole moment orientation in films of solution processed fluorescent oligomers: investigating the influence of molecular anisotropy", Journal of Materials Chemistry C, Jun. 2016, vol. 4, No. 26, pp. 6302-6308 <DOI:10.1039/c5tc03481g>.
Shih-Chun Lo et al., "High-Triplet-Energy Dendrons: Enhancing the Luminescence of Deep Blue Phosphorescent Indium(III) Complexes," J. Am. Chem. Soc., vol. 131, 2009, pp. 16681-16688.
Shin et al. (2010). "Abrupt morphology change upon thermal annealing in Poly(3-hexathiophene)/soluble fullerene blend films for polymer solar cells," Adv. Funct. Mater., 20, 748-54.
Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).
Shizuo Tokito et al., "Confinement of triplet energy on phosphorescent molecules for highly-efficient organic blue-light-emitting devices," Applied Physics Letters, vol. 83, No. 3, Jul. 21, 2003, pp. 569-571.
Stefan Bernhard, "The First Six Years: A Report," Department of Chemistry, Princeton University, May 2008, 11 pages.
Stephen R. Forrest, "The path to ubiquitous and low-cost organic electronic appliances on plastic," Nature, vol. 428, Apr. 29, 2004, pp. 911-918.
Steven C. F. Kui et al., "Robust phosphorescent platinum(II) complexes with tetradentate OLambdaNLambdaCLambdaN ligands: high efficiency OLEDs with excellent efficiency stability," Chem. Commun., 2013, vol. 49pp. 1497-1499.
Steven C. F. Kui et al., "Robust Phosphorescent Platinum(II) Complexes Containing Tetradentate ÔN̂ĈN Ligands: Excimeric Excited State and Application in Organic White-Light-Emitting Diodes," Chem. Eur. J., 2013, vol. 19, pp. 69-73.
Strouse, G. et al., "Optical Spectroscopy of Single Crystal [Re(bpy)(CO)4](PF6): Mixing between Charge Transfer and Ligand Centered Excited States", Inorganic Chemistry, Oct. 1995, vol. 34, No. 22, pp. 5578-5587 <DOI:10.1021/ic00126a031>.
Supporting Information: Xiao-Chun Hang et al., "Highly Efficient Blue-Emitting Cyclometalated Platinum(II) Complexes by Judicious Molecular Design," Wiley-VCH 2013, 7 pages.
T. Fleetham et al., 25 Advanced Materials, 2573-2576 (2013) (Year: 2013).
Tang, C. et al., "Organic electroluminescent diodes", Applied Physics Letters, Jul. 1987, vol. 51, No. 12, pp. 913-915 <DOI:10.1063/1.98799>.
Tsuoboyama, A. et al., "Homoleptic Cyclometalated Iridium Complexes with Highly Efficient Red Phosphorescence and Application to Organic Light-Emitting Diode", Journal of the American Chemical Society, Sep. 2003, vol. 125, No. 42, pp. 12971-12979 <DOI:10.1021/ja034732d>.
Turro, N., "Modern Molecular Photochemistry" (Sausalito, California, University Science Books, 1991), p. 48. (3 pages).
Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.
Tyler Fleetham et al., "Efficient Red-Emitting Platinum Complex with Long Operational Stability," ACS Appl. Mater. Interfaces 2015, 7, 16240-16246.
Tyler Fleetham, "Phosphorescent Pt(II) and Pd(II) Complexes for Efficient, High-Color-Quality, and Stable OLEDs", 52 pages, Material Science and Engineering, Arizona State University (Year: 2016).
V. Adamovich et al., "High efficiency single dopant white electrophosphorescent light emitting diodes", New J. Chem, vol. 26, pp. 1171-1178. 2002.
V. Thamilarasan et al., "Green-emitting phosphorescent iridium(III) complex: Structural, photophysical and electrochemical properties," Inorganica Chimica Acta, vol. 408, 2013, pp. 240-245.
Vanessa Wood et al., "Colloidal quantum dot light-emitting devices," Nano Reviews 1, Jul. 2010, pp. 5202. (7 pages).
Vezzu, D. et al.: Highly luminescent tridentate platinum (II) complexes featured in fused five-six-membered metallacycle and diminishing concentration quenching. Inorganic Chem., vfol. 50 (17), pp. 8261-8273, 2011.
Wang et al. (2010). "The development of nanoscale morphology in polymer: fullerene photovoltaic blends during solvent casting," Soft Matter, 6, 4128-4134.
Wang et al., C(aryl)-C(alkyl) bond formation from Cu(Cl04)2-mediated oxidative cross coupling reaction between arenes and alkyllithium reagents through structurally well-defined Ar—Cu(III) intermediates, Chem Commun, 48: 9418-9420 (2012).
Williams et al., "Organic light-emitting diodes having exclusive near-infrared electrophosphorescence", Applied Physics Letters, vol. 89, pp. 083506 (3 pages), 2006.
Williams, E. et al., "Excimer-Based White Phosphorescent Organic Light-Emitting Diodes with Nearly 100 % Internal Quantum Efficiency", Advanced Materials, Jan. 2007, vol. 19, No. 2, pp. 197-202 <DOI:10.1002/adma.200602174>.
Wong; Challenges in organometallic research—Great opportunity for solar cells and OLEDs, Journal of Organometallic Chemistry, 2009, 6942644-2647.
Written Opinion mailed on Aug. 17, 2012 for Intl. Pat. App. No. PCT/US2012/039323 filed May 24, 2012 and published as WO 2012/162488 on Nov. 29, 2012 (Applicants—Arizona Board of Regents Acting for and on Behalf of Arizona State University; Inventors—Li et al.; (6 pages).
Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.
Xiaofan Ren et al., "Ultrahigh Energy Gap Hosts in Deep Blue Organic Electrophosphorescent Devices," Chem. Mater., vol. 16, 2004, pp. 4743-4747.
Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.
Y. Karzazi, 5 J. Mater. Environ. Sci., 1-12 (2014) (Year: 2014).
Yakubov, L.A. et al., Synthesis and Properties of Zinc Complexes of mesoHexadecyloxy-Substituted Tetrabenzoporphyrin and Tetrabenzoazaporphyrins, Russian Journal of Organic Chemistry, 2008, vol. 44, No. 5, pp. 755-760.
Yang et al. (2005). "Nanoscale morphology of high-performance polymer solar cells," Nano Lett., 5, 579-83.
Yang, X. et al., "Efficient Blue- and White-Emitting Electrophosphorescent Devices Based on Platinum(II) [1,3- Difluoro-4,6-di(2-pyridinyl)benzene] Chloride", Advanced Materials, Jun. 2008, vol. 20, No. 12, pp. 2405-2409 <DOI:10.1002/adma.200702940>.
Yao et al. (2008). "Effect of solvent mixture on nanoscale phase separation in polymer solar cells," Adv. Funct. Mater., 18, 1783-89.
Yao et al., Cu(Cl04)2-Mediated Arene C—H Bond Halogenations of Azacalixaromatics Using Alkali Metal Halides as Halogen Sources, The Journal of Organic Chemistry, 77(7): 3336-3340 (2012).
Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013pp. 2624-2628.
Yu et al. (1995). "Polymer Photovoltaic Cells: Enhanced efficiencies via a network of internal donor-acceptor heterojunctions," Science, 270, 1789-91.

(56) References Cited

OTHER PUBLICATIONS

Adachi, C. et al., "High-efficiency organic electrophosphorescent devices with tris(2-phenylpyridine)iridium doped into electron-transporting materials", Applied Physics Letters, Aug. 2000, vol. 77, No. 6, pp. 904-906 <DOI:10.1063/1.1306639>.
Ayan Maity et al., "Room-temperature synthesis of cyclometalated iridium(III) complexes; kinetic isomers and reactive functionalities", Chem. Sci., vol. 4, 2013, pp. 1175-1181.
Baldo et al., "Very High-Efficiency Green Organic Light-Emitting Devices Based on Electrophosphorescence", Appl Phys Lett, 75(3):4-6 (1999).
Baldo et al., Highly Efficient Phosphorescent Emission from Organic Electroluminescent Devices, Nature, 395: 151-154 (1998).
Baldo, M. et al., "Excitonic singlet-triplet ratio in a semiconducting organic thin film", Physical Review B, Nov. 1999, vol. 60, No. 20, pp. 14422-14428 <DOI:10.1103/PhysRevB.60.14422>.
Baldo, M. et al., "High-efficiency fluorescent organic light-emitting devices using a phosphorescent sensitizer", Nature, Feb. 2000, vol. 403, pp. 750-753.
Barry O'Brien et al., "High efficiency white organic light emitting diodes employing blue and red platinum emitters," Journal of Photonics for Energy, vol. 4, 2014, pp. 043597-1-043597-8.
Barry O'Brien et al.: White organic light emitting diodes using Pt-based red, green and blue phosphorescent dopants. Proc. SPIE, vol. 8829, pp. 1-6, Aug. 25, 2013.
Berson et al. (2007). "Poly(3-hexylthiophene) fibers for photovoltaic applications," Adv. Funct. Mat., 17, 1377-84.
Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.
Bouman et al. (1994). "Chiroptical properties of regioregular chiral polythiophenes," Mol. Cryst. Liq. Cryst., 256, 439-48.
Brian W. D'Andrade et al., "Controlling Exciton Diffusion in Multilayer White Phosphorescent Organic Light Emitting Devices," Adv. Mater., vol. 14, No. 2, Jan. 16, 2002, pp. 147-151.
Bronner; "Dipyrrin based luminescent cyclometallated palladium and platinum complexes", Dalton Trans., 2010, 39, 180-184. DOI: 10.1039/b908424j (Year: 2010) (5 pages).
Brooks, J. et al., "Synthesis and Characterization of Phosphorescent Cyclometalated Platinum Complexes", Inorganic Chemistry, May 2002, vol. 41, No. 12, pp. 3055-3066 <DOI:10. 1021/ic0255508>.
Brown, A. et al., "Optical spectroscopy of triplet excitons and charged excitations in poly(p. phenylenevinylene) light-emitting diodes", Chemical Physics Letters, Jul. 1993, vol. 210, No. 1-3, pp. 61-66 <DOI:10.1016/0009-2614(93)89100-V>.
Burroughes, J. et al., "Light-emitting diodes based on conjugated polymers", Nature, Oct. 1990, vol. 347, pp. 539-541.
Campbell et al. (2008). "Low-temperature control of nanoscale morphology for high performance polymer photovoltaics," Nano Lett., 8, 3942-47.
Chen, F. et al., "High-performance polymer light-emitting diodes doped with a red phosphorescent iridium complex", Applied Physics Letters, Apr. 2002 [available online Mar. 2002], vol. 80, No. 13, pp. 2308-2310 <10.1063/1.1462862>.
Chen, X., et al., "Fluorescent Chemosensors Based on Spiroring-Opening of Xanthenes and Related Derivatives", Chemical Reviews, 2012 [available online Oct. 2011], vol. 112, No. 3, pp. 1910-1956 <DOI:10.1021/cr200201z>.
Chew, S. et al.: Photoluminescence and electroluminescence of a new blue-emitting homoleptic iridium complex. Applied Phys. Letters; vol. 88, pp. 093510-1-093510-3, 2006.
Chi et al., "Transition-metal phosphors with cyclometalating ligands: fundamentals and applications", Chemical Society Reviews, vol. 39, No. 2, Feb. 2010, pp. 638-655.
Chi-Ming Che et al., "Photophysical Properties and OLED Applications of Phosphorescent Platinum(II) Schiff Base Complexes," Chem. Eur. J., vol. 16, 2010, pp. 233-247.
Christoph Ulbricht et al., "Synthesis and Characterization of Oxetane-Functionalized Phosphorescent Ir(III)-Complexes", Macromol. Chem. Phys. 2009, 210, pp. 531-541.
Coakley et al. (2004). "Conjugated polymer photovoltaic cells," Chem. Mater., 16, 4533-4542.
Colombo, M. et al., "Synthesis and high-resolution optical spectroscopy of bis[2-(2-thienyl)pyridinato-C3,N'](2,2'-bipyridine)iridium(III)", Inorganic Chemistry, Jul. 1993, vol. 32, No. 14, pp. 3081-3087 <DOI:10.1021/ic00066a019>.
D.F. O'Brien et al., "Improved energy transfer in electrophosphorescent devices," Appl. Phys. Lett., vol. 74, No. 3, Jan. 18, 1999, pp. 442-444.
D'andrade, B. et al., "Operational stability of electrophosphorescent devices containing p and n doped transport layers ", Applied Physics Letters, Nov. 2003, vol. 83, No. 19, pp. 3858-3860 <DOI:10.1063/1.1624473>.
Dan Wang et al., "Carbazole and arylamine functionalized iridium complexes for efficient electro-phosphorescent light-emitting diodes", Inorganica Chimica Acta 370 (2011) pp. 340-345.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Dong Ryun Lee et al. "Emitting Materials for Thermally Activated Delayed Fluorescent Organic Light-Emitting Diodes Using Benzofurocarbazole and Benzothienocarbazole as Donor Moieties" SID 2015 Digest, vol. 46, p. 502-504 (Year: 2015).
Dorwald; "Side Reactions in Organic Synthesis: A Guide to Successful Synthesis Design," Chapter 1, 2005 Wiley-VCH Verlag Gmbh & Co. KGaA, Wienheim, 32 pages.
Dsouza, R., et al., "Fluorescent Dyes and Their Supramolecular Host/Guest Complexes with Macrocycles in Aqueous Solution", Oct. 2011, vol. 111, No. 12, pp. 7941-7980 <DOI:10.1021/cr200213s>.
Eric Turner et al., "Cyclometalated Platinum Complexes with Luminescent Quantum Yields Approaching 100%," Inorg. Chem., 2013, vol. 52, pp. 7344-7351.
Finikova, M. A. et al., New Selective Synthesis of Substituted Tetrabenzoporphyris, Doklady Chemistry, 2003, vol. 391, No. 4-6, pp. 222-224.
Fleetham et al., "Phosphorescent Pt(II) and Pd(II) Complexes for Efficient, High-Color-Quality, and Stable OLEDs", Advanced Mater., 29, 1601861, 2017, 16 pages.
Fuchs, C. et al., "Enhanced light emission from top-emitting organic light-emitting diodes by optimizing surface plasmon polariton losses", arXiv, submitted Mar. 2015, 11 pages, arXiv:1503.01309.
Fuchs, C. et al., "Enhanced light emission from top-emitting organic light-emitting diodes by optimizing surface plasmon polariton losses", Physical Review B, Dec. 2015, vol. 92, No. 24, pp. 245306-1-245306-10 <DOI:10.1103/PhysRevB.92.245306>.
Galanin et al. Synthesis and Properties of meso-Phenyl-Substituted Tetrabenzoazaporphines Magnesium Complexes. Russian Journal of Organic Chemistry (Translation of Zhurnal Organicheskoi Khimii) (2002), 38(8), 1200-1203.
Galanin et al., meso-Phenyltetrabenzoazaporphyrins and their zinc complexes. Synthesis and spectral properties, Russian Journal of General Chemistry (2005), 75(4), 651-655.
Gather, M. et al., "Recent advances in light outcoupling from white organic light-emitting diodes," Journal of Photonics for Energy, May 2015, vol. 5, No. 1, 057607-1-057607-20 <DOI:10.1117/1.JPE.5.057607>.
Glauco Ponterini et al., "Comparison of Radiationless Decay Processes in Osmium and Platinum Porphyrins," J. Am. Chem. Soc., vol. 105, No. 14, 1983, pp. 4639-4645.
Gong et al., Highly Selective Complexation of Metal lons by the Self-Tuning Tetraazacalixpyridine macrocycles, Tetrahedron, 65(1): 87-92 (2009).
Gottumukkala, V. et al., Synthesis, cellular uptake and animal toxicity of a tetra carboranylphenyl N-tetrabenzoporphyr in, Bioorganic &Medicinal Chemistry, 2006, vol. 14, pp. 1871-1879.
Graf, A. et al., "Correlating the transition dipole moment orientation of phosphorescent emitter molecules in OLEDs with basic material

(56) References Cited

OTHER PUBLICATIONS properties", Journal of Materials Chemistry C, Oct. 2014, vol. 2, No. 48, pp. 10298-10304 <DOI:10.1039/c4tc00997e>.
Guijie Li et al., "Efficient and stable red organic light emitting devices from a tetradentate cyclometalated platinum complex," Organic Electronics, 2014, vol. 15 pp. 1862-1867.
Guijie Li et al., "Modifying Emission Spectral Bandwidth of Phosphorescent Platinum(II) Complexes Through Synthetic Control," Inorg. Chem. 2017, 56, 8244-8256.
Guijie Li et al., Efficient and Stable White Organic Light-Emitting Diodes Employing a Single Emitter, Adv. Mater., 2014, vol. 26, pp. 2931-2936.
Hansen (1969). "The universality of the solubility parameter," I & EC Product Research and Development, 8, 2-11.
Hatakeyama, T. et al., "Ultrapure Blue Thermally Activated Delayed Fluorescence Molecules: Effi cient HOMO-LUMO Separation by the Multiple Resonance Effect", Advanced Materials, Apr. 2016, vol. 28, No. 14, pp. 2777-2781, <DOI:10.1002/adma.201505491>.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.
Holmes, R. et al., "Efficient, deep-blue organic electrophosphorescence by guest charge trapping", Applied Physics Letters, Nov. 2003 [available online Oct. 2003], vol. 83, No. 18, pp. 3818-3820 <DOI:10.1063/1.1624639>.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Imre et al (1996). "Liquid-liquid demixing ffrom solutions of polystyrene. 1. A review. 2. Improved correlation with solvent properties," J. Phys. Chem. Ref. Data, 25, 637-61.
International Preliminary Report on Patentability issued on Nov. 26, 2013 for Intl. Pat. App. No. PCT/US2012/039323 filed May 24, 2012 and published as WO 2012/162488 on Nov. 29, 2012 (Applicants—Arizona Board of Regents Acting for and on Behalf of Arizona State University; Inventors—Li et al.; (7 pages).
Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.
J. Park et al., 26 Semicond. Sci. Technol., 1-9 (2011) (Year: 2011).
Jack W. Levell et al., "Carbazole/iridium dendrimer side-chain phosphorescent copolymers for efficient light emitting devices", New J. Chem., 2012, vol. 36, pp. 407-413.
Jan Kalinowski et al., "Light-emitting devices based on organometallic platinum complexes as emitters," Coordination Chemistry Reviews, vol. 255, 2011, pp. 2401-2425.
Jeong et al. (2010). "Improved efficiency of bulk heterojunction poly (3-hexylthiophene): [6,6]-phenyl-C61-butyric acid methyl ester photovoltaic devices using discotic liquid crystal additives," Appl. Phys. Lett.. 96, 183305. (3 pages).
Jeonghun Kwak et al., "Bright and Efficient Full-Color Colloidal Quantum Dot Light-Emitting Diodes Using an Inverted Device Structure," Nano Letters 12, Apr. 2, 2012, pp. 2362-2366.
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Kim et al.(2009). "Altering the thermodynamics of phase separation in inverted bulk-heterojunction organic solar cells," Adv. Mater., 21, 3110-15.
Kim et al. (2005). "Device annealing effect in organic solar cells with blends of regioregular poly(3-hexylthiophene) and soluble fullerene," Appl. Phys. Lett. 86, 063502.
Kim, HY. et al., "Crystal Organic Light-Emitting Diodes with Perfectly Oriented Non-Doped Pt-Based Emitting Layer", Advanced Functional Materials, Feb. 2016, vol. 28, No. 13, pp. 2526-2532 <DOI:10.1002/adma.201504451>.
Kim, JJ., "Setting up the new efficiency limit of OLEDs; Abstract" [online], Electrical Engineering—Princeton University, Aug. 2014 [retrieved on Aug. 24, 2016], retrieved from the internet: <URL:http://ee.princeton.edu/events/setting-new-efficiency-limit-oled> 2 pages.
Kim, SY. et al., "Organic Light-Emitting Diodes with 30% External Quantum Efficiency Based on a Horizontally Oriented Emitter", Advanced Functional Materials, Mar. 2013, vol. 23, No. 31, pp. 3896-3900 <DOI:10.1002/adfm.201300104 >.
Kroon et al. (2008). "Small bandgapolymers for organic solar cells," Polymer Reviews, 48, 531-82.
Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.
Kwong, R. et al., "High operational stability of electrophosphorescent devices", Applied Physics Letters, Jul. 2002 [available online Jun. 2002], vol. 81, No. 1, pp. 162-164 <DOI:10.1063/1.1489503>.
Lamansky, S. et al., "Cyclometalated Ir complexes in polymer organic light-emitting devices", Journal of Applied Physics, Aug. 2002 [available online Jul. 2002], vol. 92, No. 3, pp. 1570-1575 <10.1063/1.1491587>.
Lampe, T. et al., "Dependence of Phosphorescent Emitter Orientation on Deposition Technique in Doped Organic Films", Chemistry of Materials, Jan. 2016, vol. 28, pp. 712-715 <DOI:10.1021/acs.chemmater.5b04607>.
Lee et al. (2008). "Processing additives for inproved efficiency from bulk heterojunction solar cells," J. Am. Chem. Soc, 130, 3619-23.
Li et al. (2005). "Investigation of annealing effects and film thickness dependence of polymer solar cells based on poly (3-hexylthiophene)," J. Appl. Phys., 98, 043704. (5 pages).
Li et al. (2007). "Solvent annealing effect in polymer solar cells based on poly(3-hexylthiophene) and methanofullerenes," Adv. Funct. Mater, 17, 1636-44.
Li, J. et al., "Synthesis and characterization of cyclometalated Ir(III) complexes with pyrazolyl ancillary ligands", Polyhedron, Jan. 2004, vol. 23, No. 2-3, pp. 419-428 <DOI:10.1016/j.poly.2003.11.028>.
Li, J., "Efficient and Stable OLEDs Employing Square Planar Metal Complexes and Inorganic Nanoparticles", in DOE SSL R&D Workshop (Raleigh, North Carolina, 2016), Feb. 2016, 15 pages.
Li, J., et al., "Synthetic Control of Excited-State Properties in Cyclometalated Ir(III) Complexes Using Ancillary Ligands", Inorganic Chemistry, Feb. 2005, vol. 44, No. 6, pp. 1713-1727 <DOI:10.1021/ic048599h>.
Liang, et al. (2010). "For the bright future-bulk heterojunction polymer solar cells with power conversion efficiency of 7.4%," Adv. Mater. 22, E135-38.
Lin, TA et al., "Sky-Blue Organic Light Emitting Diode with 37% External Quantum Efficiency Using Thermally Activated Delayed Fluorescence from Spiroacridine-Triazine Hybrid", Advanced Materials, Aug. 2016, vol. 28, No. 32, pp. 6876-6983 <DOI:10.1002/adma.201601675>.
Machine-translated English version of JP 2012/074444 A, Sekine Noboru, Apr. 12, 2012 (Year: 2012) 75 pages.
Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.
Marc Lepeltier et al., "Efficient blue green organic light-emitting devices based on a monofluorinated heteroleptic iridium(III) complex," Synthetic Metals, vol. 199, 2015, pp. 139-146.
Markham, J. et al., "High-efficiency green phosphorescence from spin-coated single-layer dendrimer light-emitting diodes ", Applied Physics Lettersm Apr. 2002, vol. 80, vol. 15, pp. 2645-2647 <DOI:10.1063/1.1469218>.

(56) References Cited

OTHER PUBLICATIONS

Matthew J. Jurow et al., “Understanding and predicting the orientation of heteroleptic phosphors in organic light-emitting materials”, Nature Materials, vol. 15, Jan. 2016, pp. 85-93.
Michl, J., “Relationship of bonding to electronic spectra”, Accounts of Chemical Research, May 1990, vol. 23, No. 5, pp. 127-128 <DOI:10.1021/ar00173a001>.
Miller, R. et al., “Polysilane high polymers”, Chemical Reviews, Sep. 1989, vol. 89, No. 6, pp. 1359-1410 <DOI:10.1021/cr00096a006>.
Morana et al. (2007). “Organic field-effect devices as tool to characterize the bipolar transport in polymer-fullerene blends: the case of P3HT-PCBM,” Adv. Funct. Mat., 17, 3274-83.
Moule et al. (2008). “Controlling morphology in Polymer-Fullerene mixtures,” Adv. Mater., 20, 240-45.
Murakami; JP 2007324309, English machine translation from EPO, dated Dec. 13, 2007, 89 pages.
Myoung-Seon Gong et al. “Synthesis and device properties of mCP analogues based on fused-ring carbazole moiety”, Org. Electronics, 2017, vol. 42, p. 66-74 (Year: 2017).
Nazeeruddin, M. et al., “Highly Phosphorescence Iridium Complexes and Their Application in Organic Light-Emitting Devices”, Journal of the American Chemical Society, Jun. 2003, vol. 125, No. 29, pp. 8790-8797 <DOI:10.1021/ja021413y>.
Nicholas R. Evans et al., “Triplet Energy Back Transfer in Conjugated Polymers with Pendant Phosphorescent Iridium Complexes,” J. Am. Chem. Soc., vol. 128, 2006, pp. 6647-6656.
Nillson et al. (2007). “Morphology and phase segregation of spin-casted films of polyfluorene/PCBM Blends,” Macromolecules, 40, 8291-8301.
Olynick et al. (2009). “The link between nanoscale feature development in a negative resist and the Hansen solubility sphere,” Journal of Polymer Science: Part B: Polymer Physics, 47, 2091-2105.
Peet et al. (2007). “Efficiency enhancement in low-bandgap polymer solar cells by processing with alkane dithiols,” Nature Materials, 6, 497-500.
Pivrikas et al. (2008). “Substituting the postproduction treatment for bulk-heterojunction solar cells using chemical additives,” Organic Electronics, 9, 775-82.
Pui Keong Chow et al., “Strongly Phosphorescent Palladium(II) Complexes of Tetradentate Ligands with Mixed Oxygen, Carbon, and Nitrogen Donor Atoms: Photophysics, Photochemistry, and Applications,” Angew. Chem. Int. Ed. 2013, 52, 11775-11779.
Z Liu et al., “Green and blue-green phosphorescent heteroleptic iridium complexes containing carbazole-functionalized beta-diketonate for non-doped organic light-emitting diodes”, Organic Electronics 9 (2008) pp. 171-182.
Z Xu et al., “Synthesis and properties of iridium complexes based 1,3,4-oxadiazoles derivatives”, Tetrahedron 64 (2008) pp. 1860-1867.
Zhi-Qiang Zhu et al., “Efficient Cyclometalated Platinum(II) Complex with Superior Operational Stability,” Adv. Mater. 29 (2017) 1605002, pp. 1-5.
Zhi-Qiang Zhu et.al., “Harvesting All Electrogenerated Excitons through Metal Assisted Delayed Fluorescent Materials,” Adv. Mater. 27 (2015) 2533-2537.
Zhu, W. et al., “Highly efficient electrophosphorescent devices based on conjugated polymers doped with iridium complexes”, Applied Physics Letters, Mar. 2002, vol. 80, No. 12, pp. 2045-2047 <DOI:10.1063/1.1461418>.

* cited by examiner

NON-PLATINUM METAL COMPLEXES FOR EXCIMER BASED SINGLE DOPANT WHITE ORGANIC LIGHT EMITTING DIODES

CROSS-REFERENCE TO RELATED APPLICATION

This application is a continuation of U.S. patent application Ser. No. 17/019,817, filed Sep. 14, 2020, now allowed, which is a continuation of U.S. patent application Ser. No. 15/503,690, filed Feb. 13, 2017, now U.S. Pat. No. 10,793, 546, which is a 35 U.S.C. § 371 national phase application from, and claiming priority to, International Application PCT/US2015/045416, filed Aug. 14, 2015, which claims priority to U.S. Provisional Patent Application No. 62/037, 802, filed Aug. 15, 2014, all of which are incorporated by reference herein in their entireties.

STATEMENT OF GOVERNMENT INTEREST

This invention was made with government support under DE-EE0005075 awarded by the Department of Energy. The government has certain rights in the invention.

TECHNICAL FIELD

This disclosure relates to non-platinum metal complexes for excimer based single dopant white organic light emitting diodes (OLEDs).

BACKGROUND

Cyclometalated metal complexes can be used for many applications including the development of efficient and high quality organic white lighting devices. One route for achieving organic white lighting devices is development of singly doped white OLEDs by utilizing the excimer properties. Typically the metal complexes used as emissive materials are square-planar platinum complexes.

White organic light emitting diodes (WOLEDs) have shown promise as a potential replacement for existing lighting technologies due to their efficiencies exceeding 100 Lm/W, potential for low cost and scalable production, and compatibility with flexible substrates. Through continuous improvements in device designs and by employing phosphorescent iridium or platinum emitters, WOLEDs with high efficiencies and high color quality have been achieved.

Nevertheless, major challenges still remain, including the deficiency of an efficient and stable phosphorescent blue emitter and the cost prohibitive nature of typical multilayer WOLED structures. The low stability of these devices may be related to the use of blue phosphorescent materials which frequently adopt molecular structures including fluorine groups or 5-membered heterocycles. Complexes cyclometalated with these type of ligands have typically been less stable than iridium complexes cyclometalated with phenylpyridine and their analogs, which are known stable and efficient green and red phosphorescent emitters and have been incorporated into commercially viable device settings. Furthermore, the relatively complex multilayer structure typically used in high performance WOLEDs may complicate the goal of low cost fabrication. White devices employing a single emissive platinum complex can achieve emission spanning the visible spectrum while also achieving high efficiencies by utilizing phosphorescent excimers. However, these devices face the same operational lifetime challenges as blue phosphorescent emitters, and platinum and iridium complexes have been unable to yield a WOLED fabricated using a single emissive material with sufficient blue emission, efficient excimer emission, and a molecular design aligned with known stable emitters. For example, while symmetric platinum complexes offer both the rigidity and planar geometry typically necessary for white emission, low operational lifetimes can result from phenyl-azole cyclometalating ligands (e.g., phenyl-azole) and unsuitable device architecture. Moreover, palladium complexes have typically been non emissive or weakly emissive due to at least in part to their low radiative decay rates and low lying metal-centered states providing non-radiative decay pathways, and have not demonstrated efficient excimer emission.

SUMMARY

This disclosure describes the use of non-platinum metal complexes (e.g., palladium, gold, iridium, and rhodium complexes) with efficient excimer emission to provide emitters for white light emitting device applications. The molecular structure of four-coordinating ligands afford the electrochemical and photophysical stability of metal complexes.

In one aspect, disclosed herein is a compound of General Formula I:

General Formula I

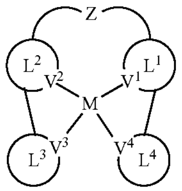

wherein:

M is $Pd^{2+}$, $Ir^{+}$, $Rh^{+}$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

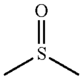 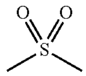 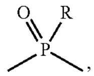, or 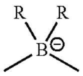, where each R is independently substituted or unsubstituted $C_1$-$C_4$ alkyl or substituted or unsubstituted aryl.

In some implementations, at least one of $V^1$, $V^2$, $V^3$, and $V^4$ is C.

Particular embodiments are described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
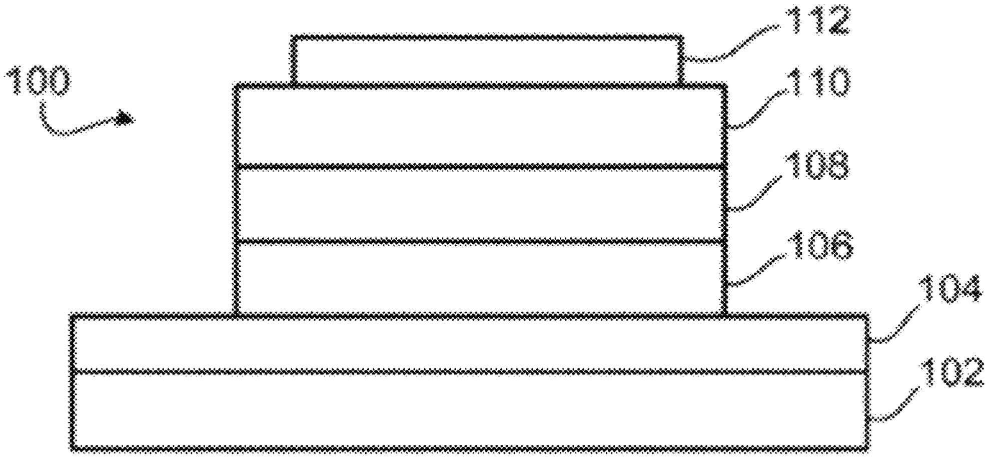
FIG. 1 depicts a cross-sectional view of an exemplary organic light emitting device (OLED).

The present disclosure can be understood more readily by reference to the following detailed description and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of compounds of the present disclosure, example methods and materials are now described.

As used in the specification and the appended claims, the singular forms “a”, “an”, and “the” include plural referents unless the context clearly dictates otherwise. Thus, for example, reference to “a component” includes mixtures of two or more components.

As used herein, the terms “optional” or “optionally” means that the subsequently described event or circumstance can or cannot occur, and that the description includes instances where said event or circumstance occurs and instances where it does not.

Disclosed are the components to be used to prepare the compositions of this disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions disclosed herein. Thus, if there are a variety of additional steps that can be performed it is understood that each of these additional steps can be performed with any specific embodiment or combination of embodiments of the methods described herein.

As referred to herein, a linking atom or group connects two atoms such as, for example, an N atom and a C atom. A linking atom or group is in one aspect disclosed as $L^1$, $L^2$, $L^3$, etc. herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include amine, amide, thiol, aryl, heteroaryl, cycloalkyl, and heterocyclyl moieties. The term “cyclic structure” or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term “substituted” is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms “substitution” or “substituted with” include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, “$A^1$”, “$A^2$”, “$A^3$”, “$A^4$” and “$A^5$” are used herein as generic symbols to represent various specific substituents. These symbols can be any substituent, not limited to those disclosed herein, and when they are defined to be certain substituents in one instance, they can, in another instance, be defined as some other substituents.

The term “alkyl” as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus.

Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $—OC(O)A^1$ or $—C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)_a—$ or $-(A^1O(O)C\text{-}A^2\text{-}OC(O))_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "polymeric" includes polyalkylene, polyether, polyester, and other groups with repeating units, such as, but not limited to $—(CH_2O)_n—CH_3$, $—(CH_2CH_2O)_n—CH_3$, $—[CH_2CH(CH_3)]_n—CH_3$, $—[CH_2CH(COOCH_3)]_n—CH_3$, $—[CH_2CH(COO\ CH_2CH_3)]_n—CH_3$, and $—[CH_2CH(COO^tBu)]_n—CH_3$, where n is an integer (e.g., n>1 or n>2).

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula $—N_3$.

The term "nitro" as used herein is represented by the formula $—NO_2$.

The term "nitrile" as used herein is represented by the formula-CN.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase “an alkyl group comprising an amino group,” the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein may contain “optionally substituted” moieties. In general, the term “substituted,” whether preceded by the term “optionally” or not, means that one or more hydrogens of the designated moiety are replaced with a suitable substituent. Unless otherwise indicated, an “optionally substituted” group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

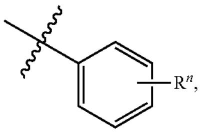

which is understood to be equivalent to a formula:

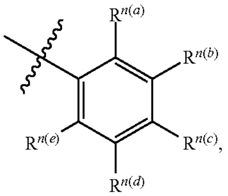

wherein n is typically an integer. That is, $R^n$ is understood to represent up to five independent non-hydrogen substituents, $R^{n(a)}$, $R^{n(b)}$, $R^{n(c)}$, $R^{n(d)}$, $R^{n(e)}$. By “independent substituents,” it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

In one aspect, disclosed herein is a compound of General Formula I:

General Formula I

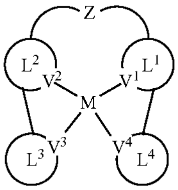

wherein:

M is $Pd^{2+}$, $Ir^+$, $Rh^+$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene; and Z is O, S, NR, $CR_2$, $SiR_2$, BR, PR,

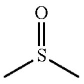 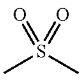 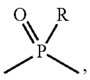, or 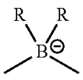, where each R is independently substituted or unsubstituted $C_1$-$C_4$ alkyl or substituted or unsubstituted aryl.

In some implementations, at least one of $V^1$, $V^2$, $V^3$, and $V^4$ is C.

As described herein, General Formula I includes Formulas A1-A20, B1-B8, and C1-C20. For each of these Formulas, unless otherwise noted, when present, M, $V^1$, $V^2$, $V^3$, $V^4$, and Z are as defined above with respect to General Formula I;

each $R^1$, $R^2$, $R^3$, and $R^4$ present represents a non-hydrogen substituent and is independently substituted or unsubstituted $C_1$-$C_4$ alkyl or substituted or unsubstituted aryl; each n is independently an integer of 0 to the maximum value permitted by valency (e.g., 3, 4, 5);

each Y present (e.g., $Y^{1a}$, $Y^{2a}$, $Y^{1b}$, $Y^{2b}$, $Y^{3a}$, $Y^{3b}$, $Y^{4a}$, and $Y^{4b}$) is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl;

U is O, S, NR, PR, AsR, $CR_2$, $SiR_2$, or BR, where each R is hydrogen, halogen, alkyl, alkenyl, alkynyl, and aryl; and X indicates the larger ring structure.

For compounds of Formulas A1-A20, M is $Pd^{2+}$. For compounds of Formulas A13-A20, Z is

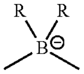.

Compounds of Formula A1 have the following structure:

Formula A1

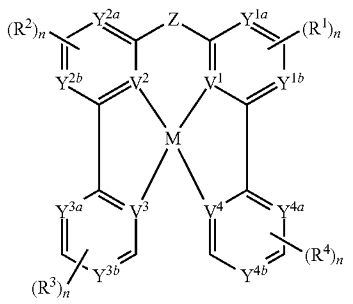

Compounds of Formula A2 have the following structure:

Formula A2

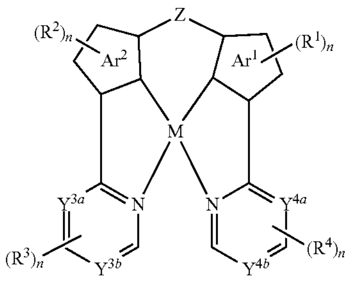

wherein:

each

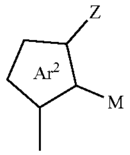 and 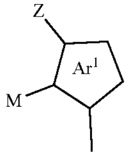

is independently selected from the group consisting of:

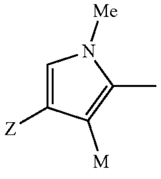 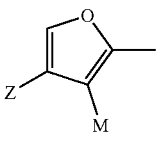 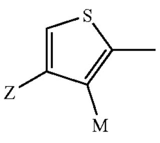

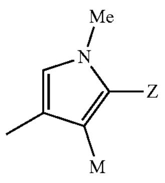 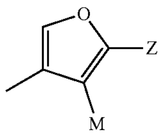 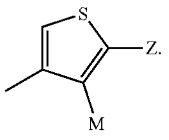

Compounds of Formula $A^3$ have the following structure:

Formula A3

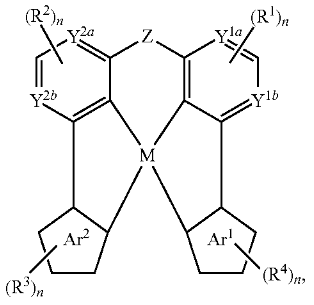

wherein each

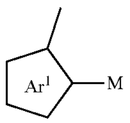 and 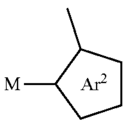

is independently selected from the group consisting of

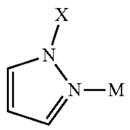 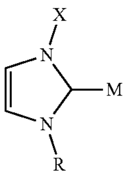 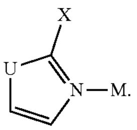

Compounds of Formulas A4-A6 have the following structures:

Formula A4

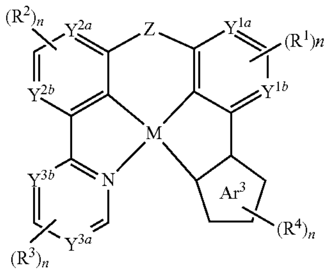

Formula A5

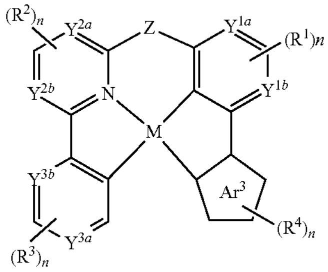

-continued
Formula A6
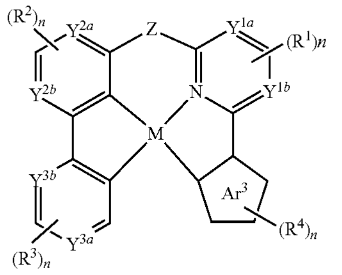
wherein
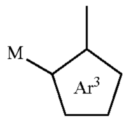
is selected from the group consisting of
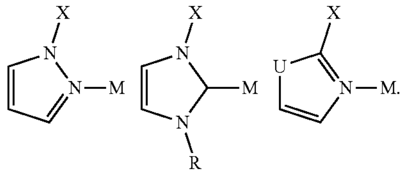
Compounds of Formulas A7-A8 have the following structures:
Formula A7
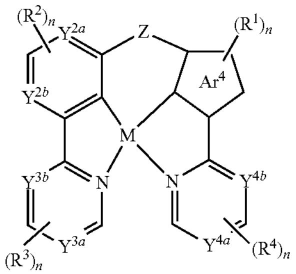
Formula A8
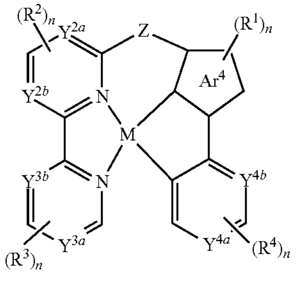
-continued
Formula A9
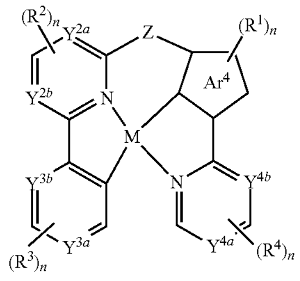
wherein
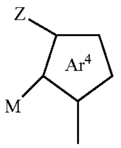
is selected from the group consisting of
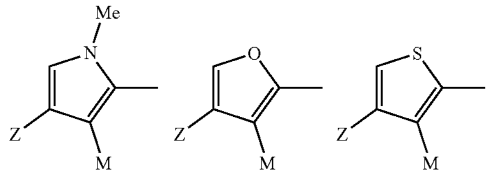
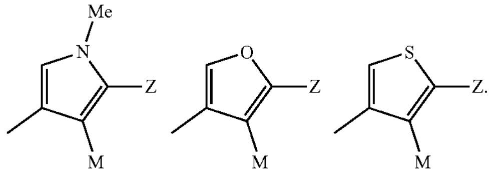
Compounds of Formulas A10 and A11 have the following structures:
Formula A10
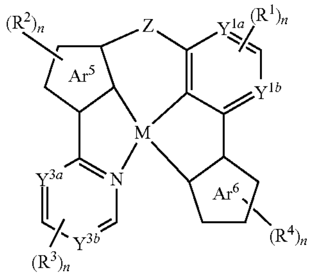

-continued
Formula A11
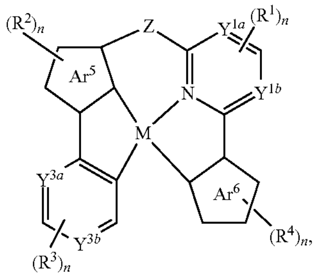
wherein
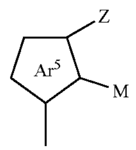
is selected from the group consisting of
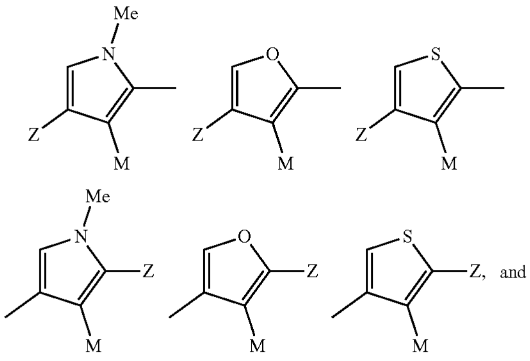
and
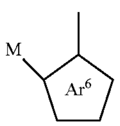
is selected from the group consisting of
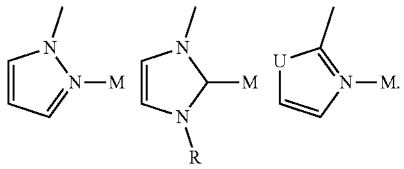
Compounds of Formula A12 have the following structure:
Formula A12
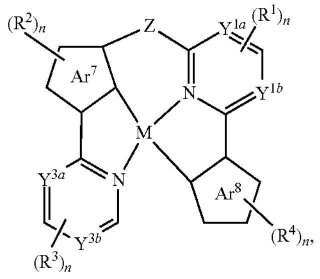
wherein
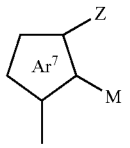
is selected from the group consisting of
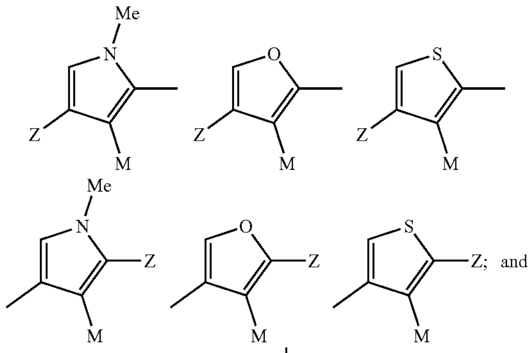
and
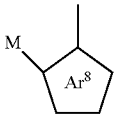
is selected from the group consisting of
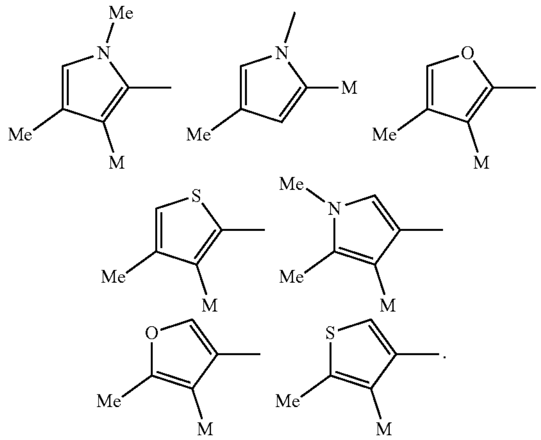

As noted above, for Formulas A13-A20. Z is

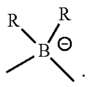

Compounds of Formula A13 have the following structure:

Formula A13

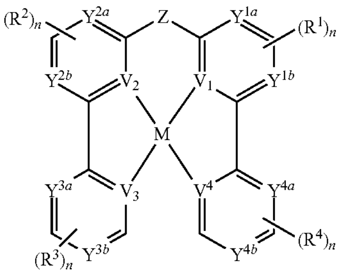

Compounds of Formula A14 have the following structure:

Formula A14

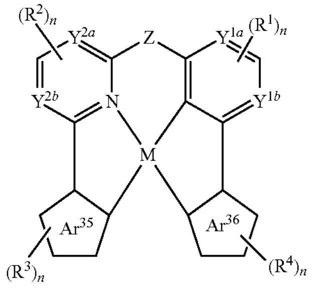

wherein each

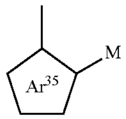 and 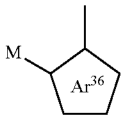

is independently selected from the group consisting of

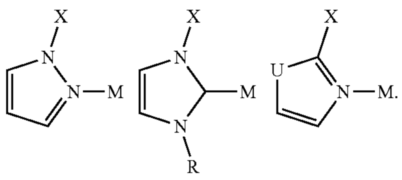

Compounds of Formulas A15-A17 have the following structures:

Formula A15

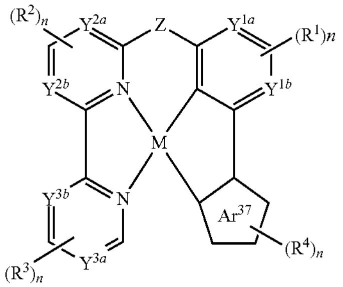

Formula A16

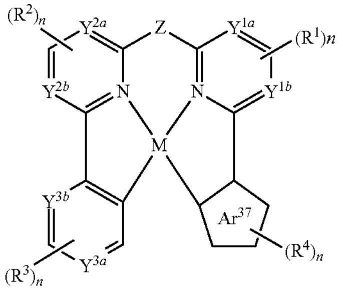

Formula A17

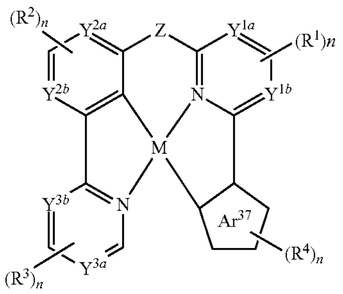

wherein

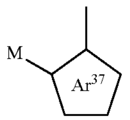

is selected from the group consisting of

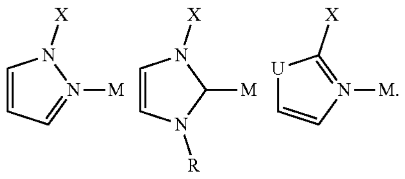

Compounds of Formula A18 have the following structure:
Formula A18
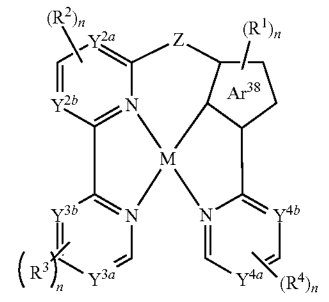
wherein
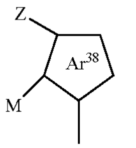
is selected from the group consisting of
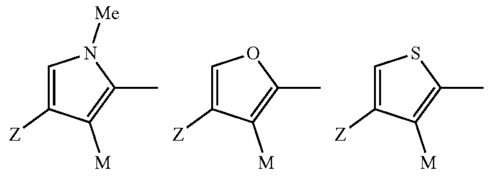
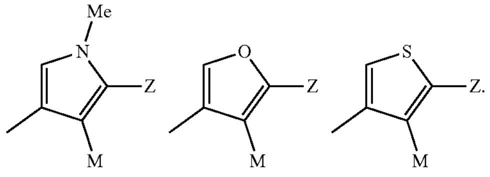
Compounds of Formula A19 have the following structure:
Formula A19
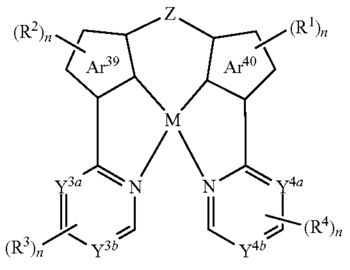
wherein
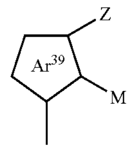
is selected from the group consisting of
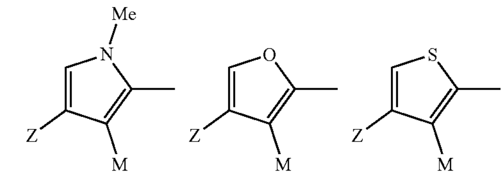
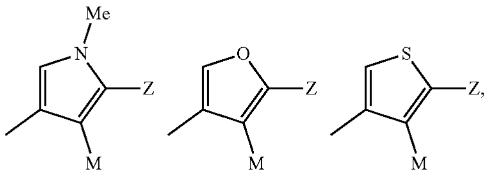 and
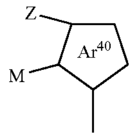
is selected from the group consisting of
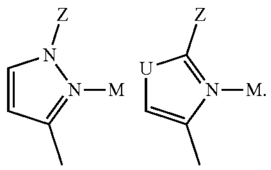
Compounds of Formula A20 have the following structure:
Formula A20
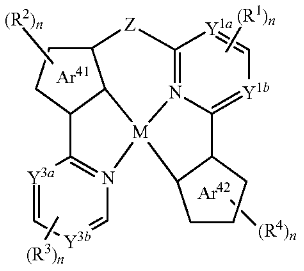

wherein
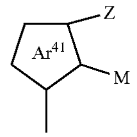
is selected from the group consisting of
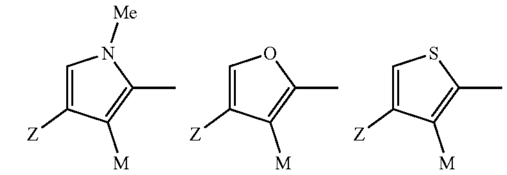
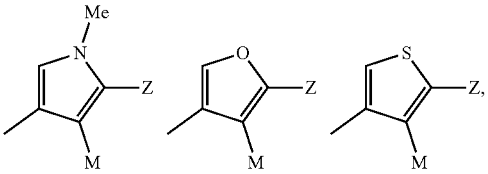
and
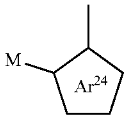
is selected from the group consisting of
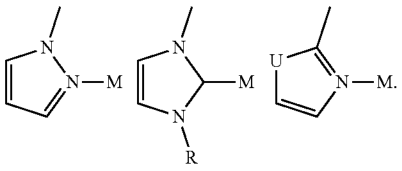
In compounds of Formulas B1-B8. M is $Ir^+$ or $Rh^+$.
Compounds of Formula B1 have the following structure:
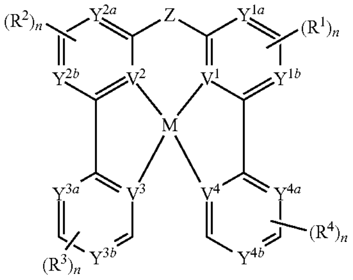
Formula B1
Compounds of Formulas B2-B4 have the following structures:
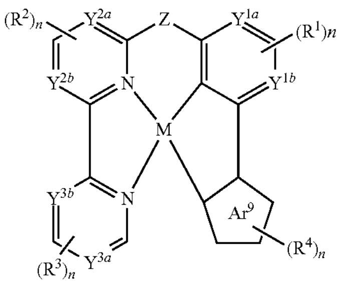
Formula B2
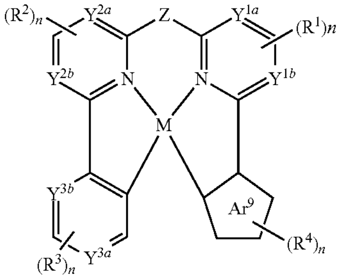
Formula B3
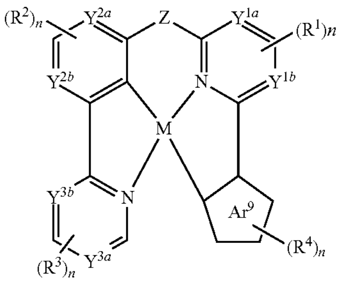
Formula B4
wherein
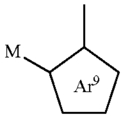
is selected from the group consisting of
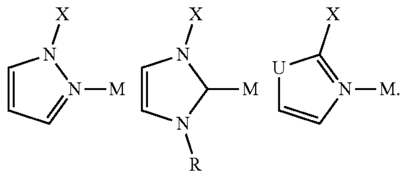

Compounds of Formula B5 have the following structure:

Formula B5

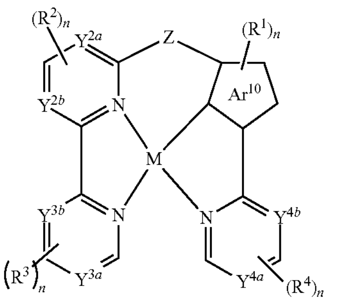

wherein

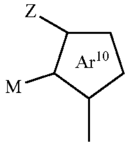

is selected from the group consisting of

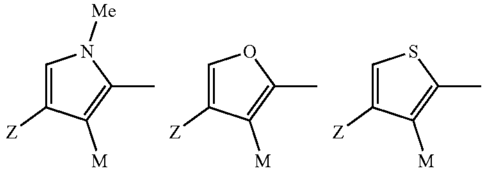

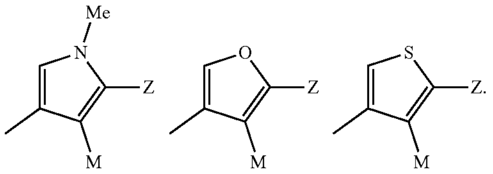

Compounds of Formula B6 have the following structure:

Formula B6

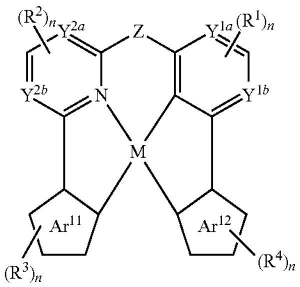

wherein each

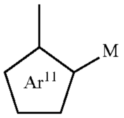

and

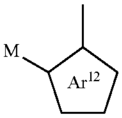

is independently selected from the group consisting of

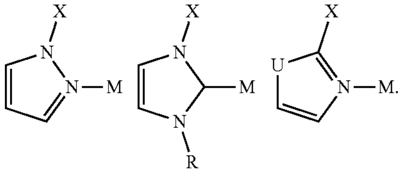

Compounds of Formula B7 have the following structure:

Formula B7

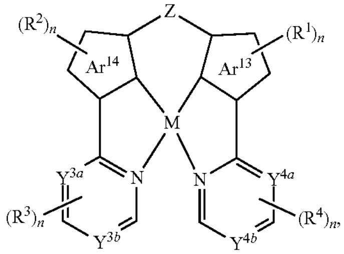

wherein

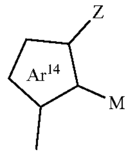

is selected from the group consisting of

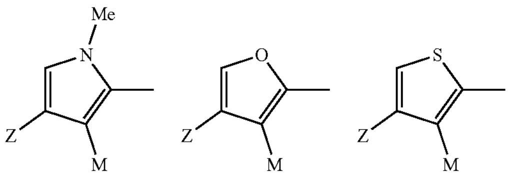

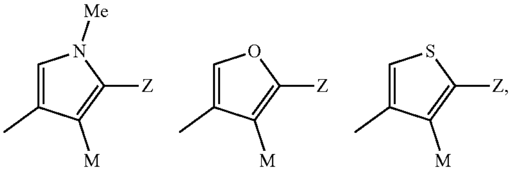

and

-continued

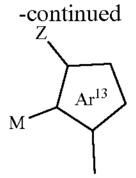

is selected from the group consisting of

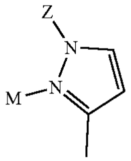 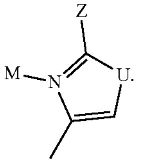

Compounds of Formula B8 have the following structure:

Formula B8

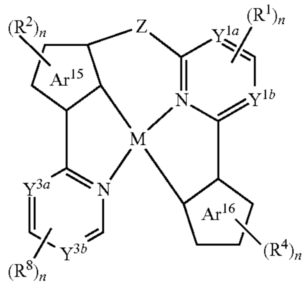

wherein

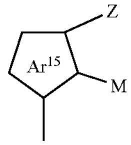

is selected from the group consisting of:

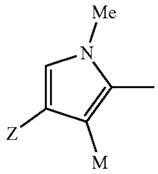 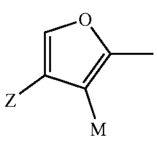 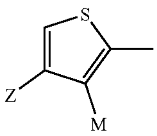

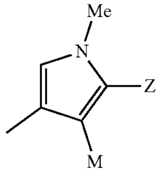 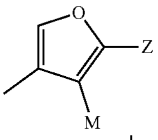 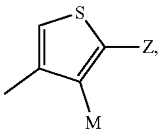 and

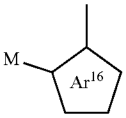

is selected from the group consisting of:

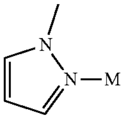 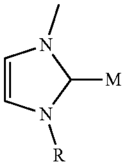 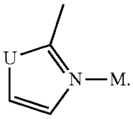

In compounds of Formulas C1-C20. M is $Au^{3+}$. For Formulas C9-C20, Z is

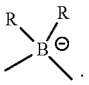

Compounds of Formula C1 have the following structure:

Formula C1

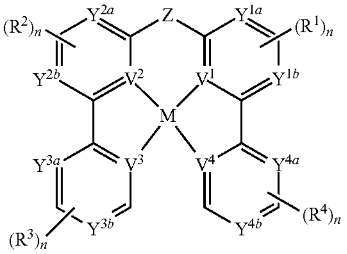

Compounds of Formula C2 have the following structure:

Formula C2

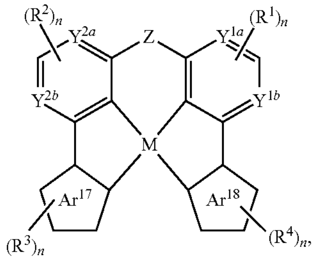

wherein

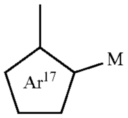

is selected from the group consisting of:

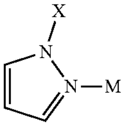 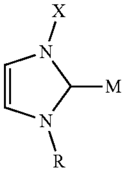 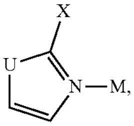

wherein
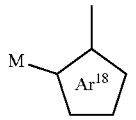
is selected from the group consisting of:
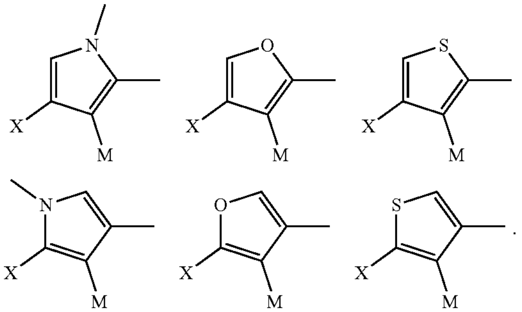
Compounds of Formula C3 have the following structure:
Formula C3
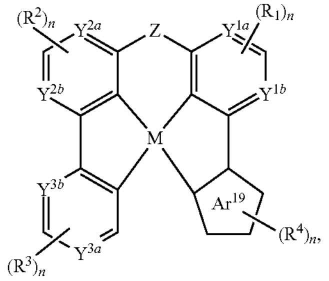
wherein
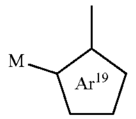
is selected from the group consisting of
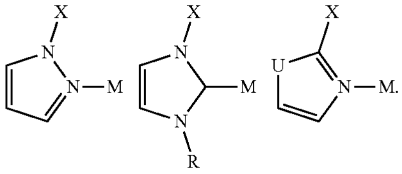
Compounds of Formulas C4-C6 have the following structures:
Formula C4
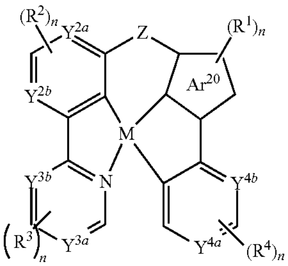
Formula C5
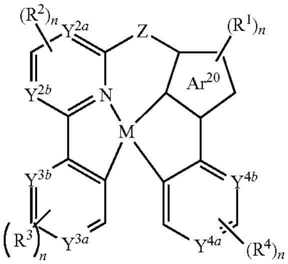
Formula C6
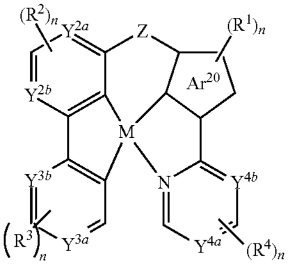
wherein
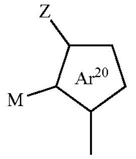
is selected from the group consisting of
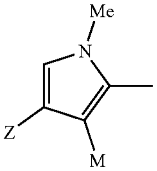
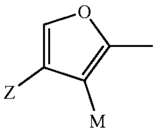

-continued
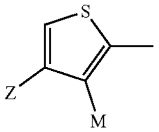
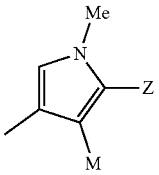
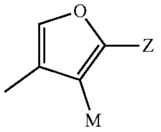
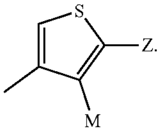
Compounds of Formula C7 have the following structure:
Formula C7
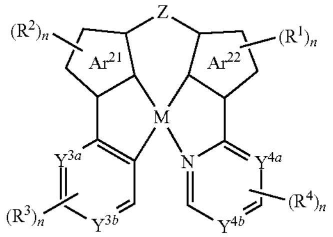
wherein each of
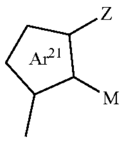
and
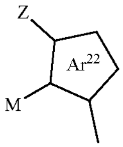
is independently selected from the group consisting of
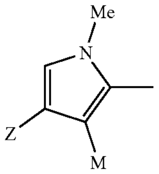
-continued
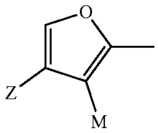
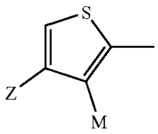
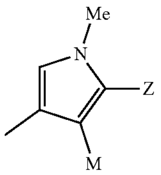
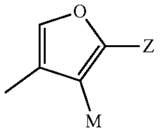
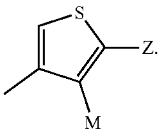
Compounds of Formula C8 have the following structure:
Formula C8
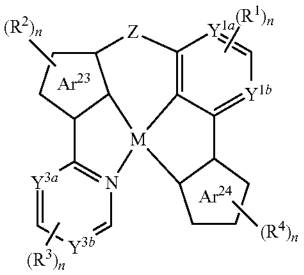
wherein
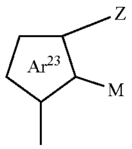
is selected from the group consisting of
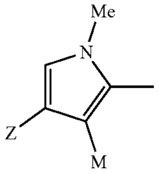

-continued
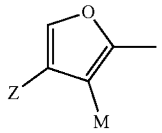
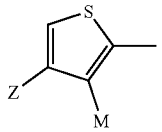
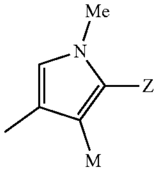
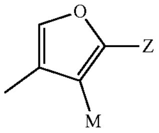
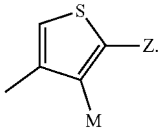
wherein
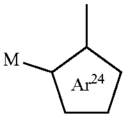
is selected from the group consisting of
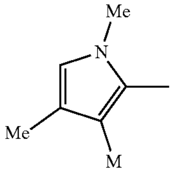
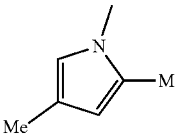
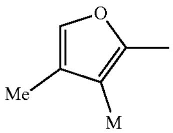
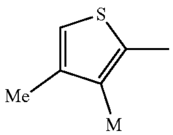
-continued
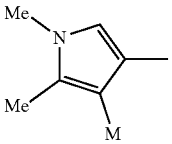
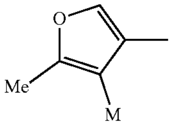
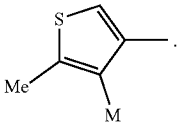
As noted above, for Formulas C9-C20, Z is
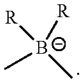
Compounds of Formula C9 have the following structure:
Formula C9
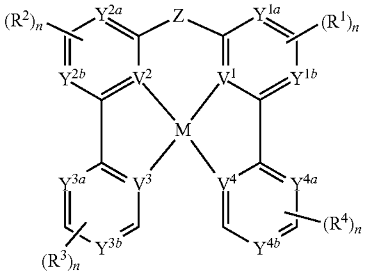
Compounds of Formula C10 have the following structure:
Compound C10
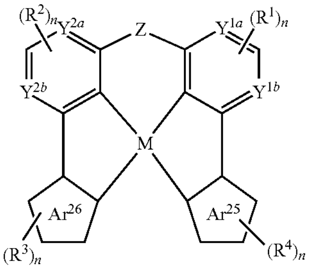
wherein each
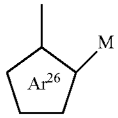
and -continued
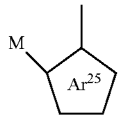
is independently selected from the group consisting of
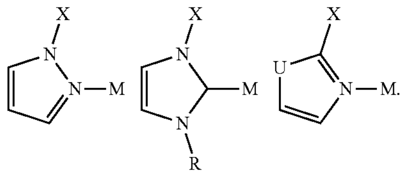
Compounds of Formulas C11-C13 have the following structures:
Formula C11
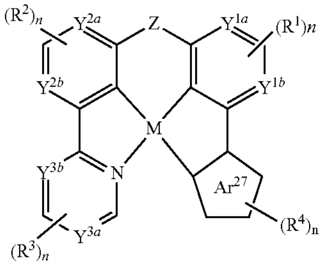
Formula C12
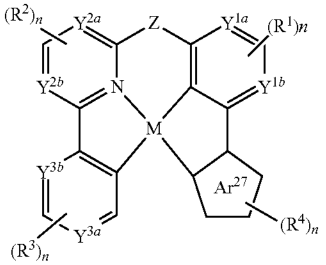
Formula C13
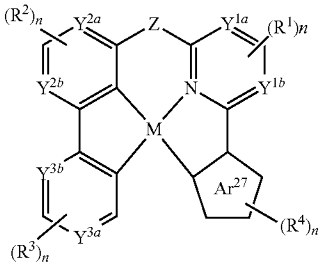
wherein
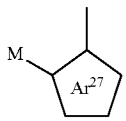
is selected from the group consisting of
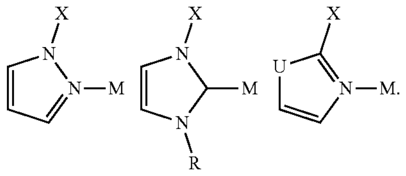
Compounds of Formulas C13-C15 have the following structures:
Formula C13
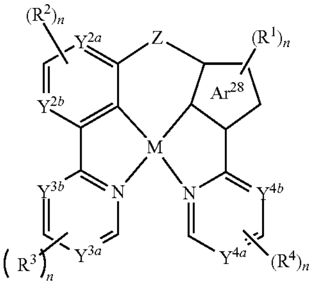
Formula C14
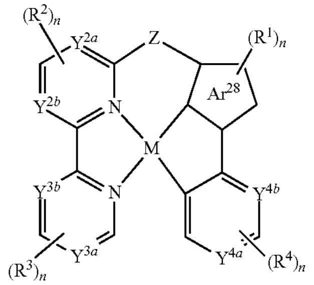
Formula C15
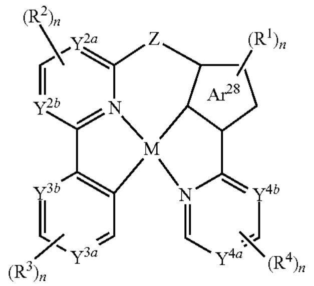
wherein
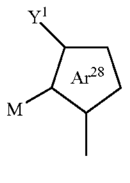

is selected from the group consisting of
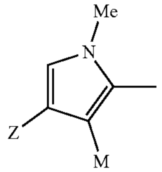
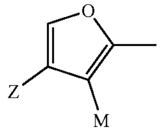
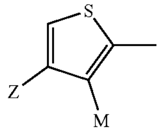
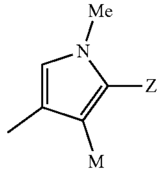
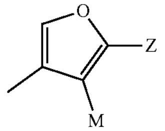
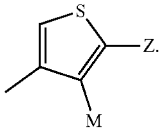
Compounds of Formula C16 have the following structure:
Formula C16
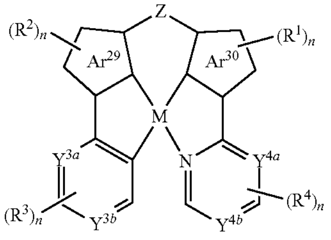
wherein each
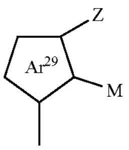
and
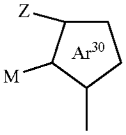
is independently selected from the group consisting of
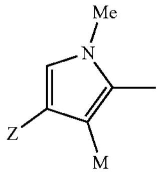
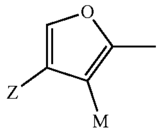
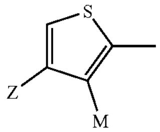
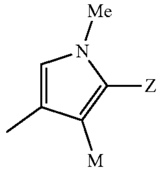
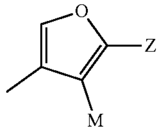
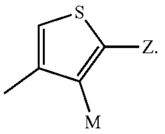
Compounds of Formulas C17 and C18 have the following structures:
Formula C17
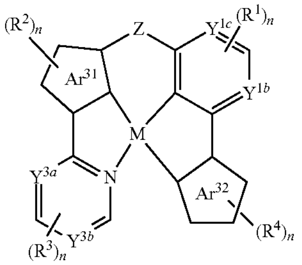
Formula C18
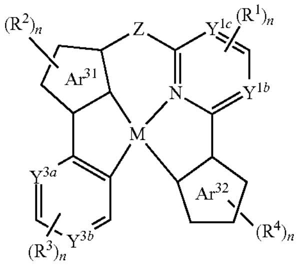

wherein
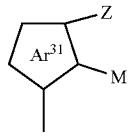
is selected from the group consisting of
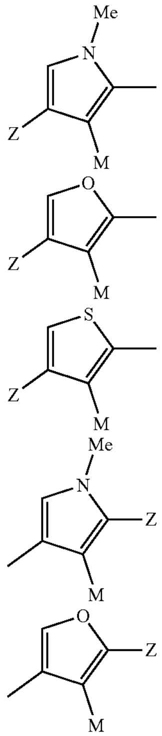
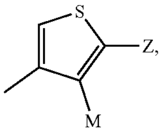
and
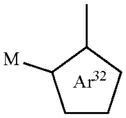
is selected from the group consisting of
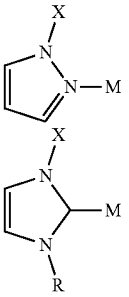
-continued
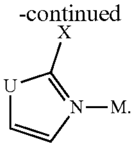
Compounds of Formula C19 have the following structure:
Formula C19
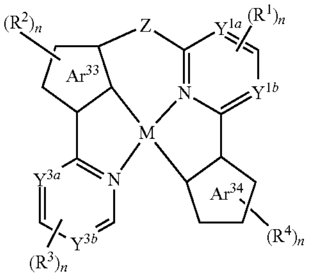
wherein
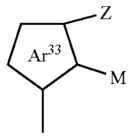
is selected from the group consisting of
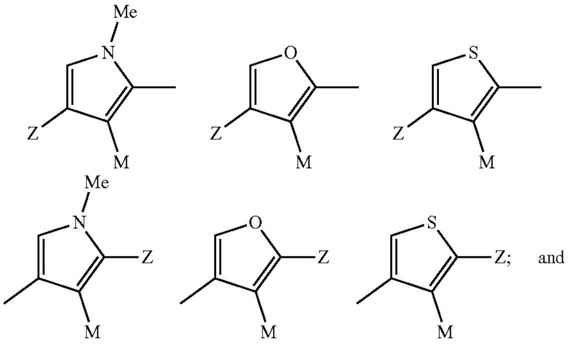
and
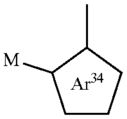
is selected from the group consisting of
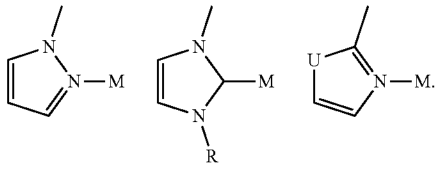

A compound of General Formula I may have one of the following structures:
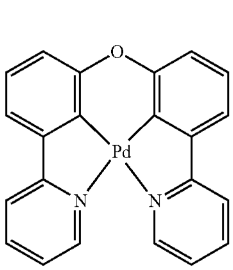
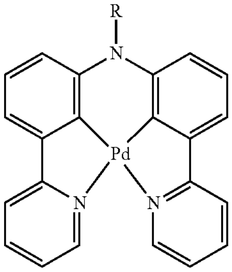
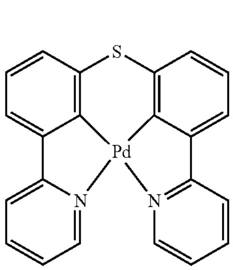
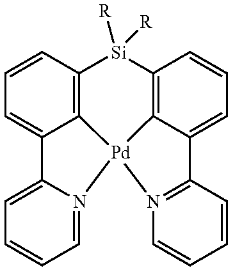
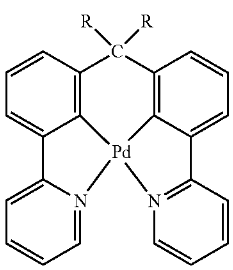
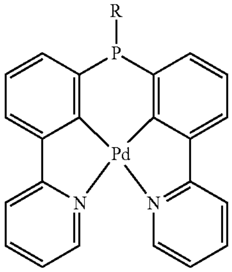
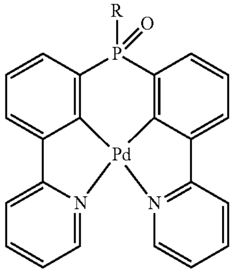
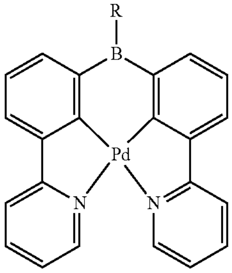
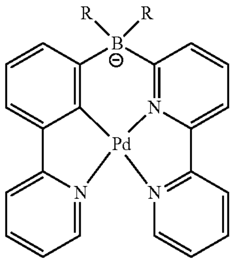
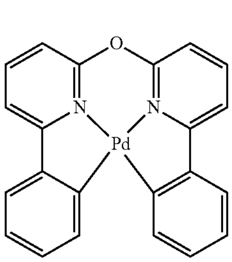
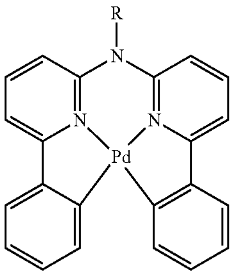
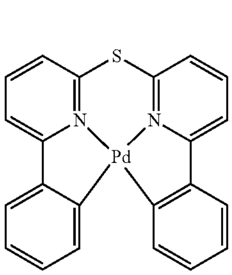
-continued
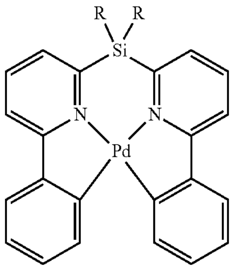
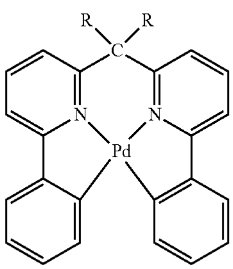
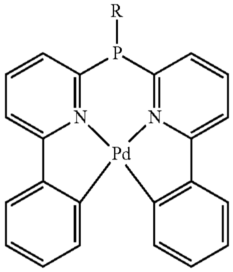
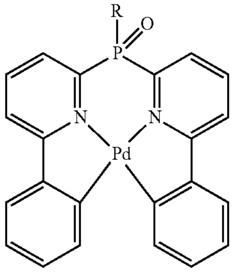
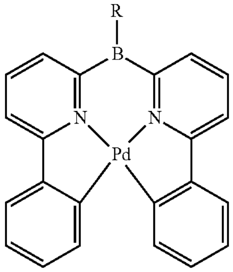
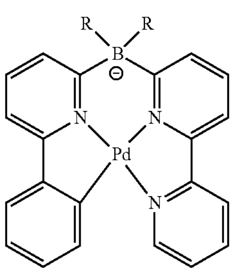
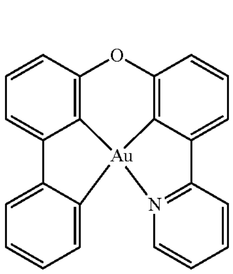
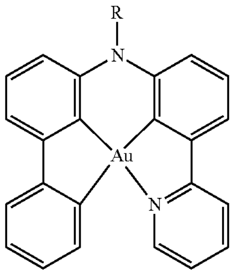
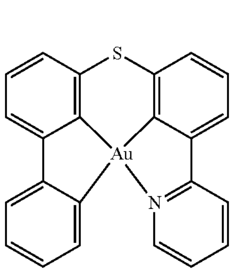
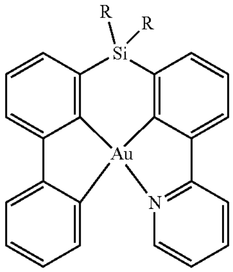
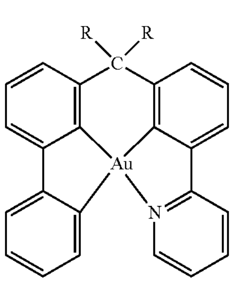
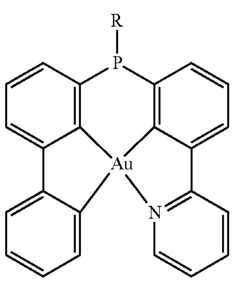

-continued
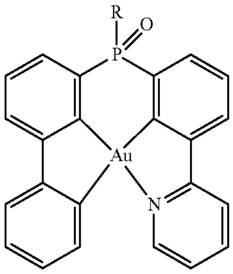
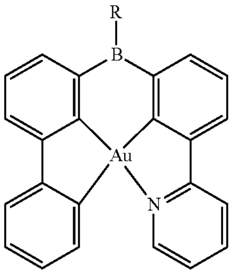
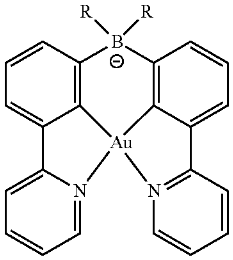
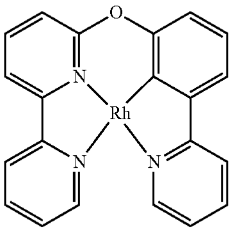
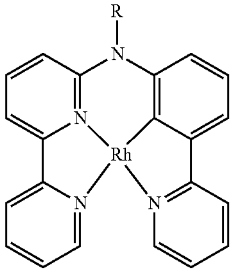
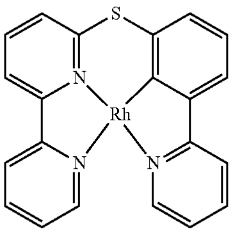
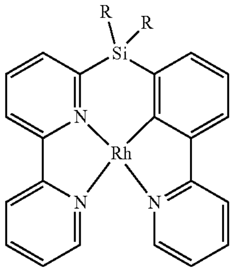
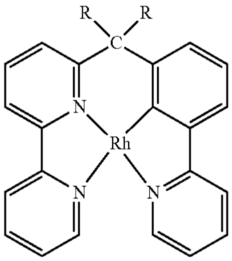
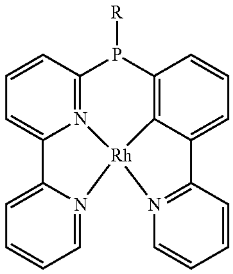
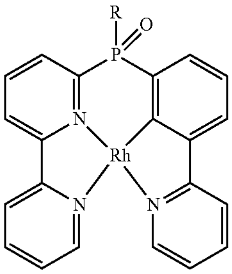
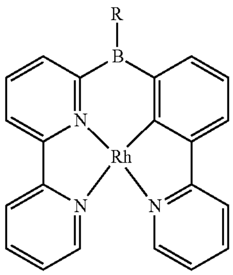
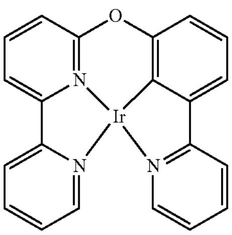
-continued
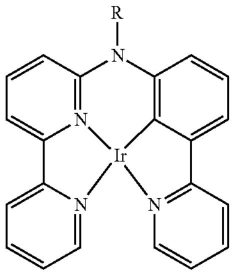
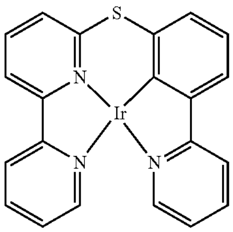
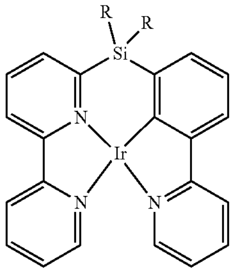
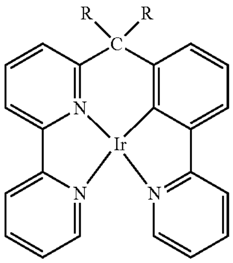
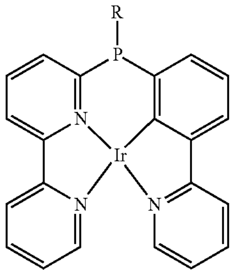
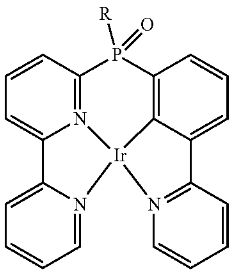
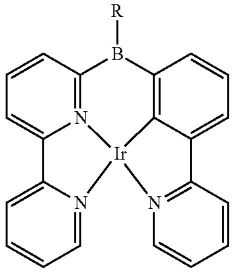
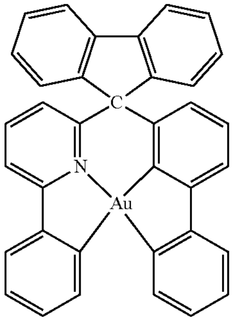
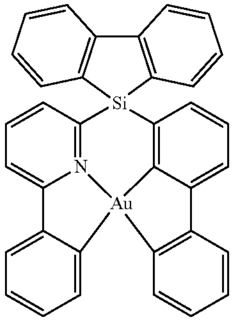
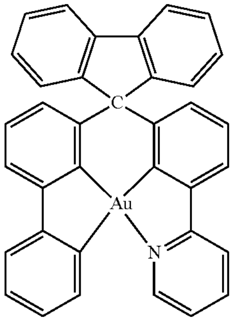

-continued
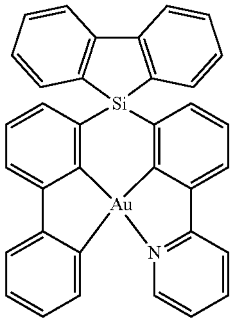
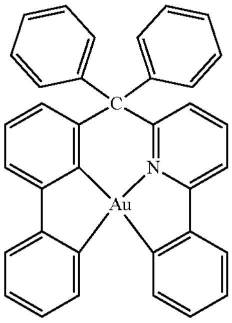
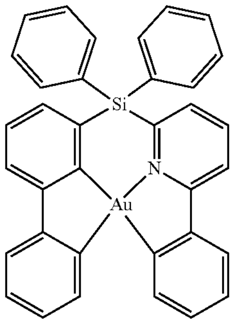
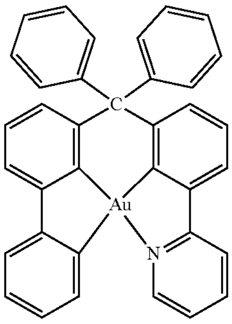
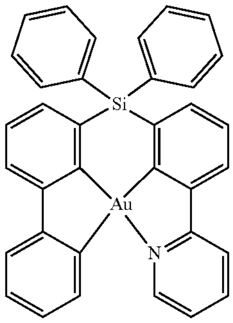
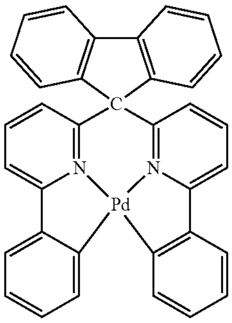
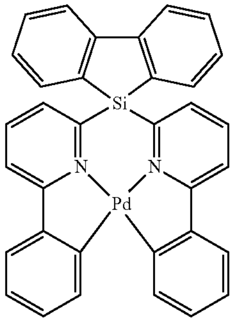
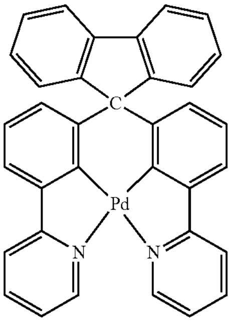
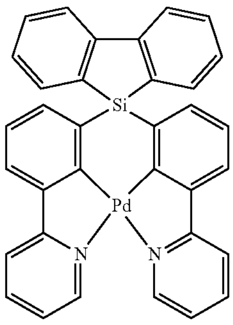
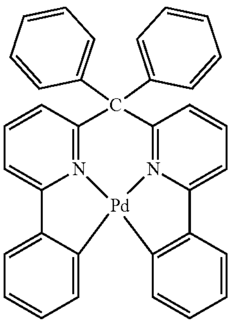
-continued
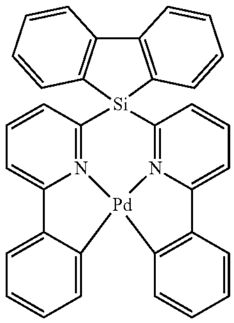
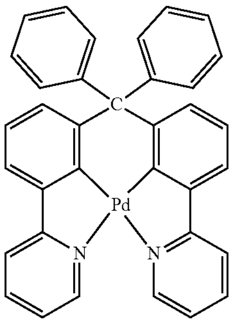
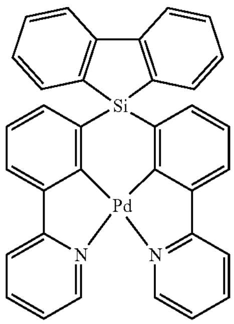
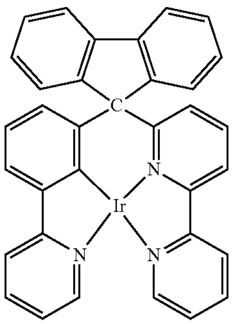
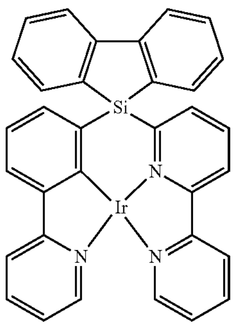
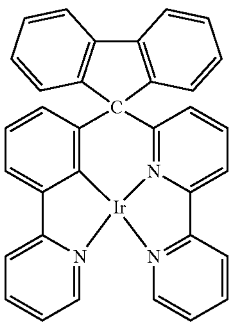
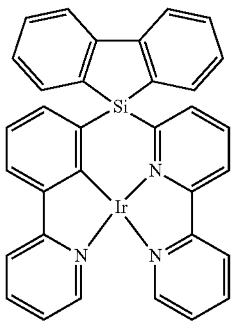
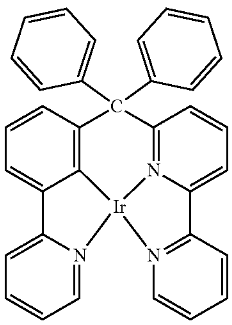
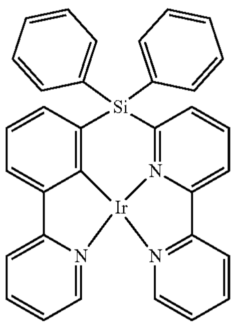
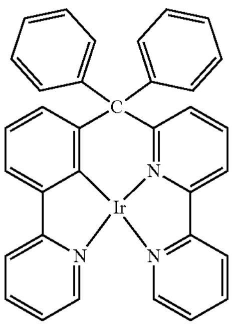

-continued

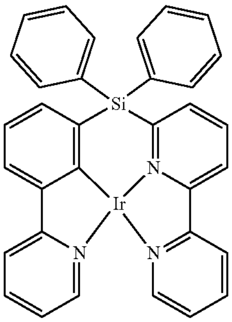

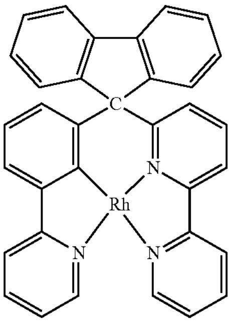

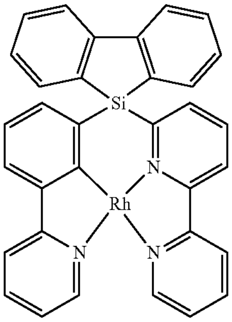

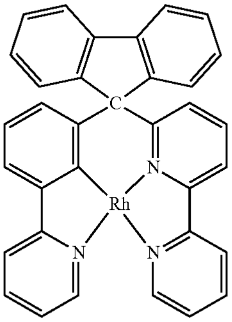

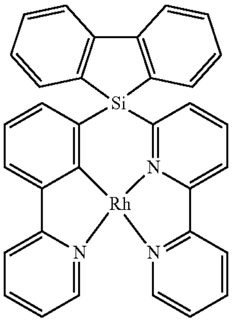

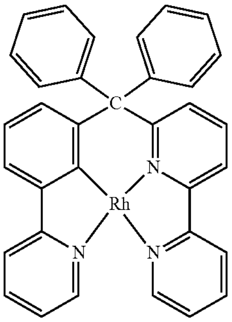

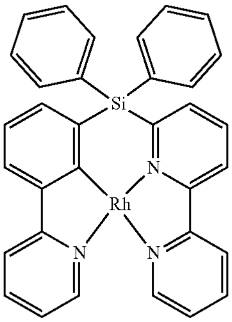

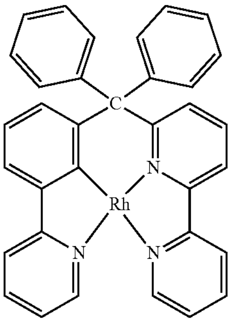

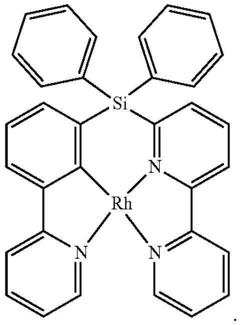

.

As described herein, General Formula I includes General Formulas 1-5. For each of these General Formulas, unless otherwise noted, when present.

M, $V^1$, $V^2$, $V^3$, $V^4$, and Z are as defined above with respect to General Formula I;

each $R^1$, $R^2$, $R^3$, and $R^4$ present represents a non-hydrogen substituent and is independently substituted or unsubstituted $C_1$-$C_4$ alkyl or substituted or unsubstituted aryl;

each n is independently an integer of 0 to the maximum value permitted by valency (e.g., 3, 4, 5); and each Y present (e.g., $Y^{1a}$, $Y^{2a}$, $Y^{1b}$, $Y^{2b}$, $Y^{3a}$, $Y^{3b}$, $Y^{4a}$, $Y^{4b}$, etc.) is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl.

Compounds of General Formula 1 have the following structure:

General Formula 1

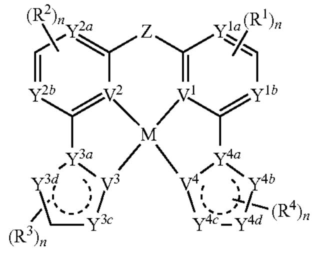

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 3, valency permitting; and each of $Y^{1a}$, $Y^{2a}$, $Y^{1b}$, $Y^{2b}$, $Y^{3a}$, $Y^{3c}$, $Y^{3d}$, $Y^{4a}$, $Y^{4b}$, $Y^{4c}$, $Y^{4d}$ is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl.

A compound of General Formula 1 may have one of the following structures:

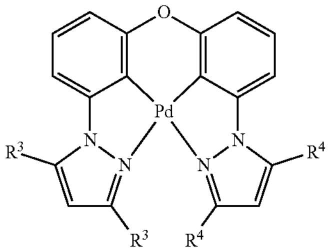

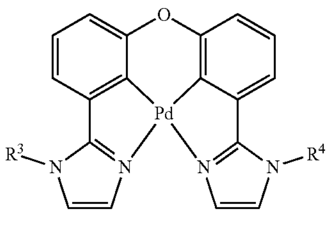

-continued
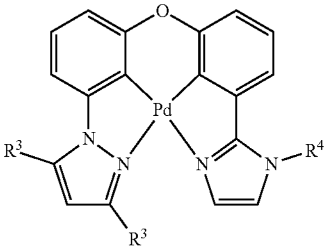
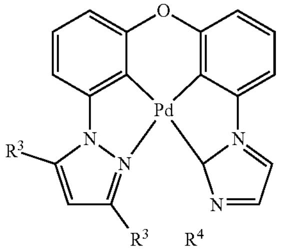
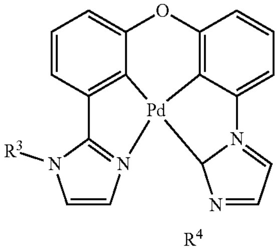
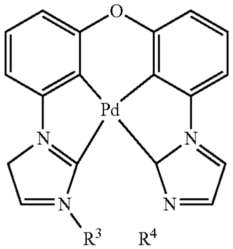
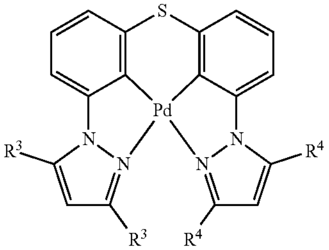
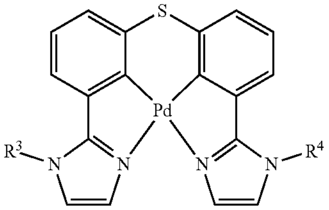
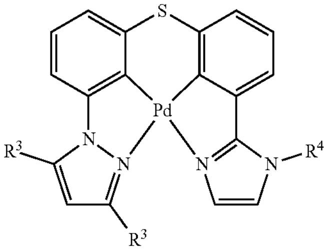
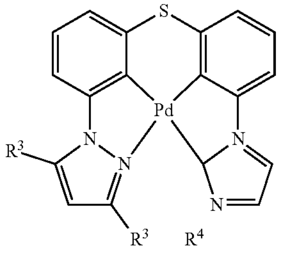
-continued
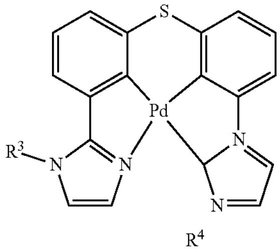
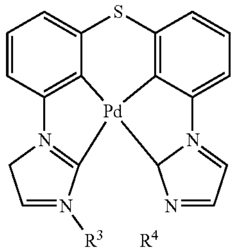
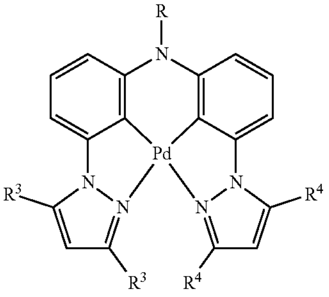
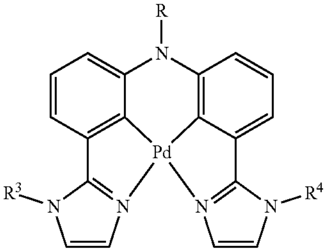
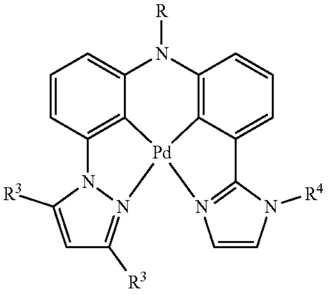
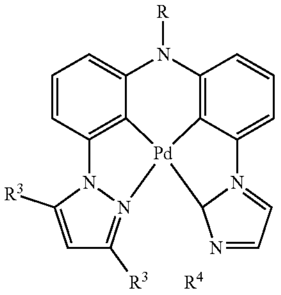
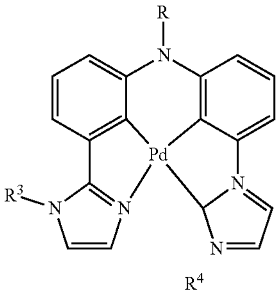
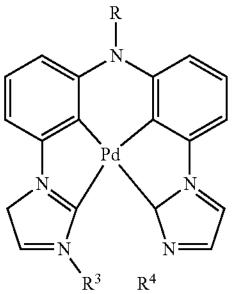

-continued
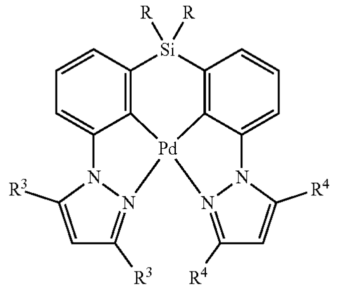
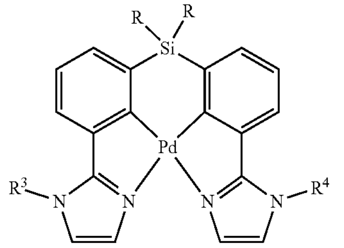
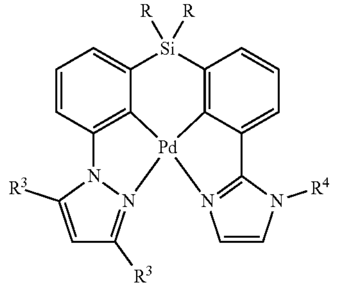
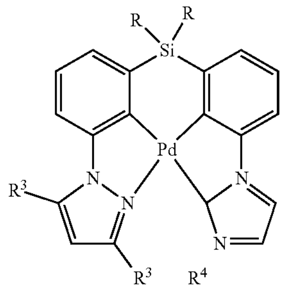
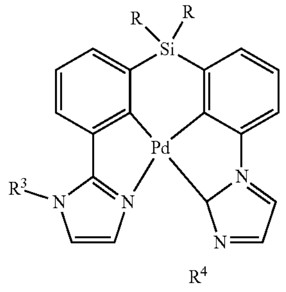
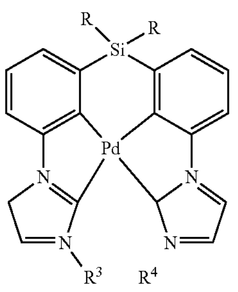
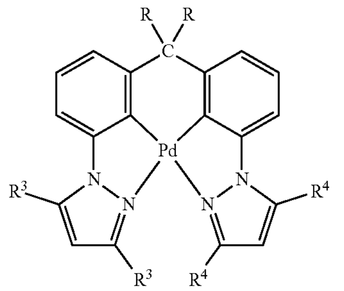
-continued
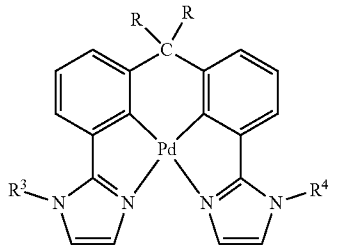
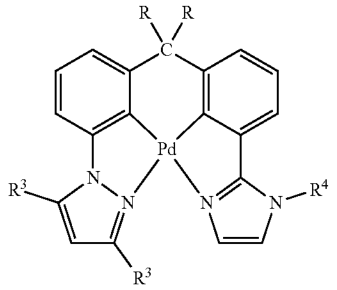
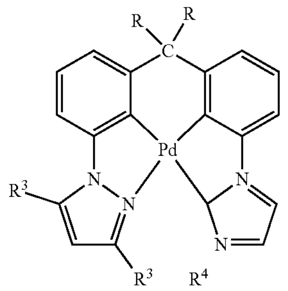
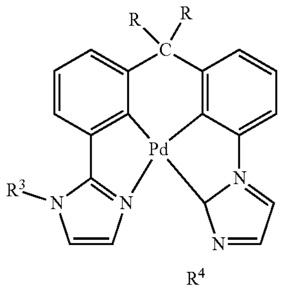
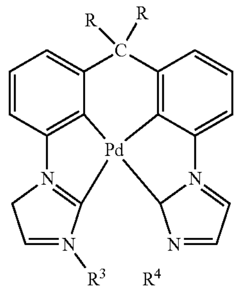
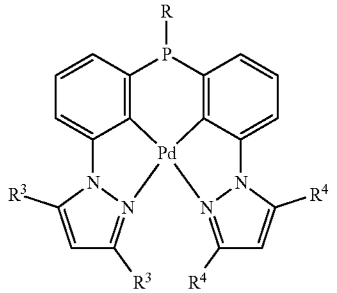
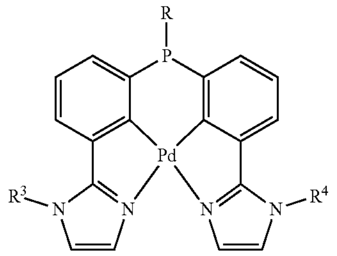

-continued
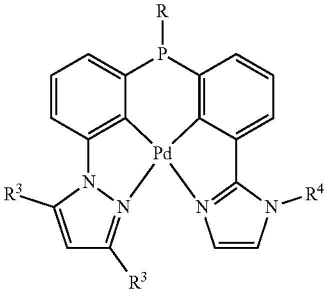
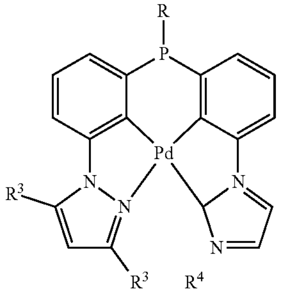
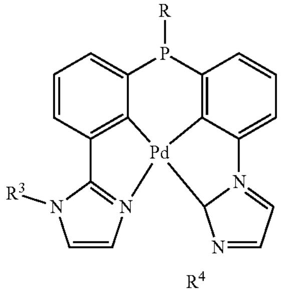
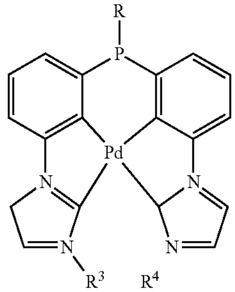
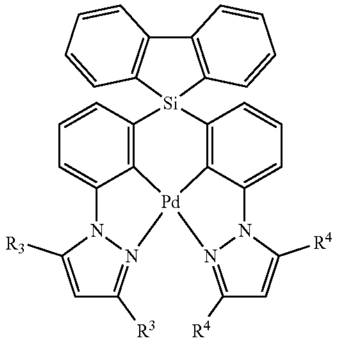
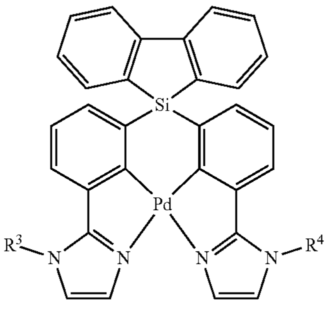
-continued
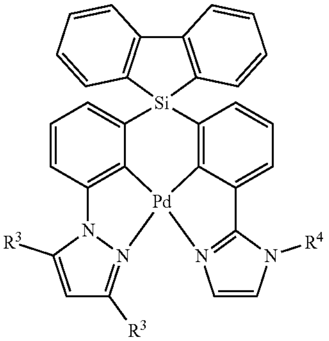
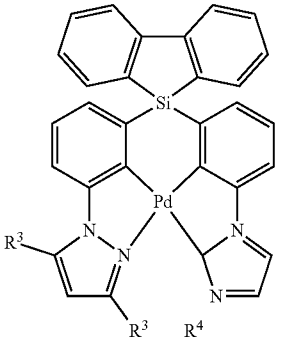
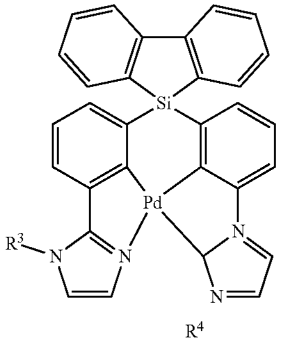
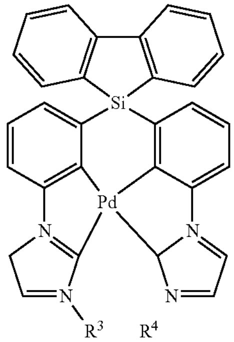
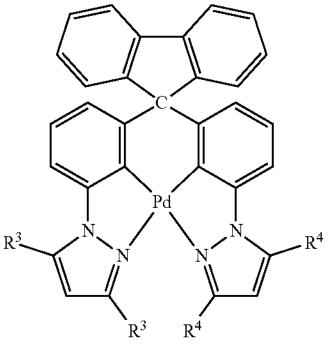
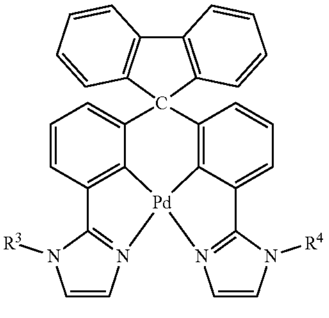

-continued
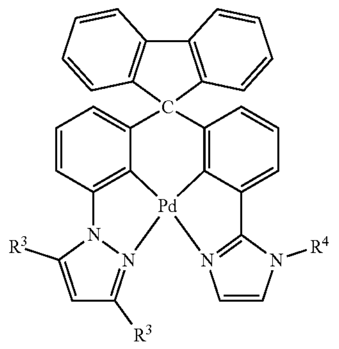
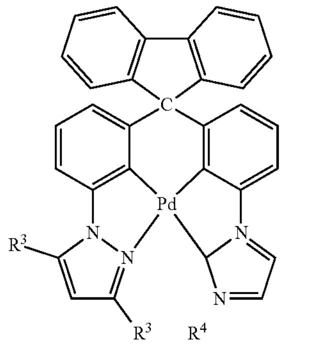
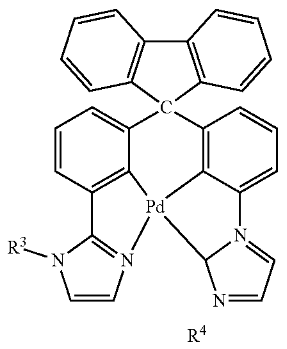
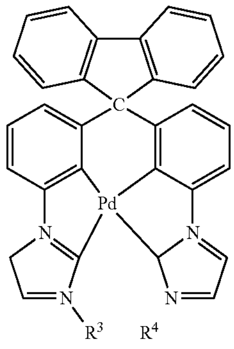
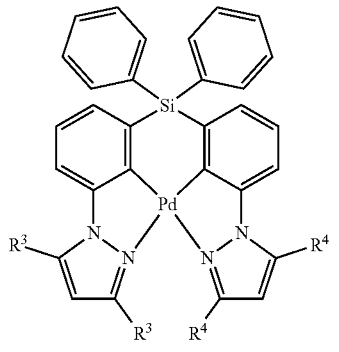
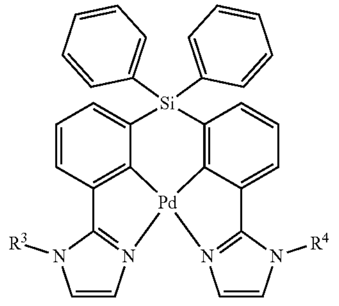
-continued
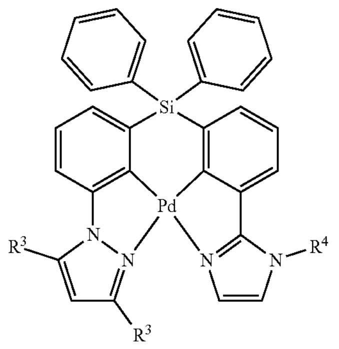
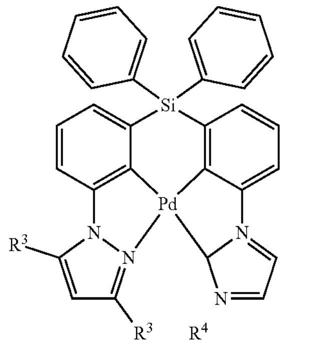
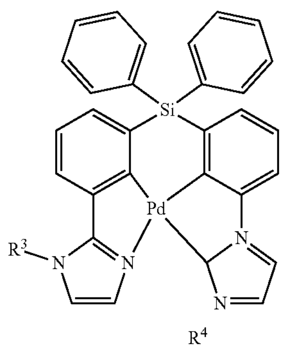
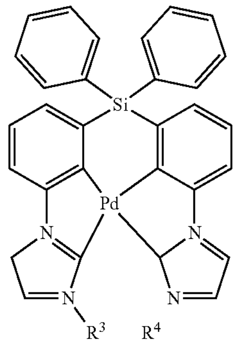
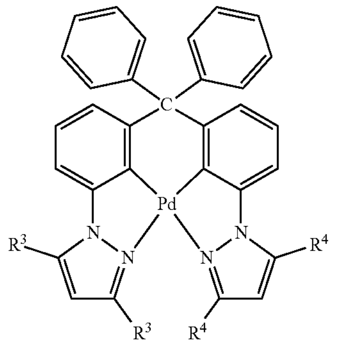
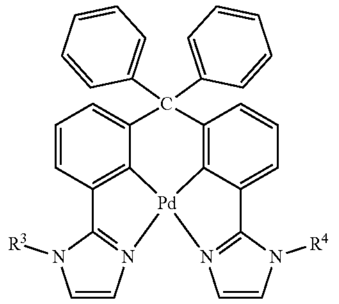

-continued
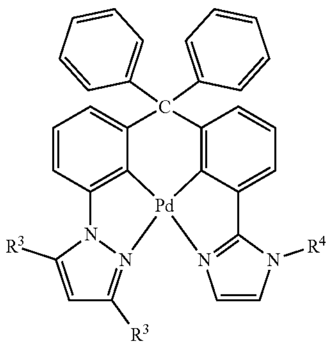
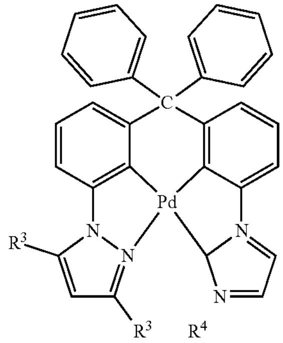
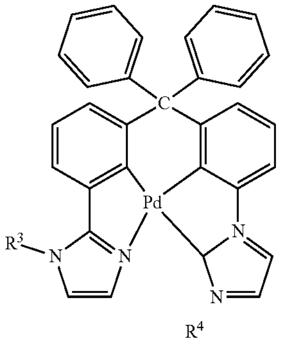
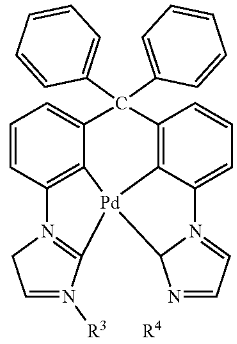
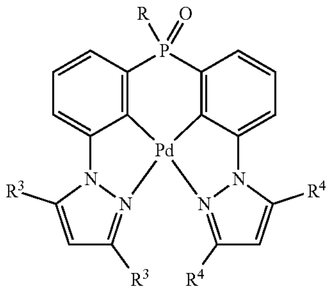
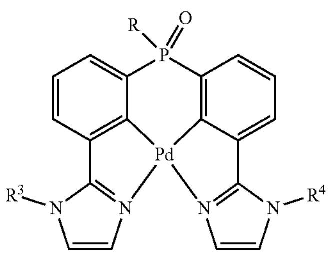
-continued
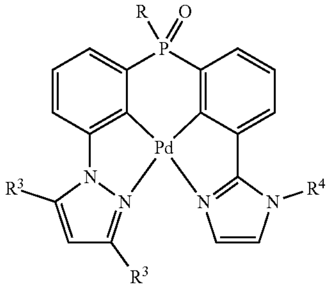
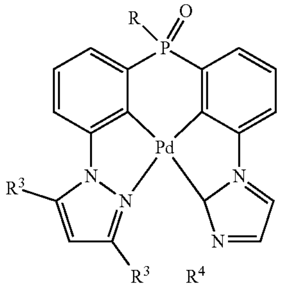
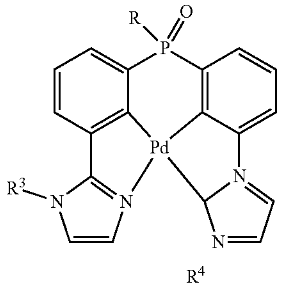
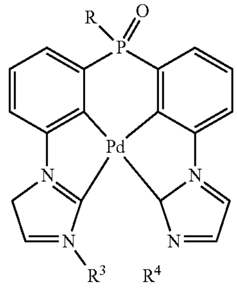
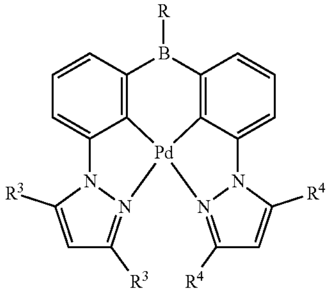
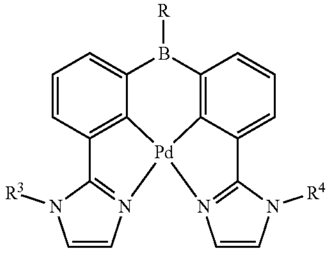
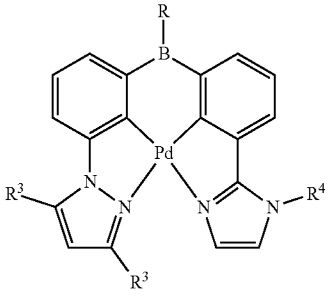

-continued
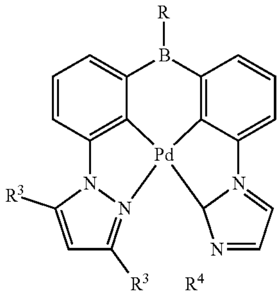
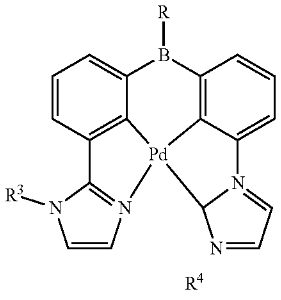
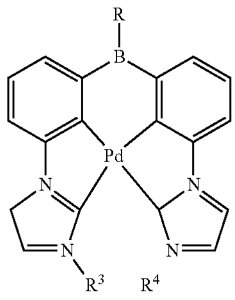
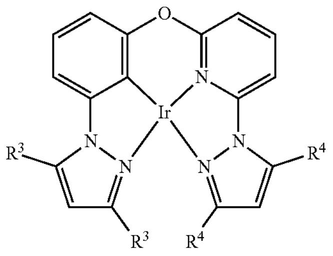
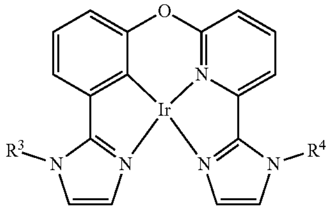
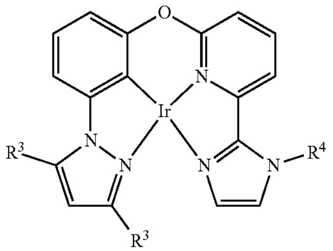
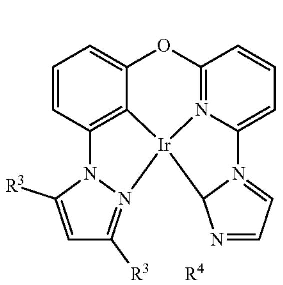
-continued
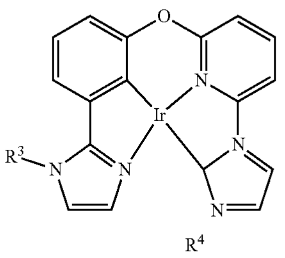
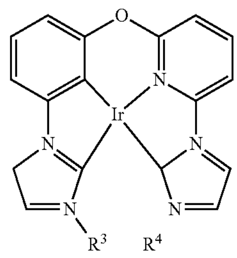
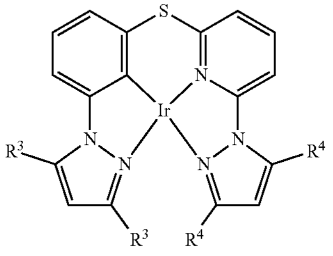
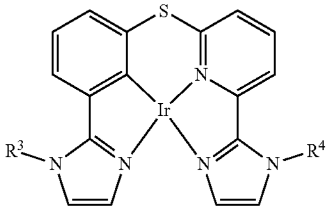
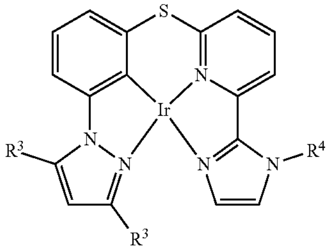
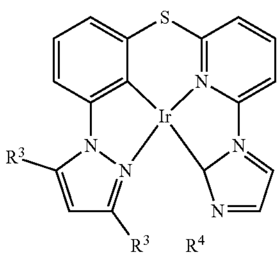
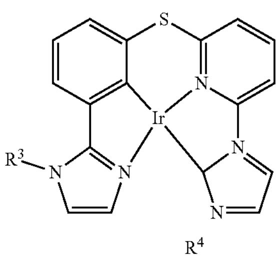
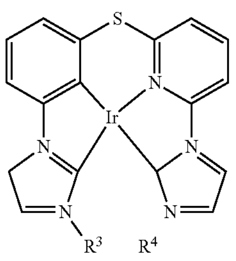

-continued
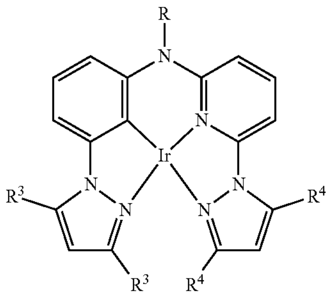
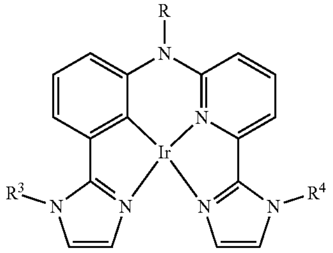
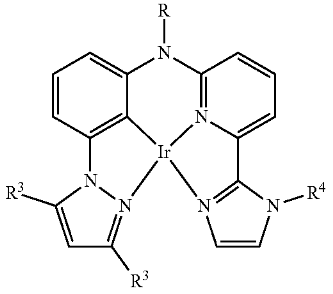
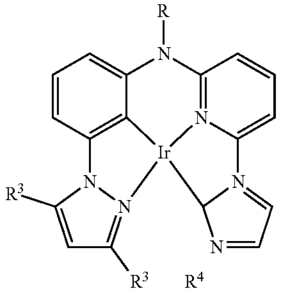
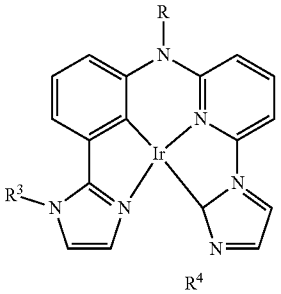
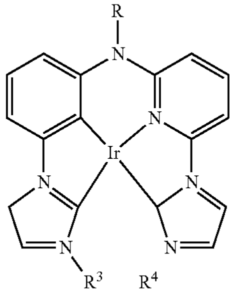
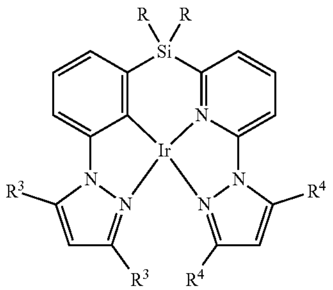
-continued
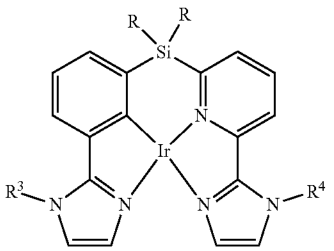
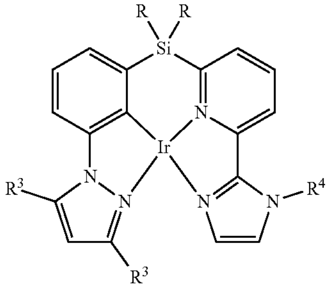
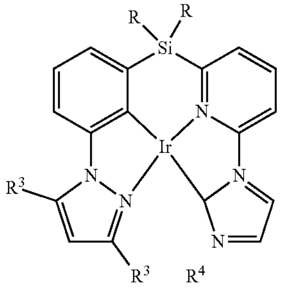
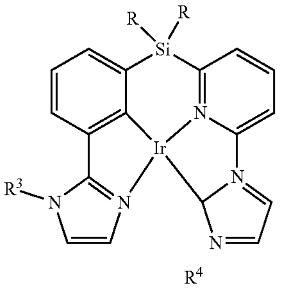
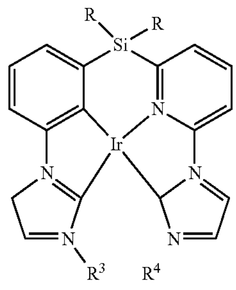
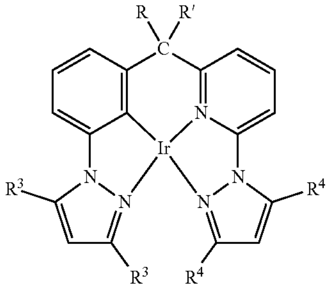
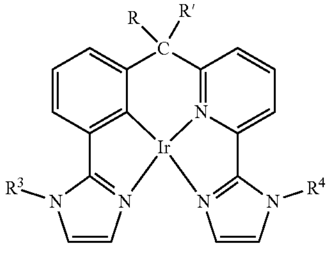

-continued
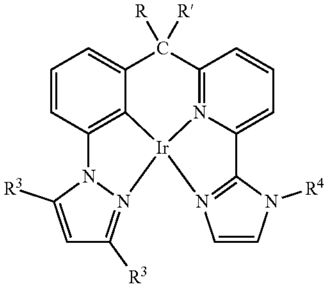
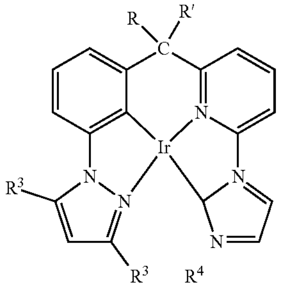
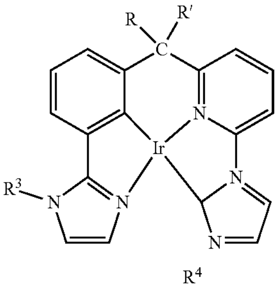
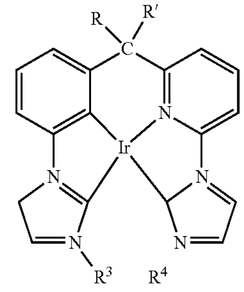
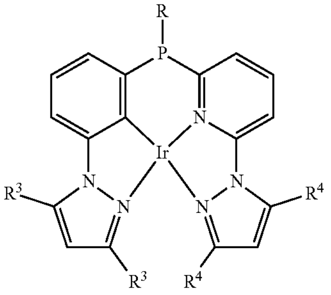
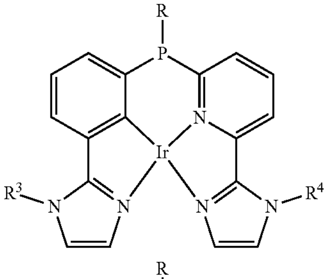
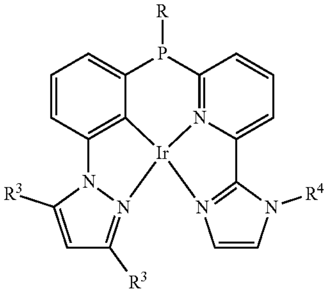
-continued
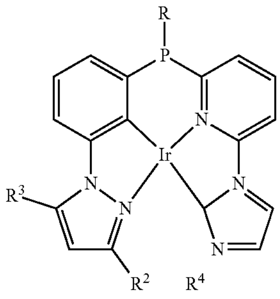
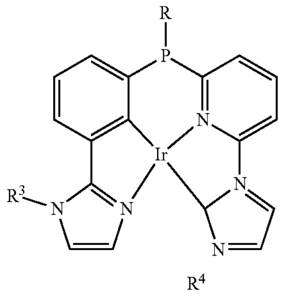
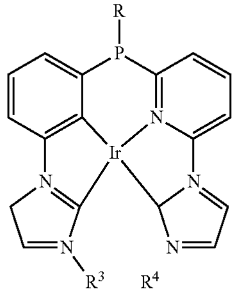
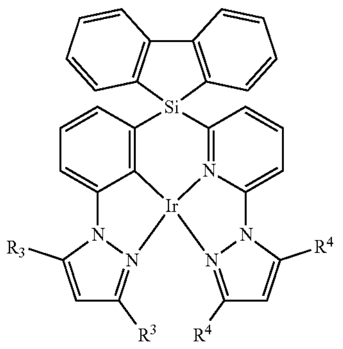
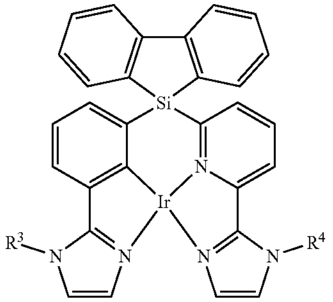
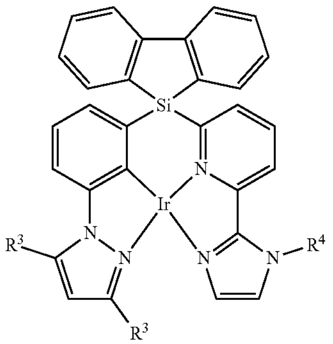

-continued
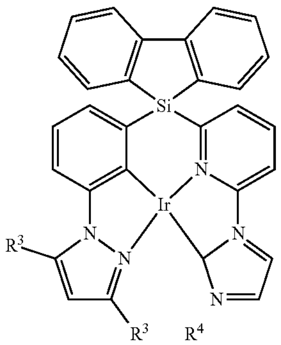
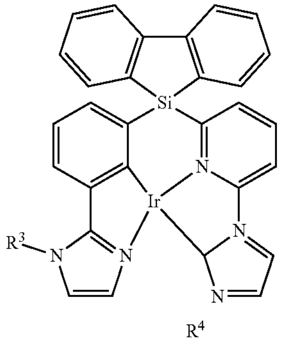
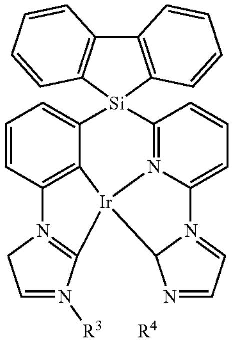
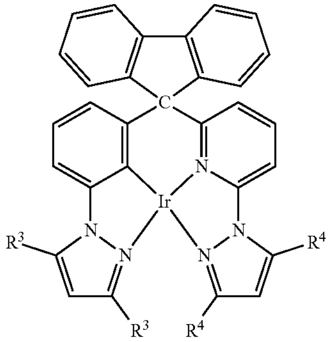
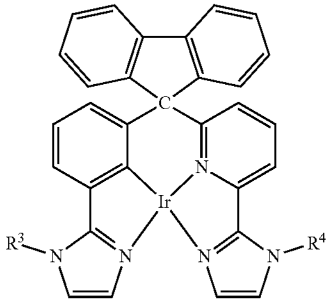
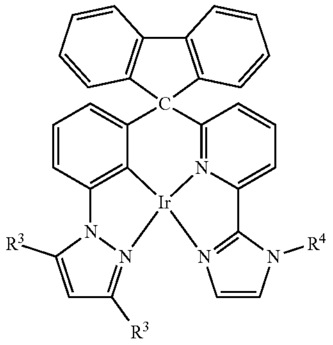
-continued
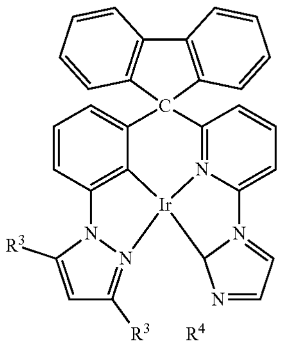
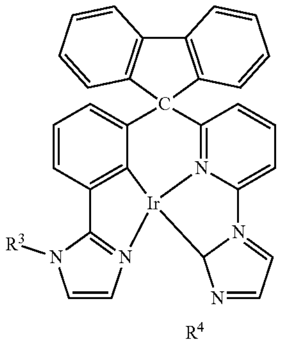
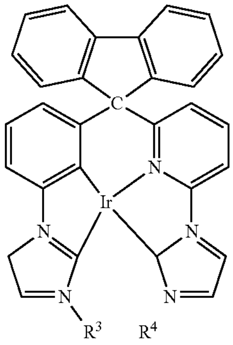
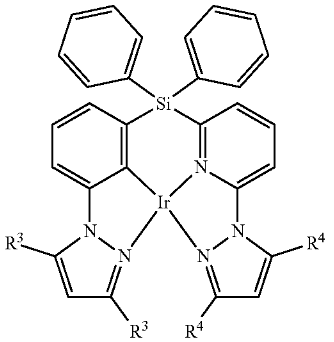
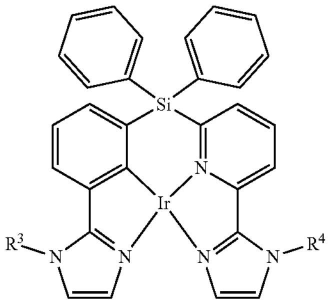
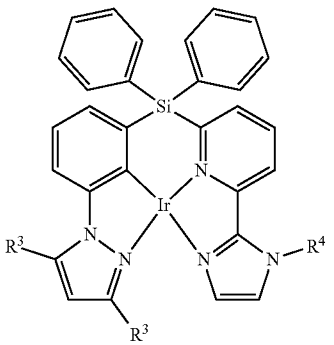

-continued
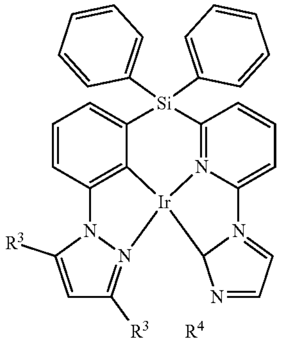
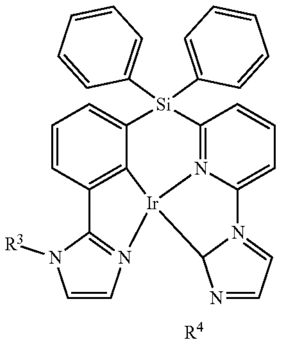
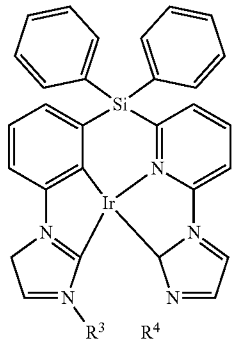
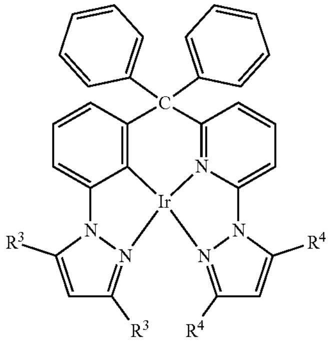
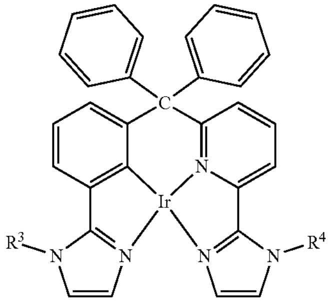
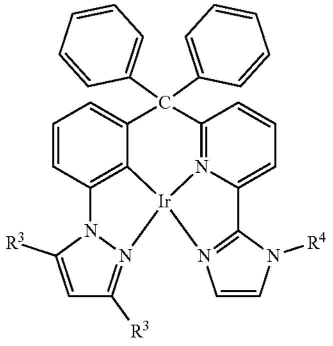
-continued
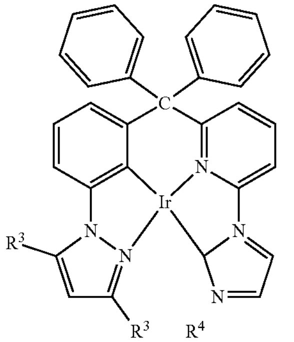
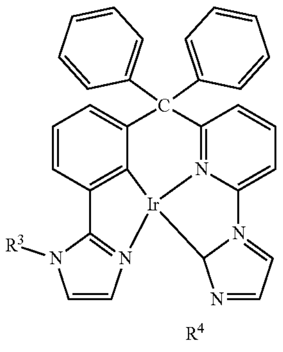
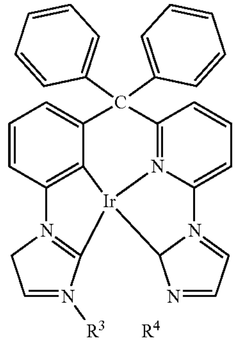
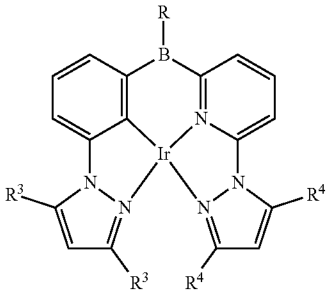
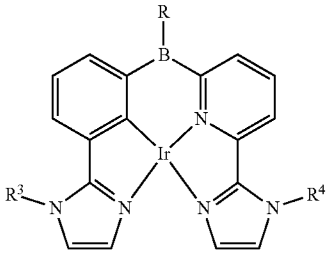
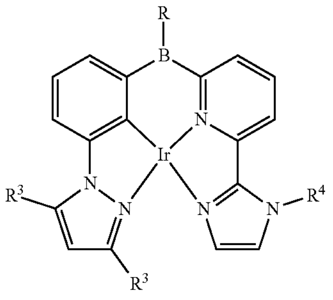

-continued
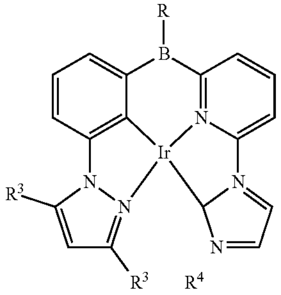
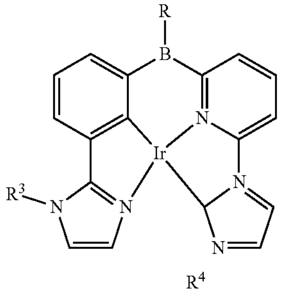
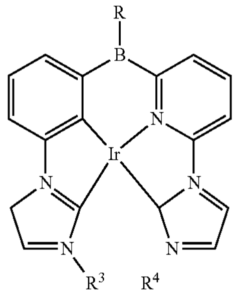
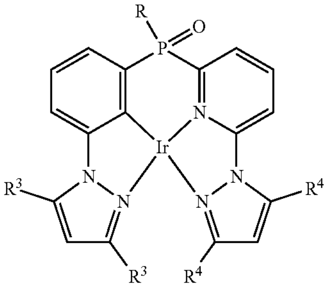
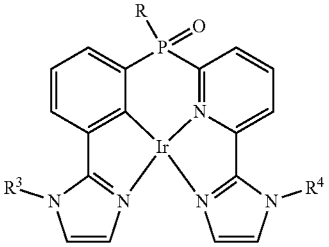
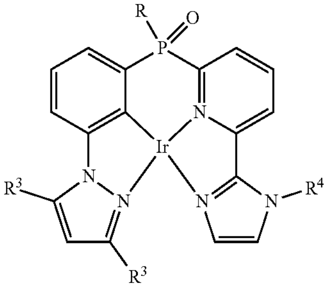
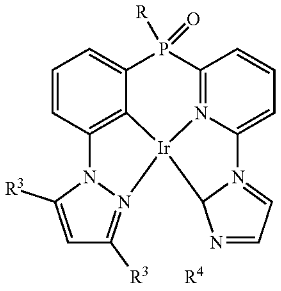
-continued
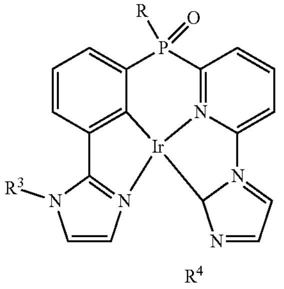
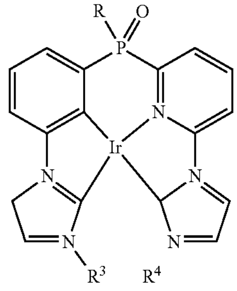
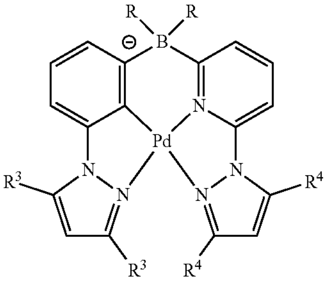
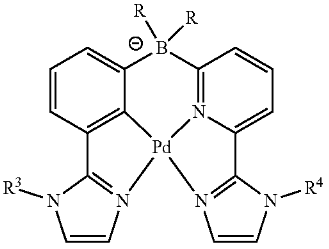
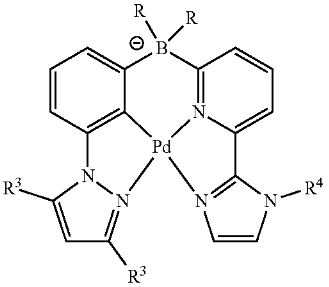
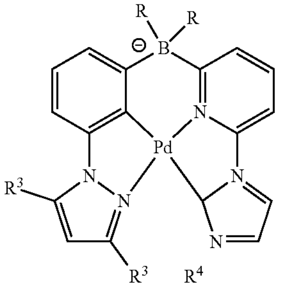
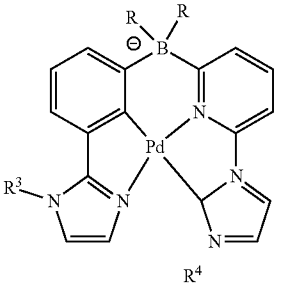
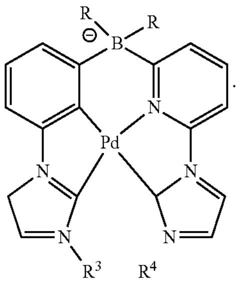

Compounds of General Formula 2 have the following structure:

General Formula 2

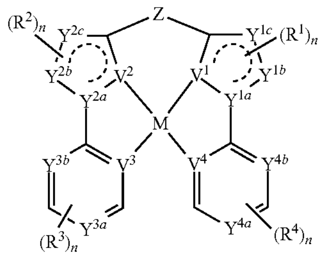

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{1c}$, $Y^{2a}$, $Y^{2b}$, $Y^{2c}$, $Y^{3a}$, $Y^{3b}$, $Y^{4a}$, $Y^{4b}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, substituted or unsubstituted aryl.

A compound of General Formula 2 may have one of the following

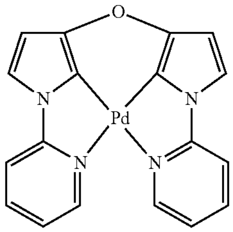
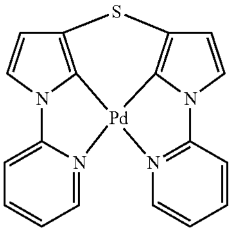
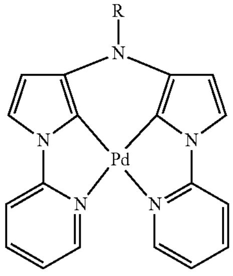
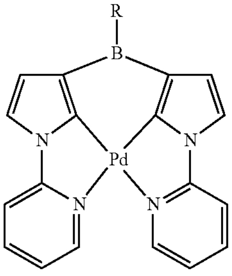
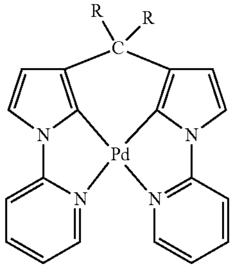
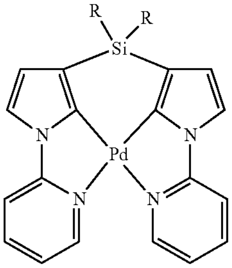

-continued

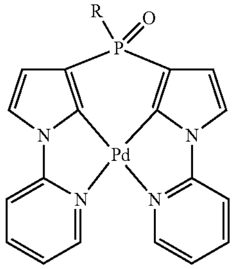
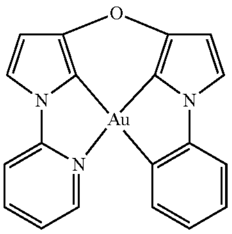
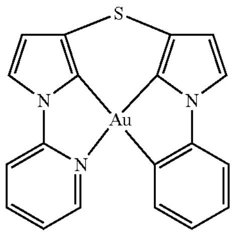
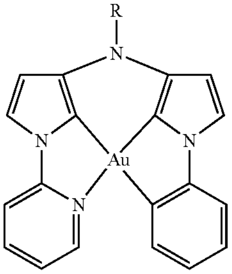
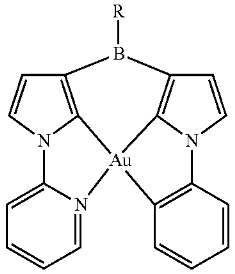
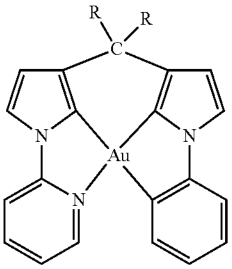
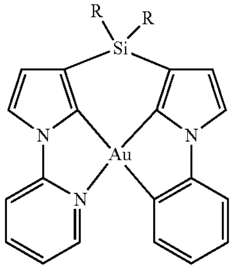
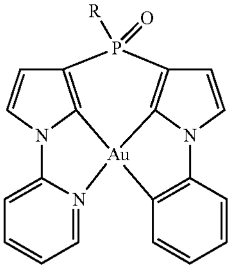
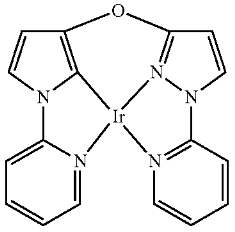
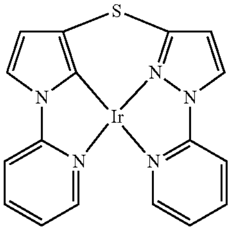
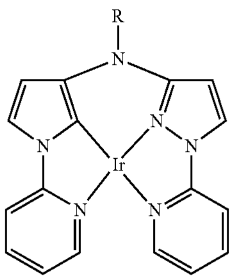
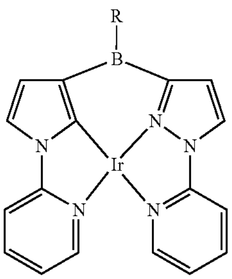

-continued
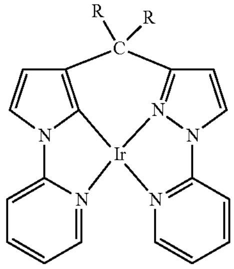
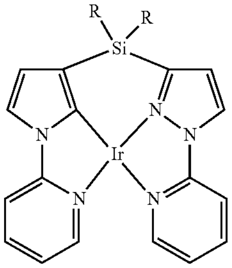
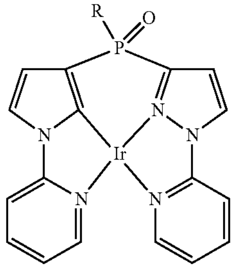
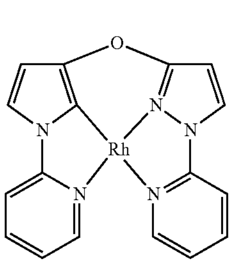
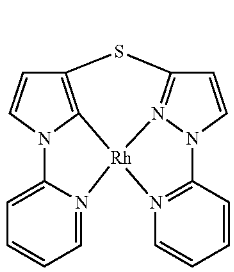
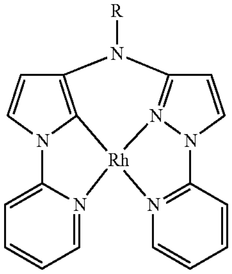
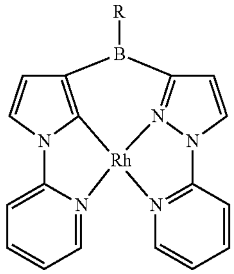
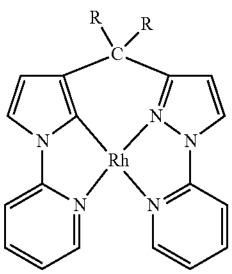
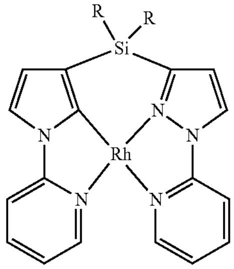
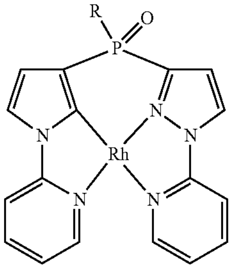
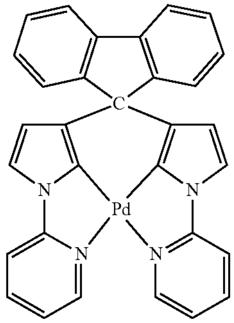
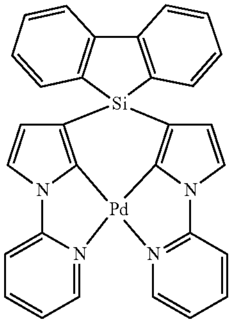
-continued
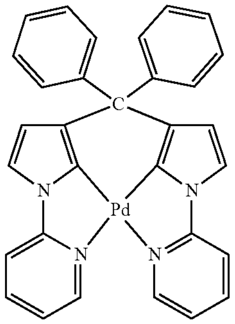
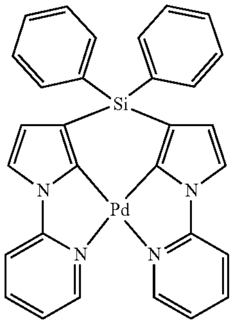
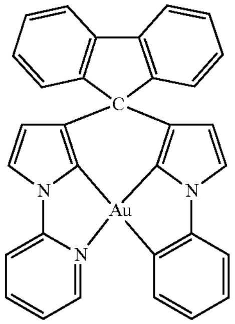
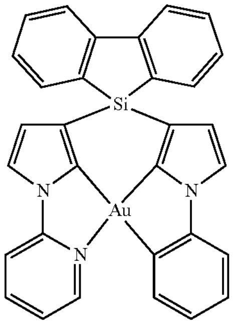
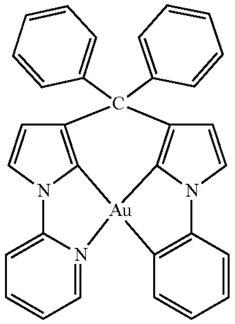
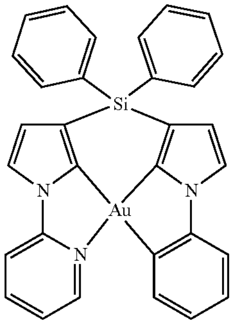
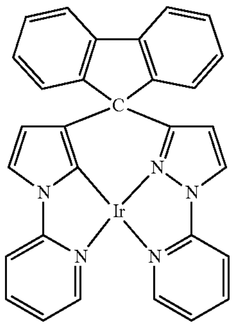
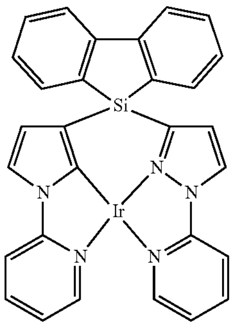
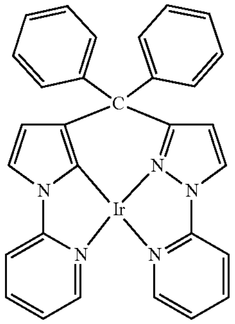
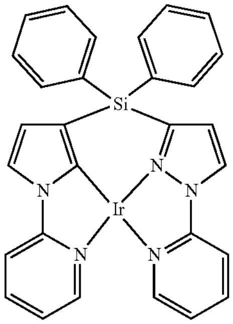

-continued

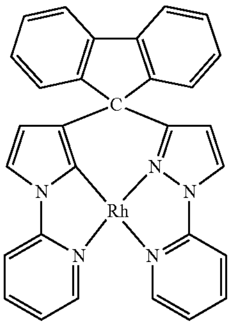

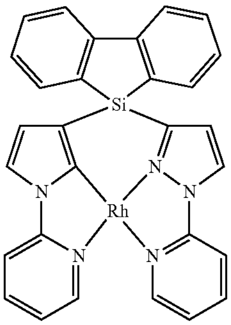

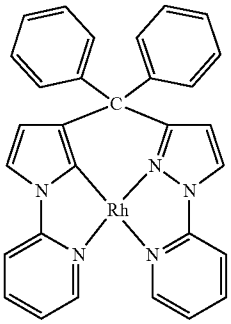

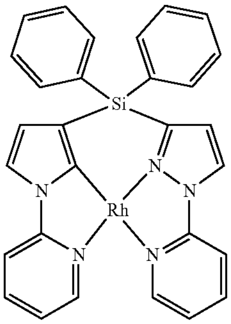

Compounds of General Formula 3 have the following structure:

General Formula 3

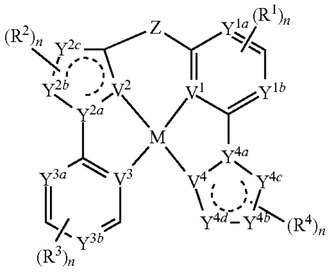

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$, $Y^{3a}$, $Y^{3b}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, thiol, or substituted or unsubstituted $C_1$-$C_4$ alkyl, alkoxy, or aryl, hydroxyl, amino, nitro, or thiol.

A compound of General Formula 3 may have one of the following structures:

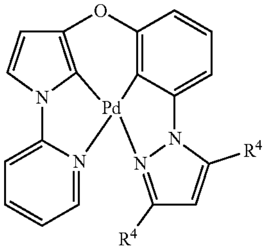

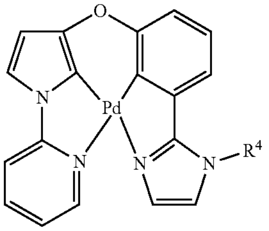

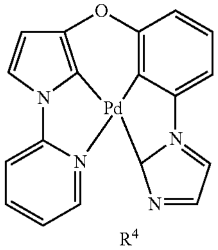

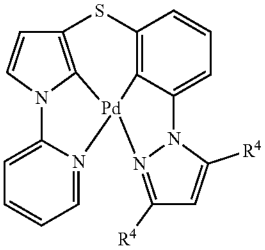

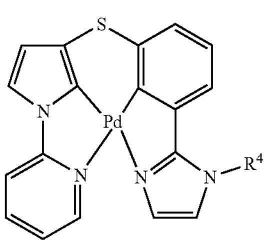

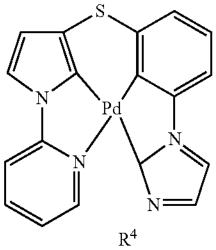

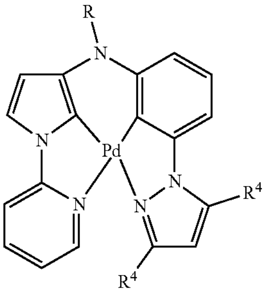

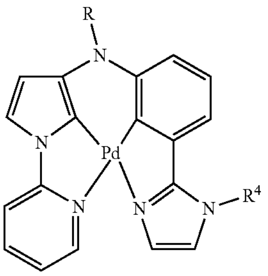

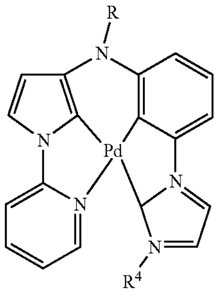

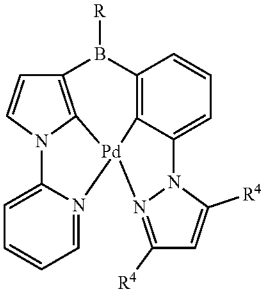

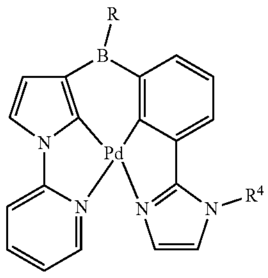

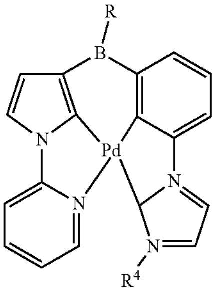

-continued
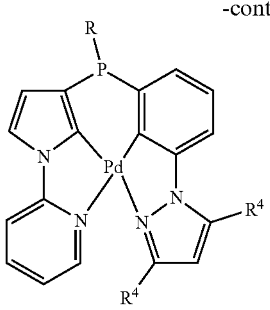
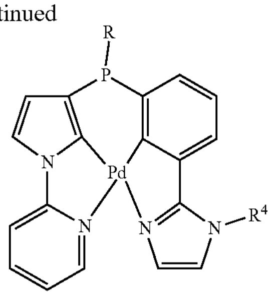
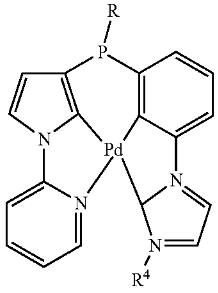
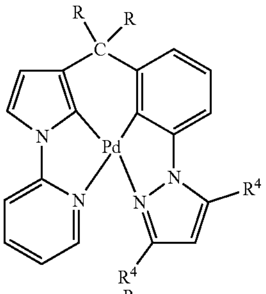
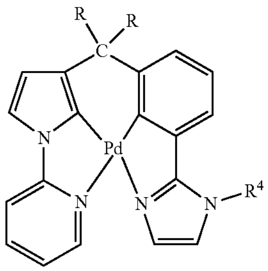
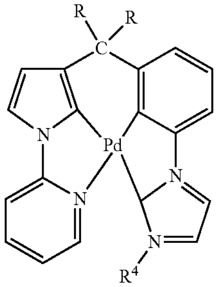
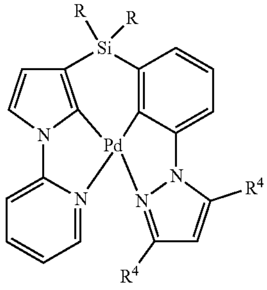
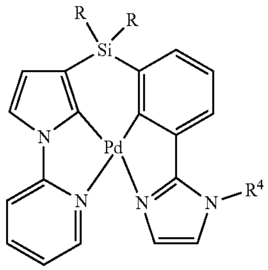
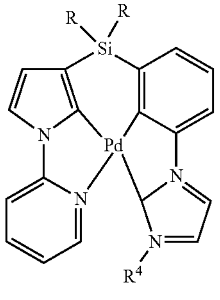
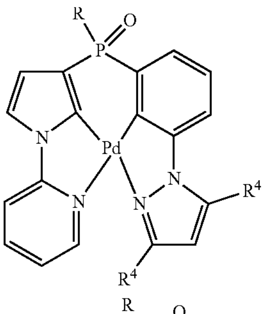
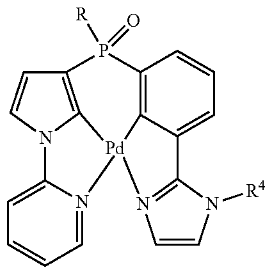
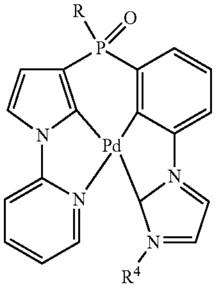
-continued
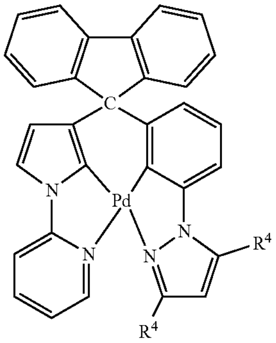
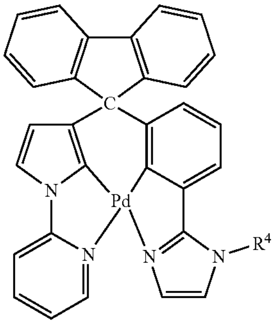
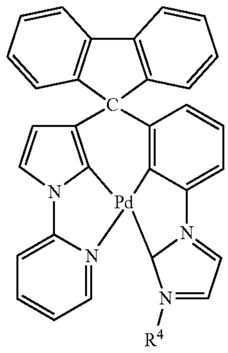
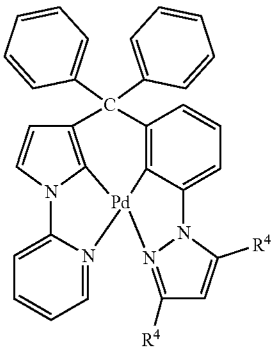
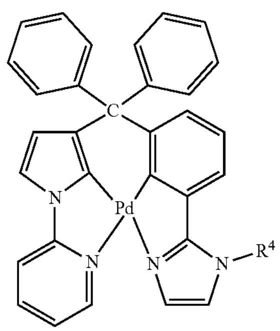
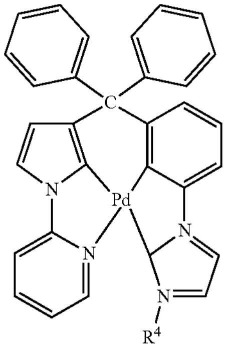
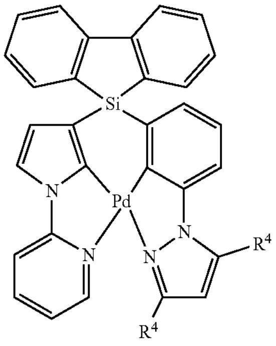
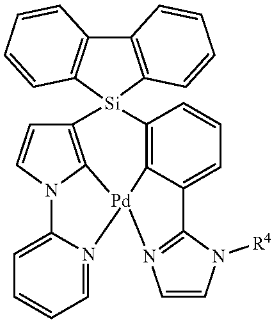
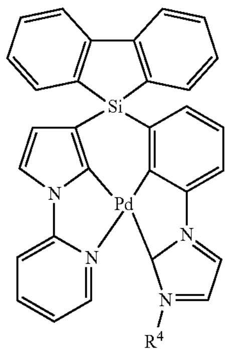
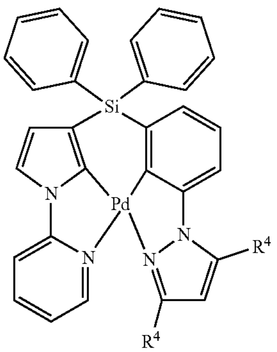

-continued

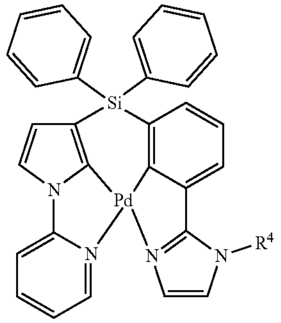

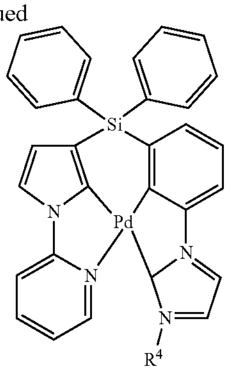

Compounds of General Formula 4 have the following structure:

General Formula 4

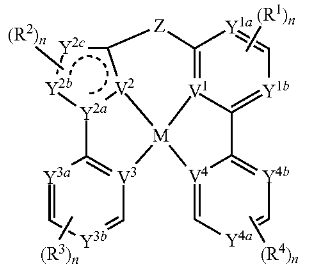

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$ $Y^{3a}$, $Y^{3b}$, $Y^{4a}$, $Y^{4b}$, is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

A compound of General Formula 4 may have one of the following structures:

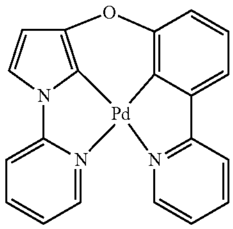

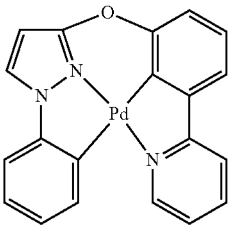

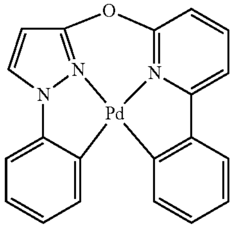

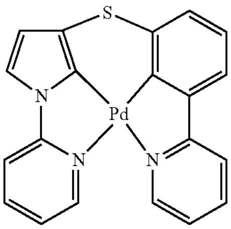

-continued

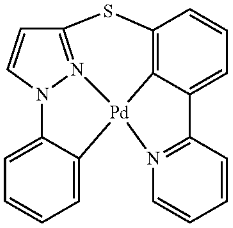

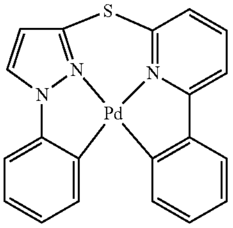

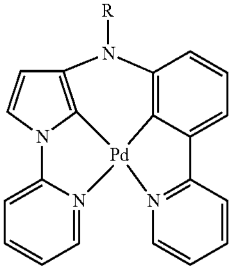

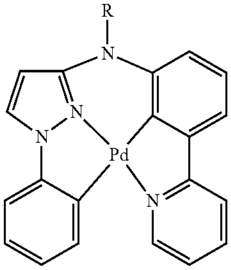

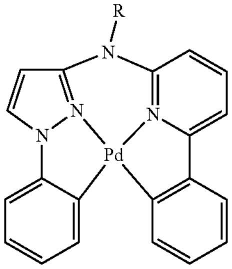

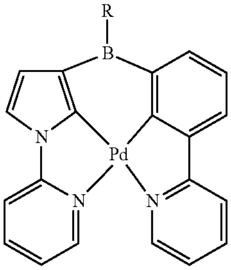

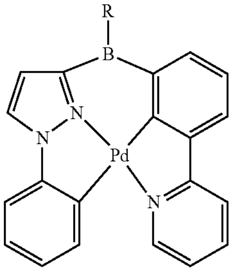

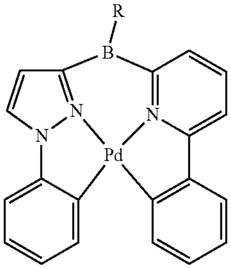

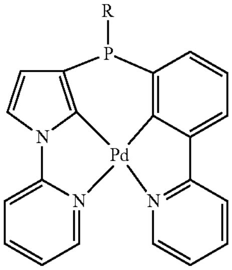

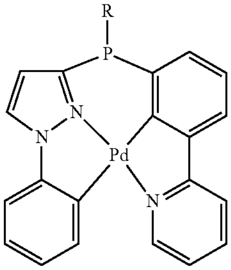

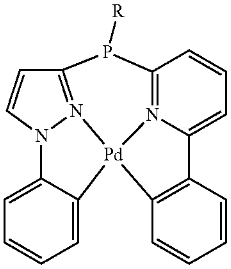

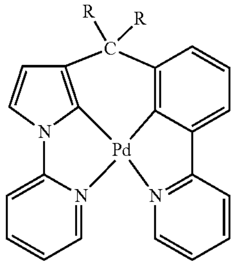

-continued
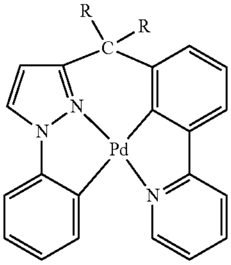
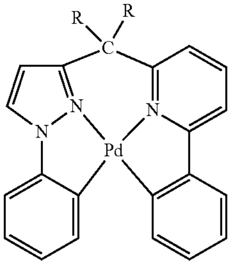
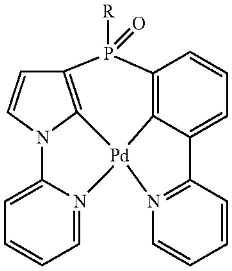
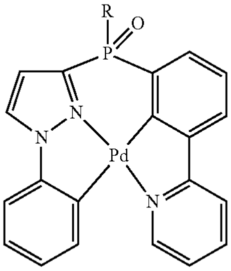
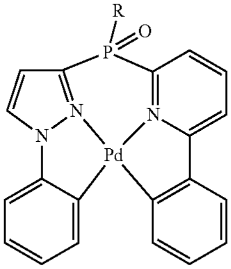
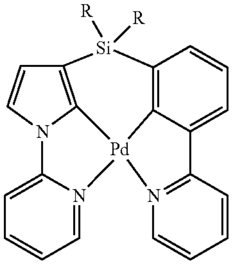
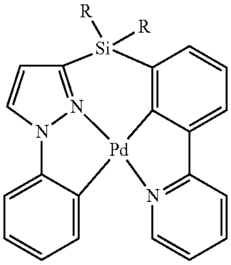
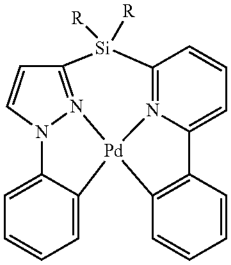
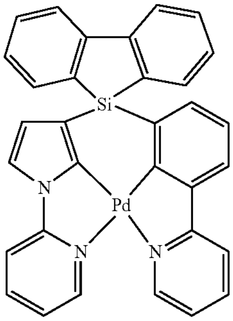
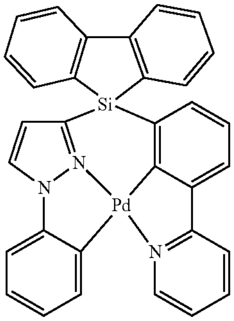
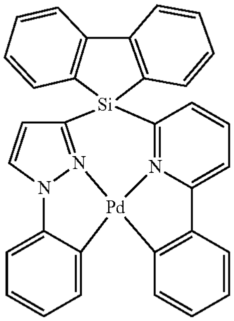
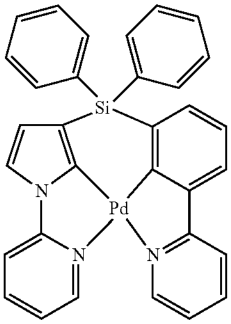
-continued
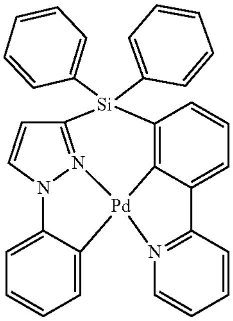
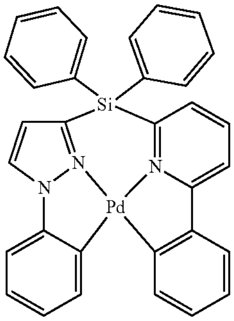
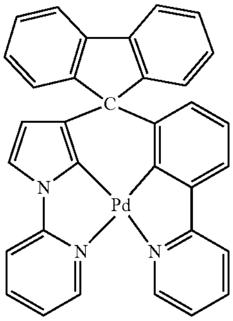
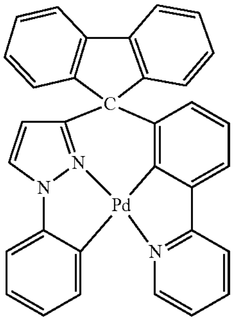
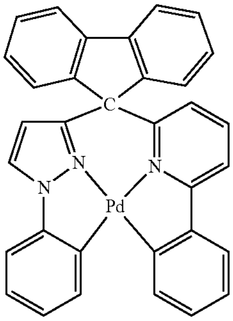
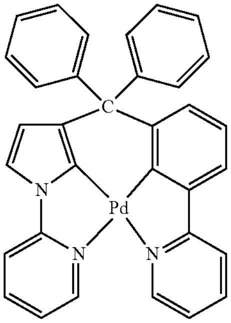
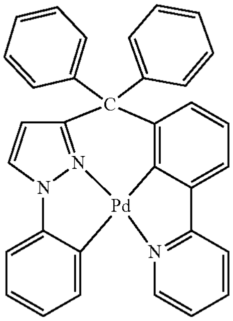
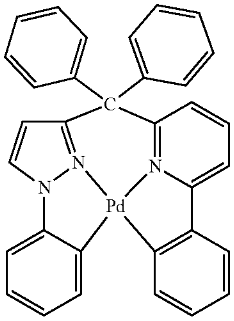
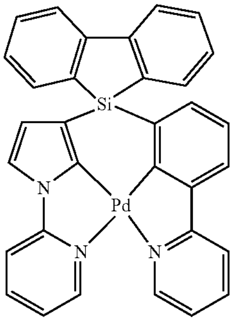
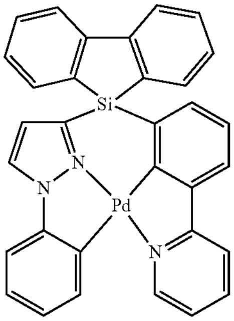

-continued
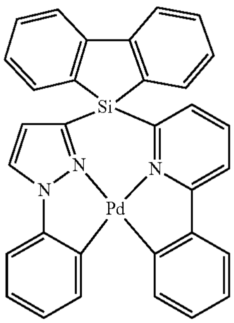
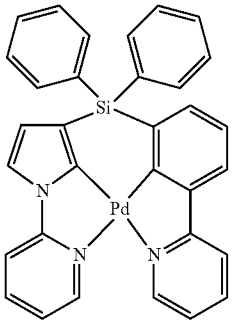
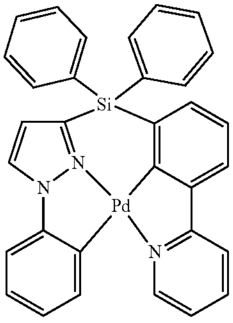
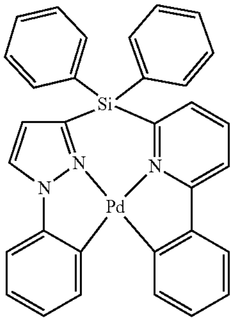
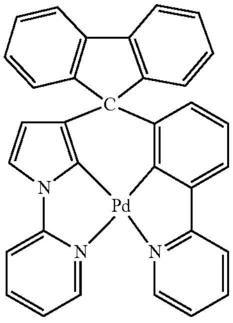
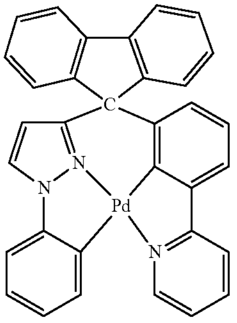
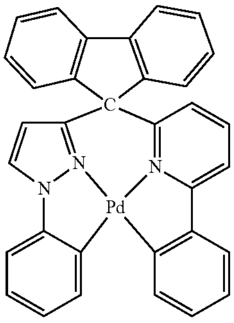
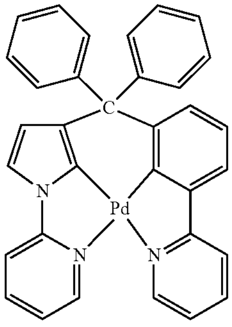
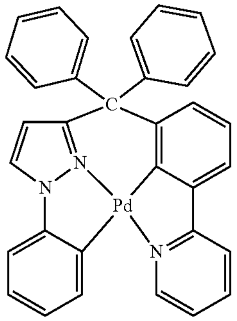
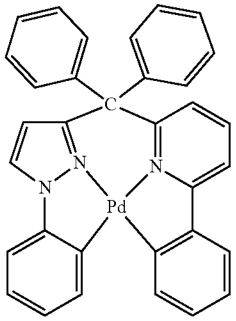
-continued
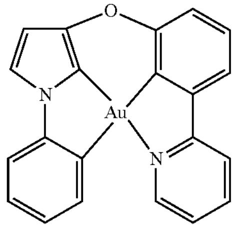
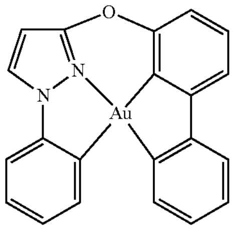
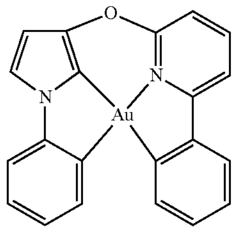
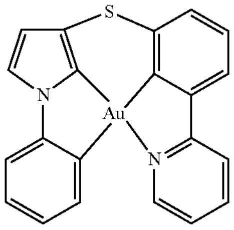
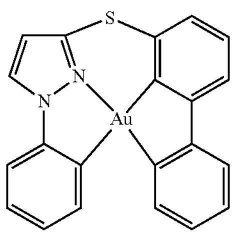
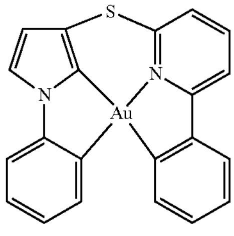
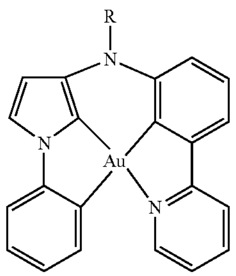
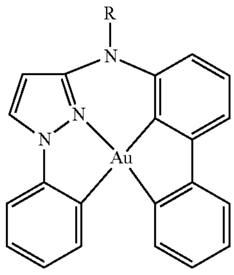
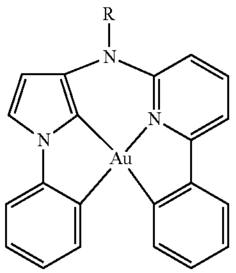
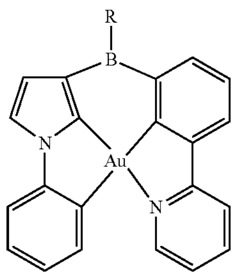
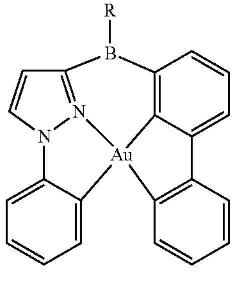
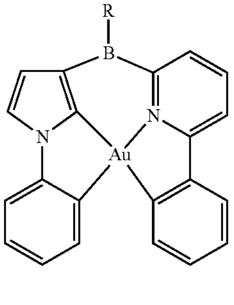

-continued
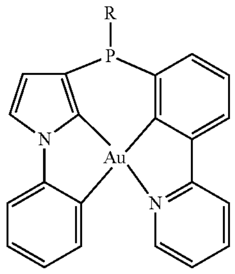
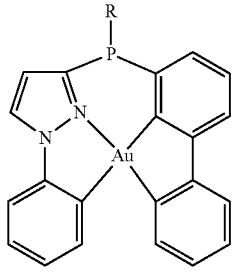
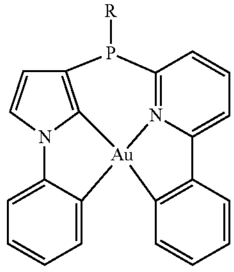
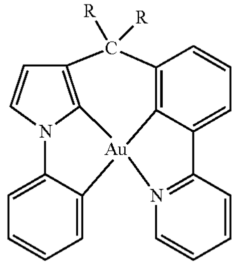
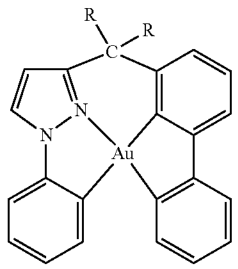
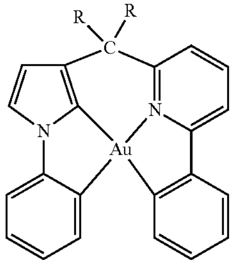
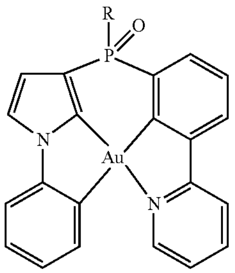
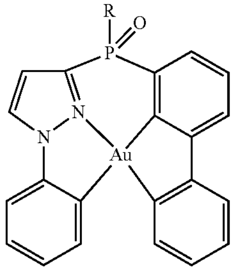
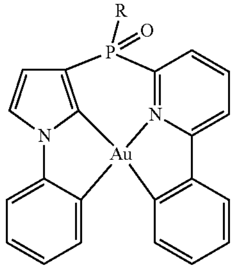
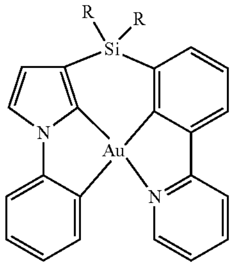
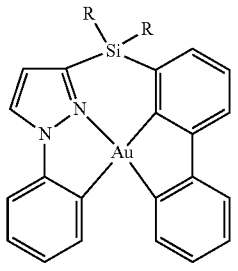
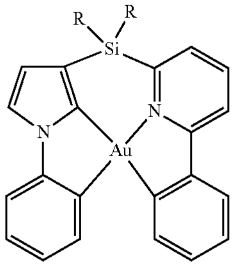
-continued
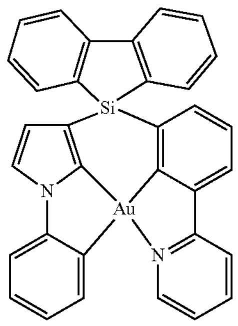
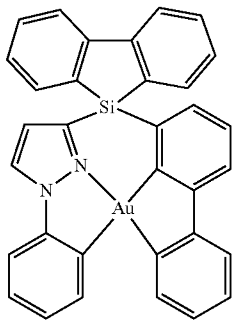
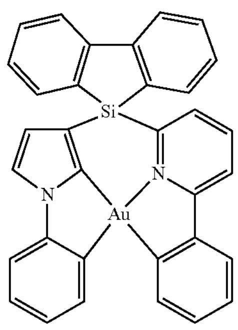
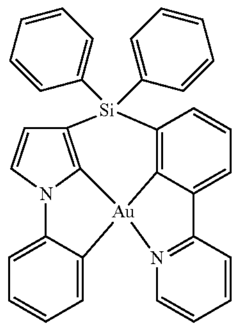
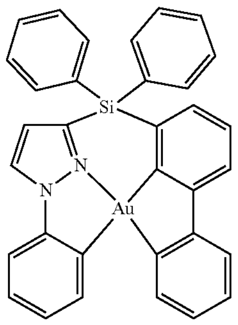
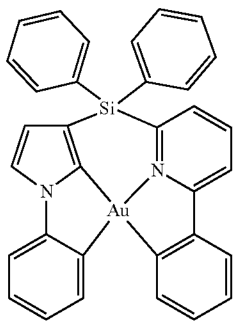
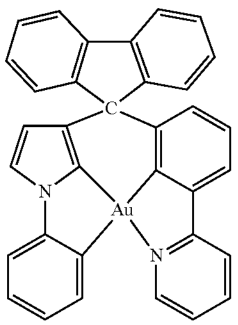
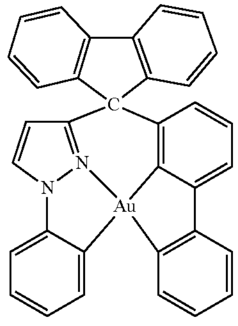
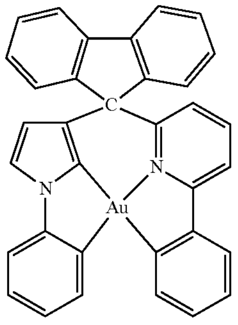
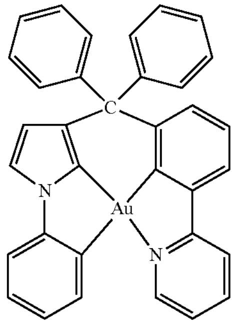

-continued
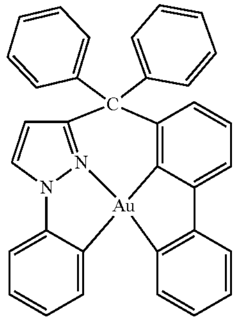
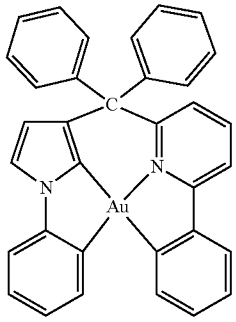
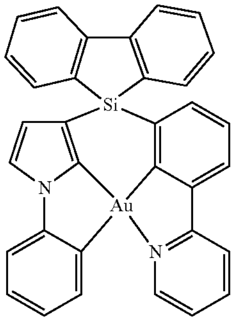
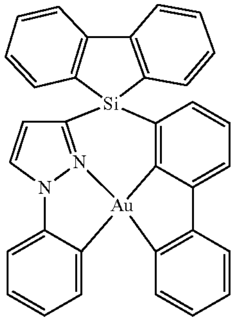
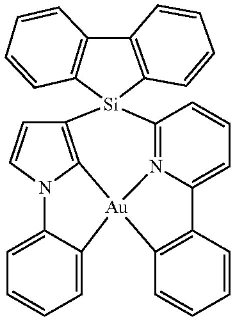
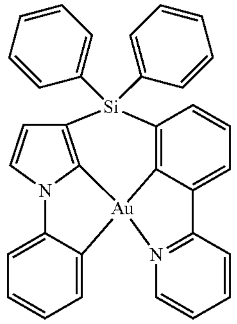
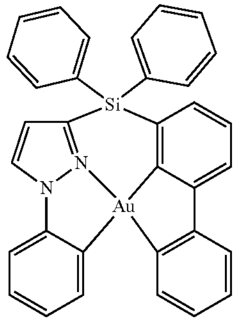
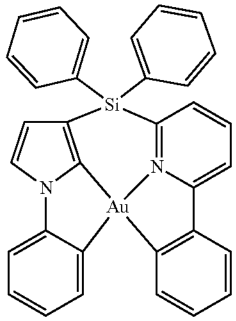
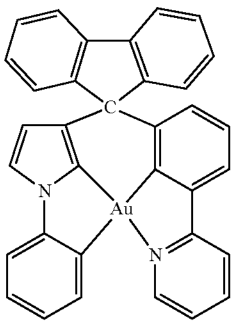
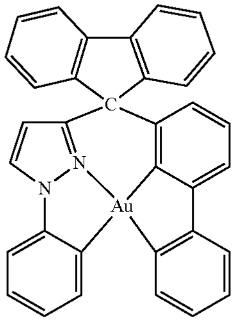
-continued
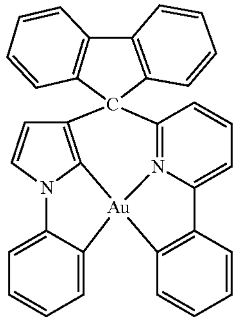
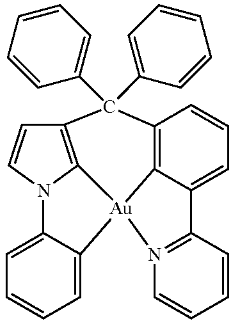
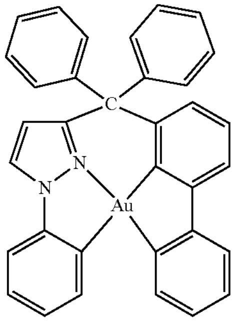
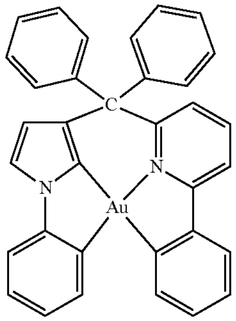
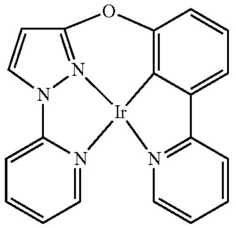
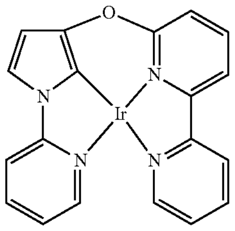
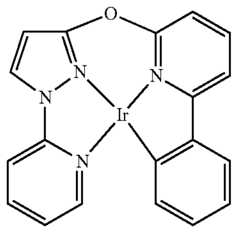
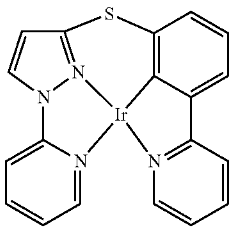
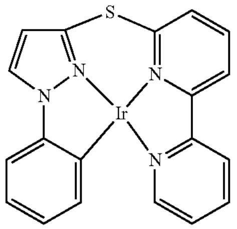
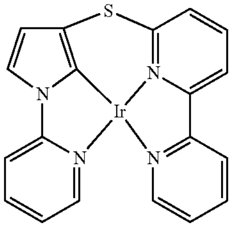
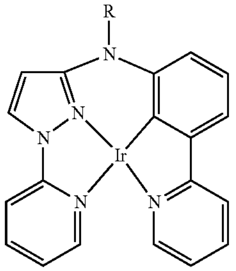
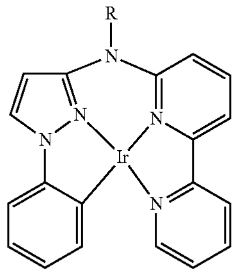

-continued
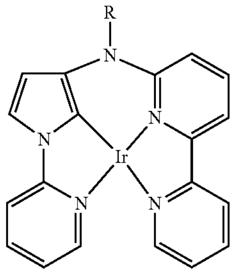
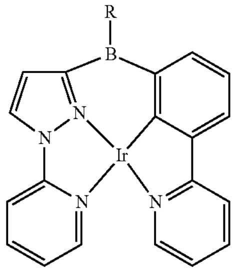
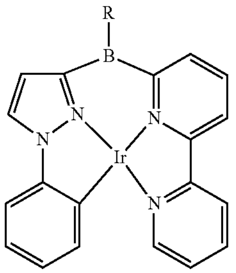
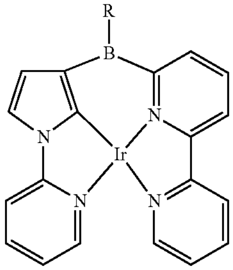
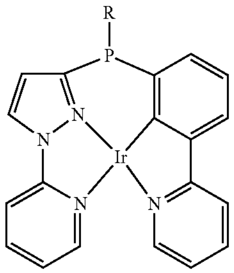
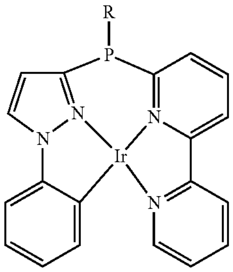
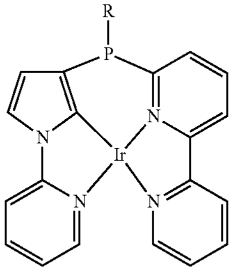
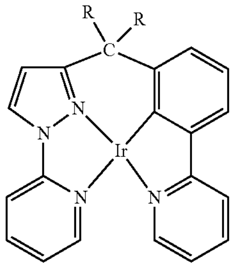
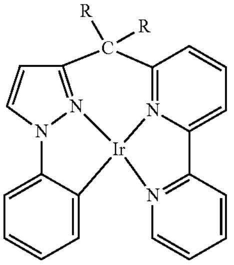
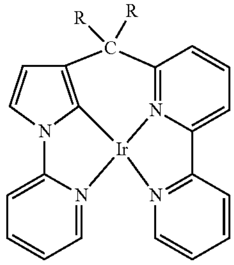
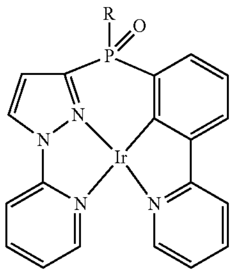
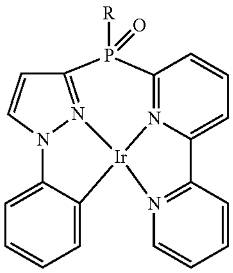
-continued
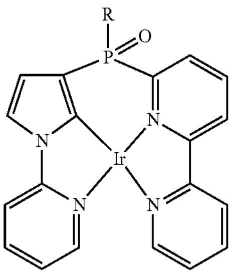
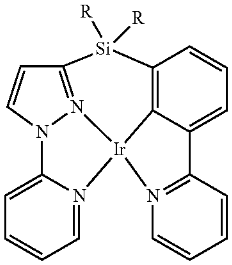
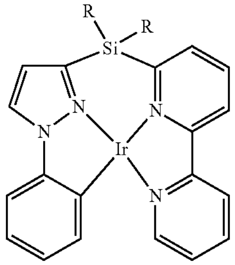
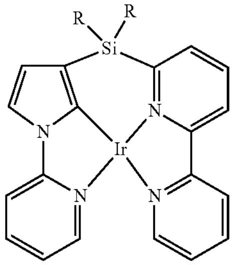
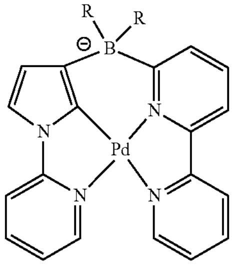
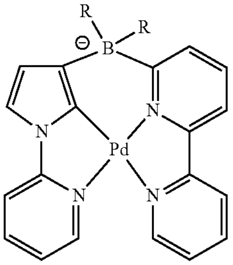
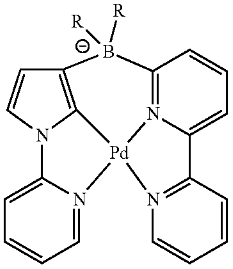
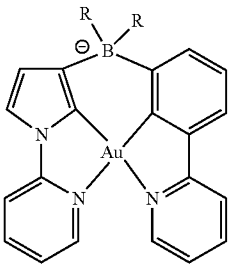
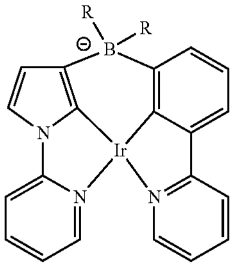
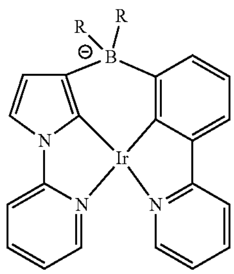

Compounds of General Formula 5 have the following structure:

General Formula 5

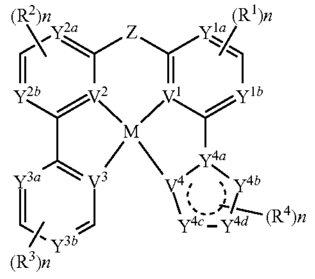

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

A compound of General Formula 5 may have one of the following structures:

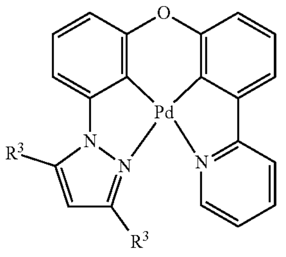

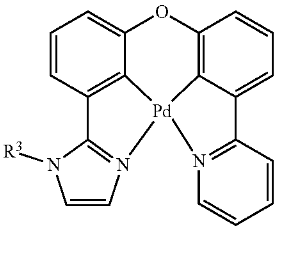

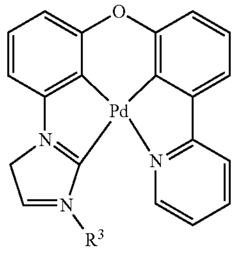

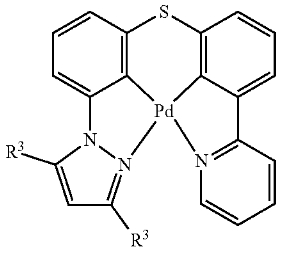

-continued

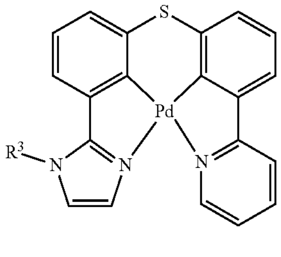

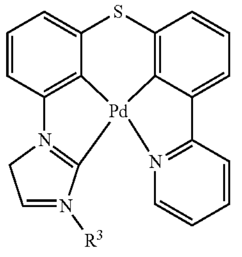

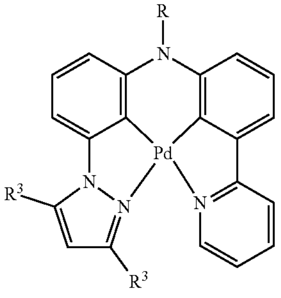

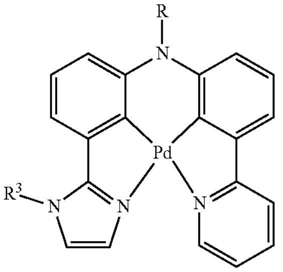

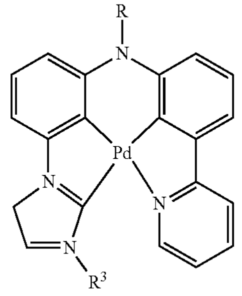

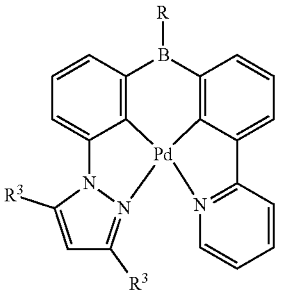

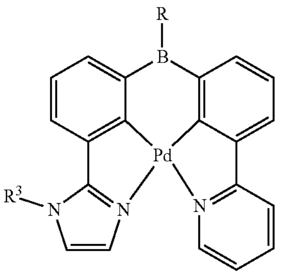

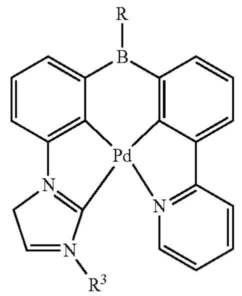

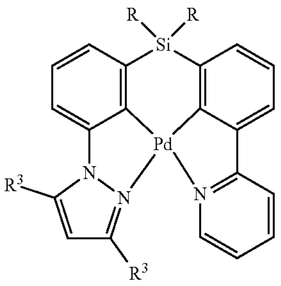

-continued
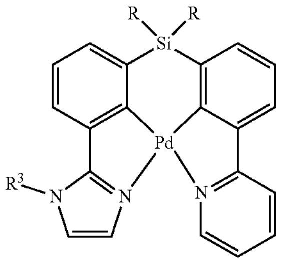
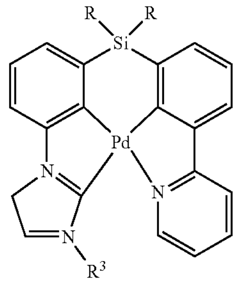
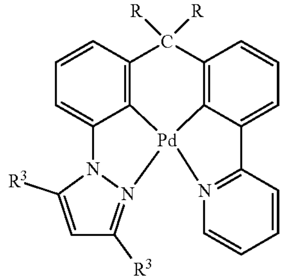
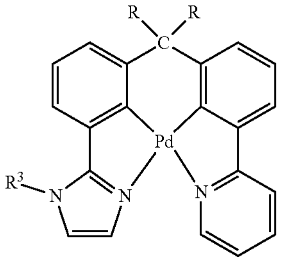
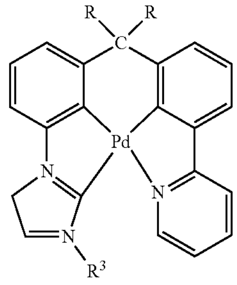
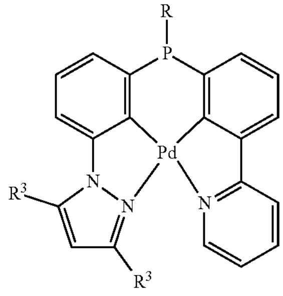
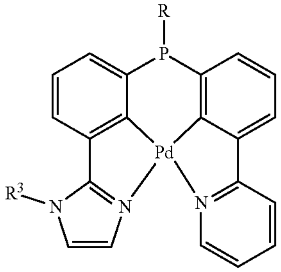
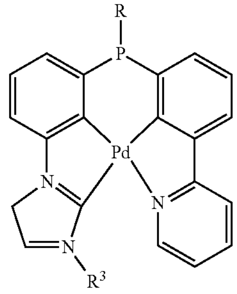
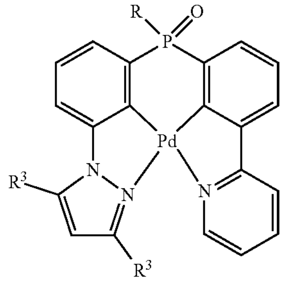
-continued
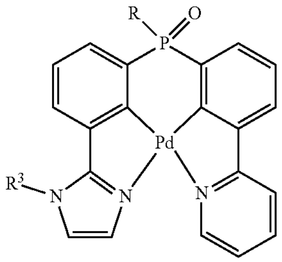
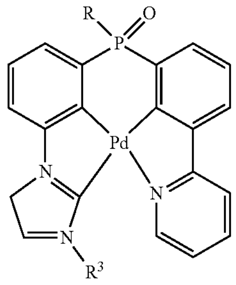
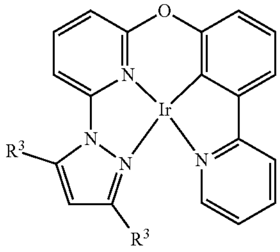
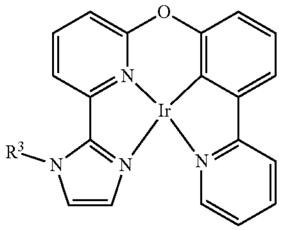
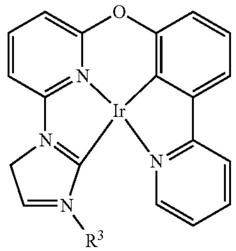
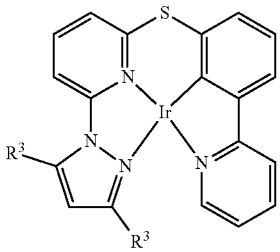
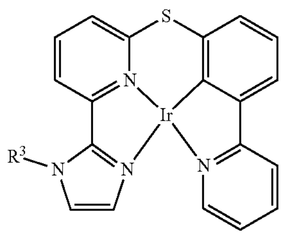
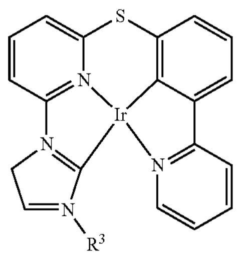
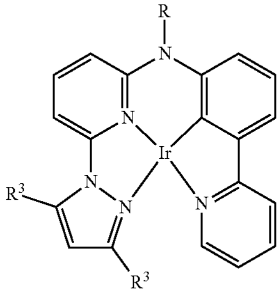

-continued
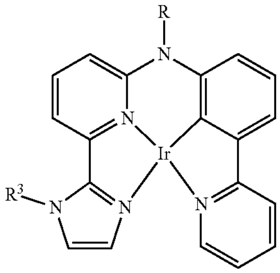
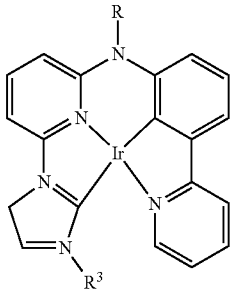
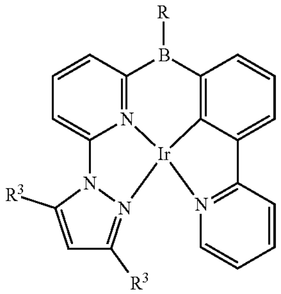
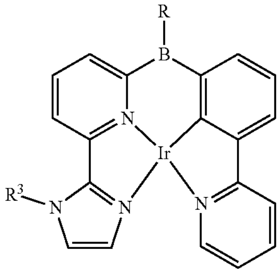
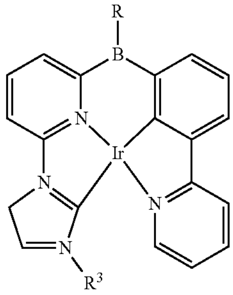
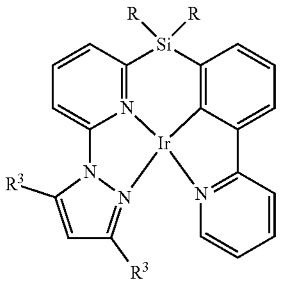
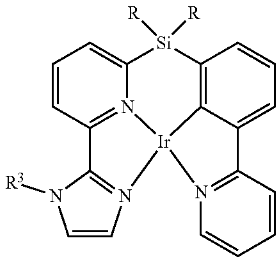
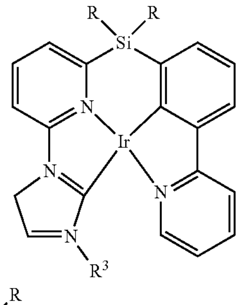
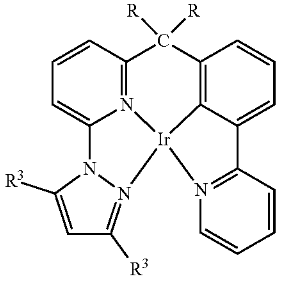
-continued
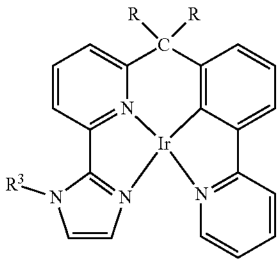
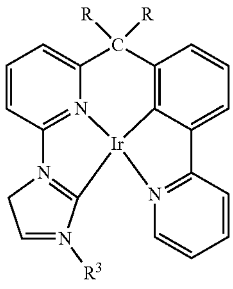
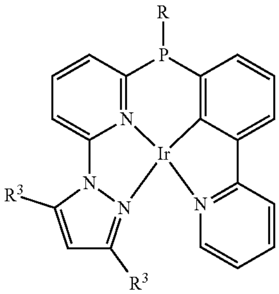
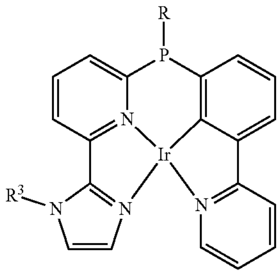
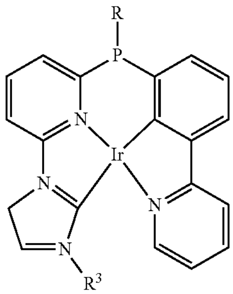
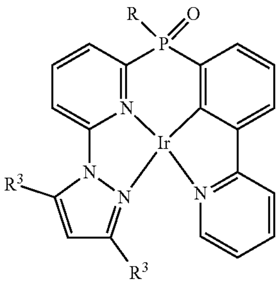
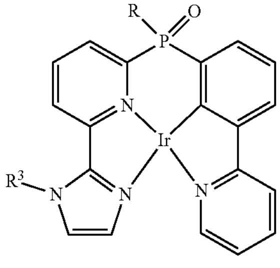
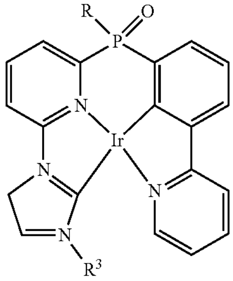
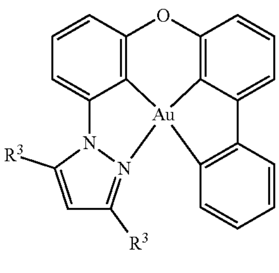

-continued
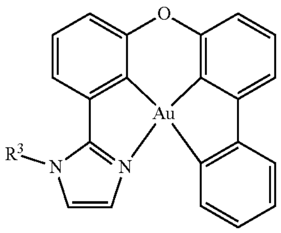
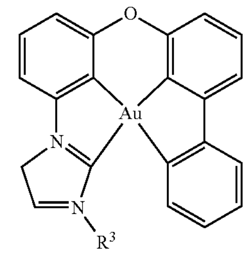
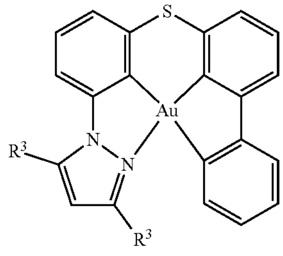
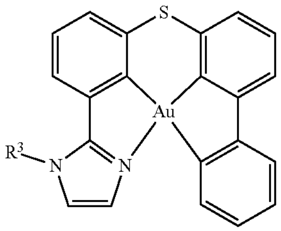
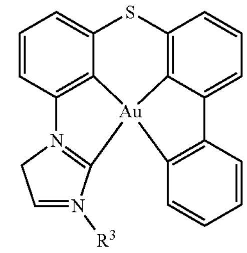
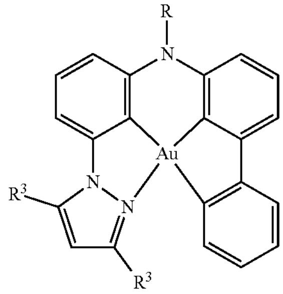
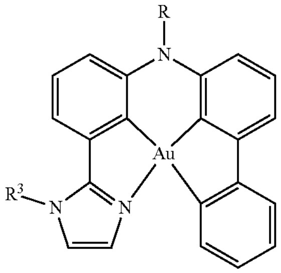
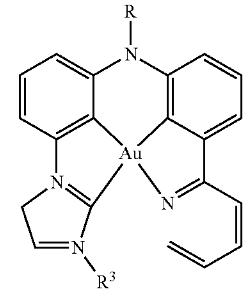
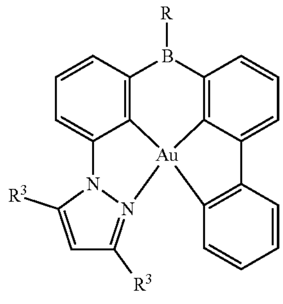
-continued
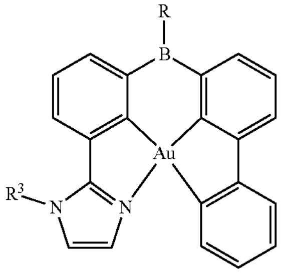
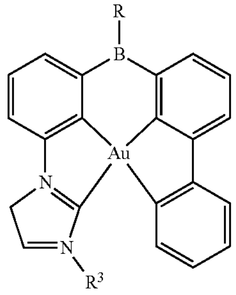
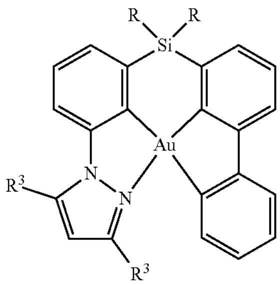
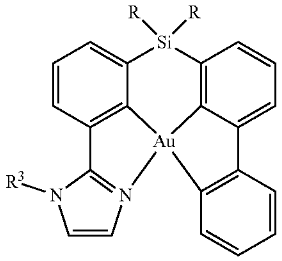
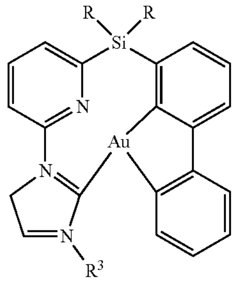
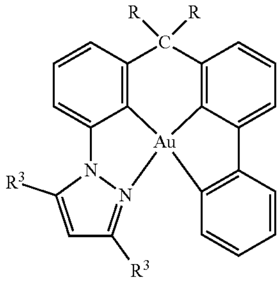
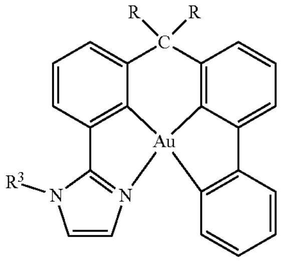
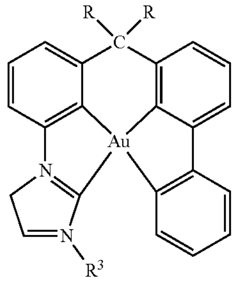
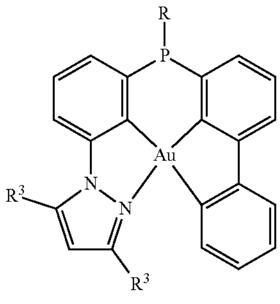

-continued
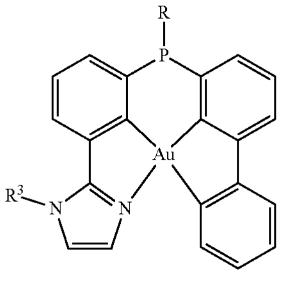
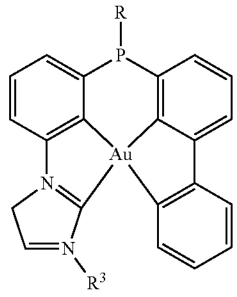
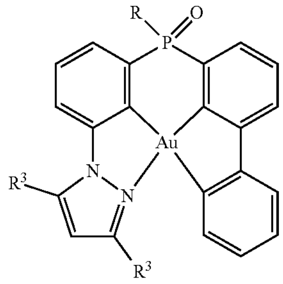
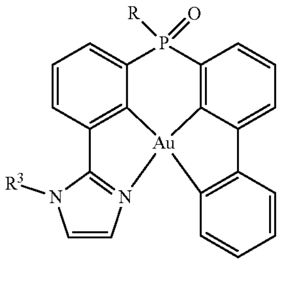
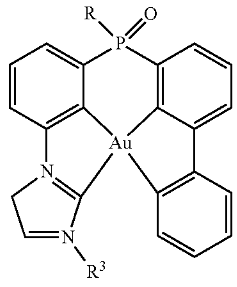
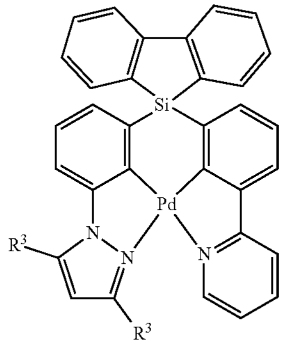
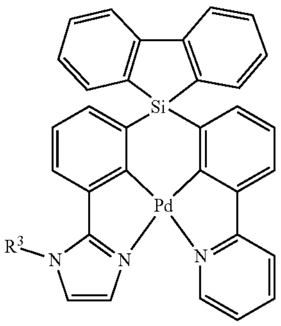
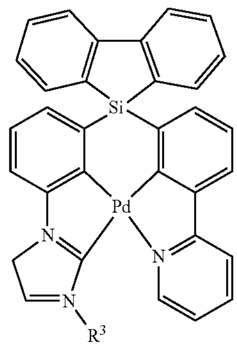
-continued
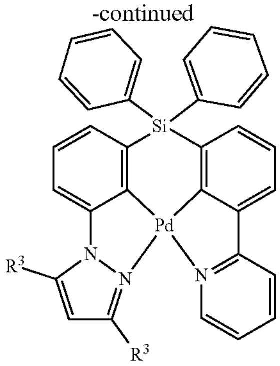
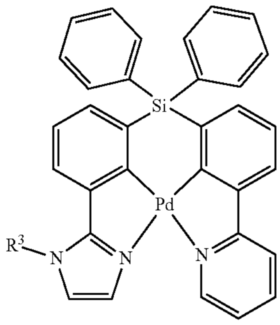
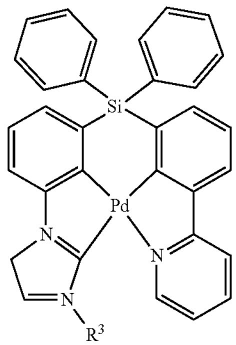
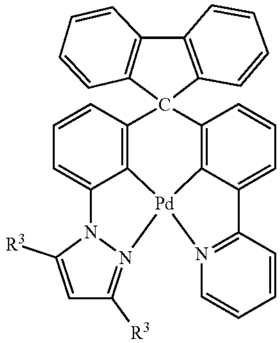
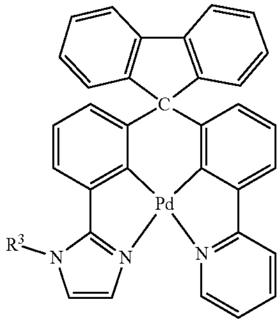
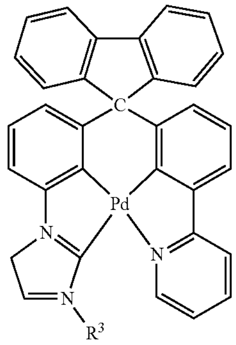
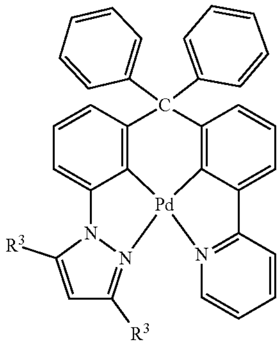

-continued
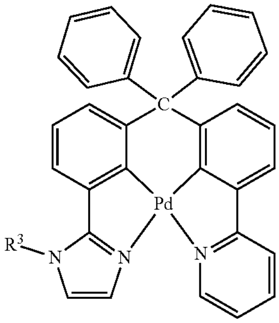
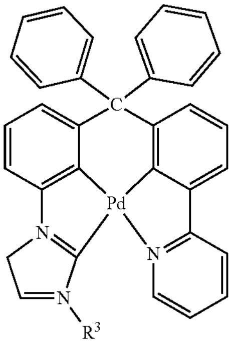
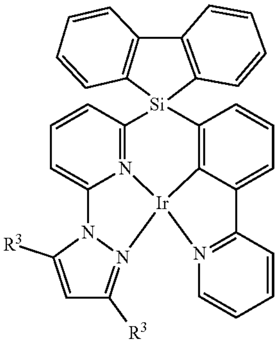
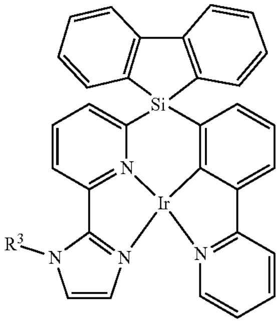
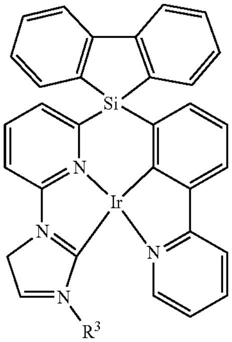
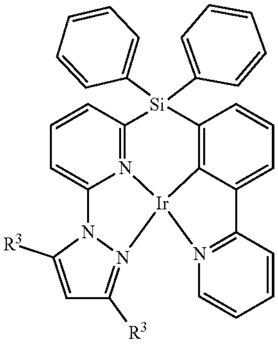
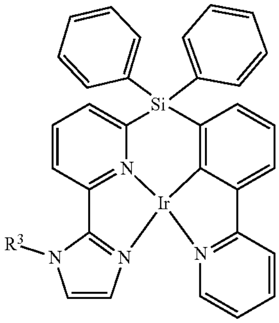
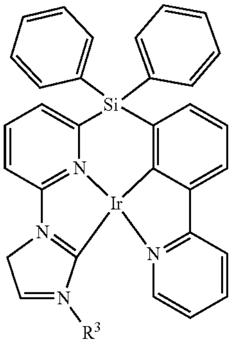
-continued
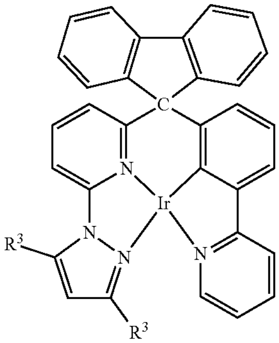
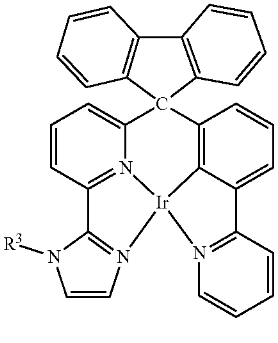
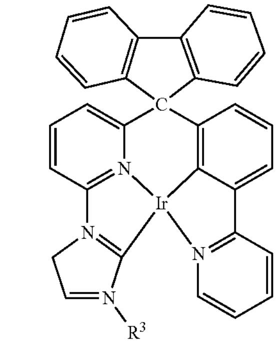
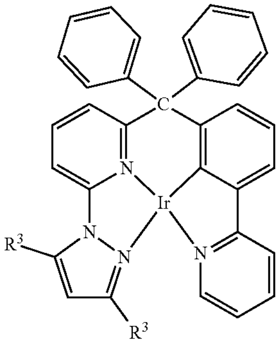
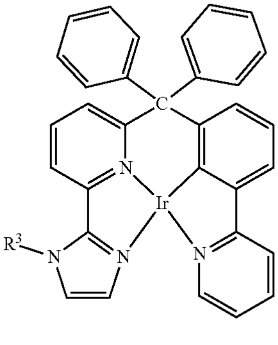
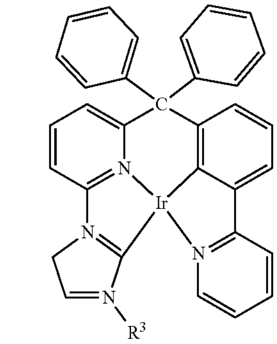
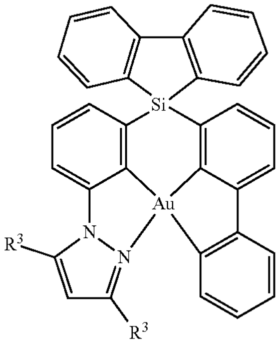

-continued
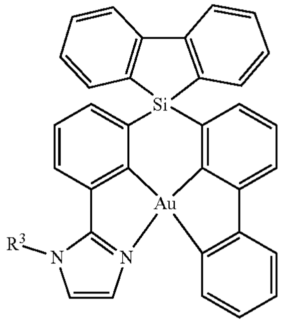
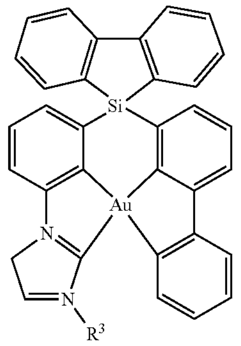
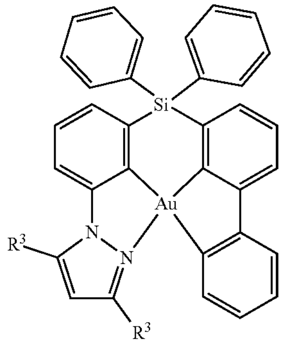
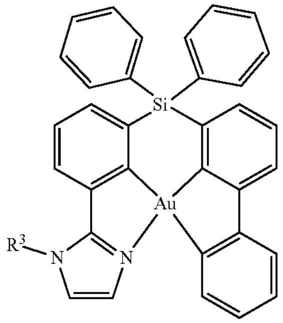
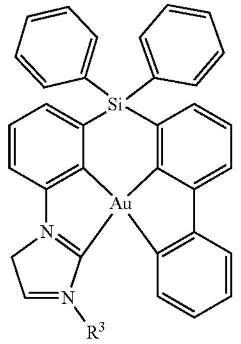
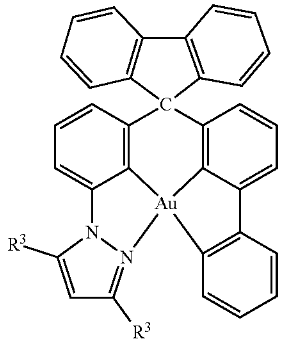
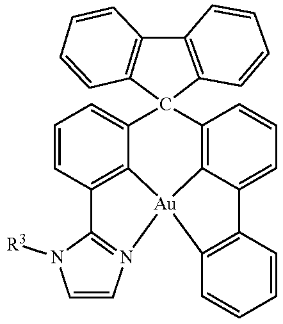
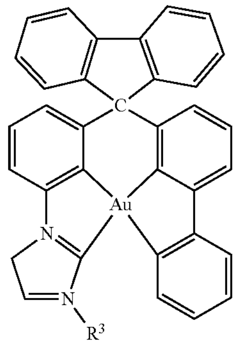
-continued
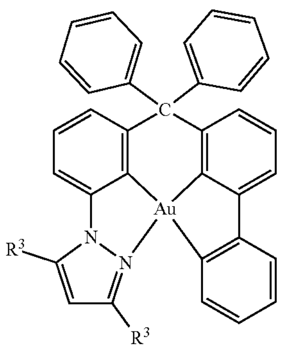
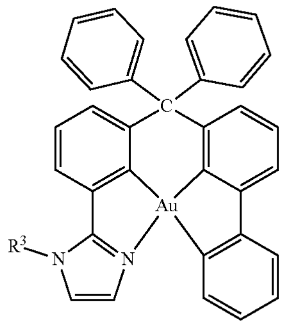
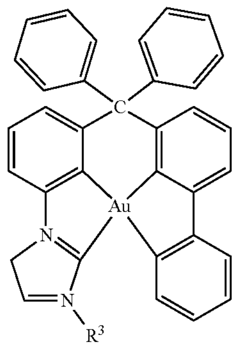
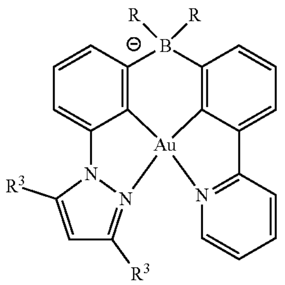
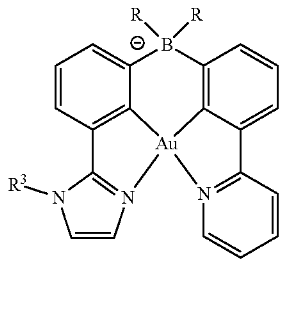
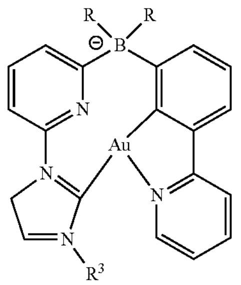
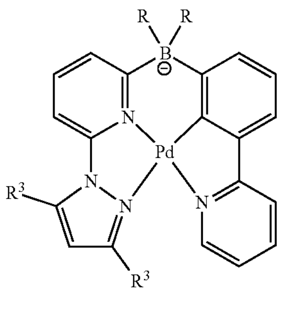

-continued

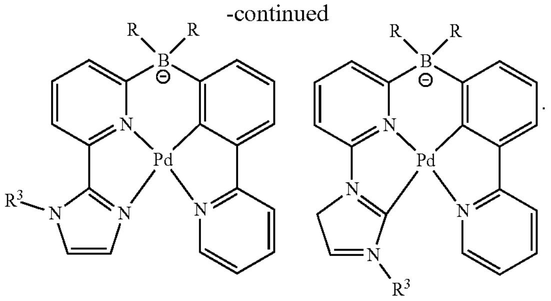

Compositions

As briefly described above, the present disclosure is directed to metal compounds. Also disclosed are compositions comprising one or more of the disclosed compounds.

Devices

As briefly described above, the present disclosure is directed to metal compounds. In one aspect, the compounds or compositions disclosed here can be used as emitters for OLED applications, such as solid state lighting.

The disclosed compounds of the present disclosure can be useful in a wide variety of applications, such as, for example, lighting devices. In a particular aspect, one or more of the compounds can be useful as host materials for an organic light emitting display device.

The disclosed compounds are useful in a variety of applications. As light emitting materials, the compounds can be useful in organic light emitting diodes (OLED) s, luminescent devices and displays, and other light emitting devices.

The energy profile of the compounds can be tuned by varying the structure of the ligand surrounding the metal center. For example, compounds having a ligand with electron withdrawing substituents will generally exhibit different properties, than compounds having a ligand with electron donating substituents. Generally, a chemical structural change affects the electronic structure of the compound, which thereby affects the electrical transport and transfer functions of the material. Thus, the compounds of the present invention can be tailored or tuned to a specific application that desires an energy or transport characteristic.

In another aspect, disclosed compound can provide improved efficiency and/or operational lifetimes in lighting devices, such as, for example, organic light emitting devices, as compared to conventional materials.

In other various aspects, the disclosed compounds can be useful as, for example, host materials for organic light emitting diodes, lighting applications, and combinations thereof.

The disclosed compounds can be made using a variety of methods, including, but not limited to those recited in the examples provided herein. In other aspects, one of skill in the art, in possession of this disclosure, could readily determine an appropriate method for the preparation of an iridium compound as recited herein.

Compounds described herein can be used in an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. The emission color of an OLED is determined by the emission energy (optical energy gap) of the light processing material 108, which can be tuned by tuning the electronic structure of the emitting compounds and/or the host material. Both the hole-transporting material in the HTL layer 106 and the electron-transporting material (s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A tetradentate Pd(II) complex, Pd3O3, which exhibits highly efficient excimer emission was synthesized and characterized as described below. Pd3O3 can achieve blue emission despite using phenyl-pyridine emissive ligands which have been a mainstay of stable green and red emitter designs, making Pd3O3 a good candidate for stable blue or white OLEDs. Pd3O3 utilizes a rigid and planar molecular design to achieve efficient blue and white emission while remaining aligned with stable molecular designs. Pd3O3 exhibits strong and efficient phosphorescent excimer emission expanding the excimer based white OLEDs beyond the sole class of Pt complexes. Devices of Pd3O3 demonstrate peak external quantum efficiencies as high as 24.2% and power efficiencies of 67.9 lm/W for white devices. Furthermore, Pd3O3 devices fabricated in a stable device structure achieved nearly 1000 h at 1000 cd/m$^2$ without any outcoupling enhancement while simultaneously achieving peak external quantum efficiencies of 19.9% and power efficiencies over 60 lm/W.

Synthesis

General Synthetic Procedure: All commercial reagents were purchased and used as received without further purification. Pd(OAc)$_2$ was purchased from Pressure Chemical Co. n-Bu$_4$NBr, CuI, 2-(tributylstannyl)pyridine and 2-picolinic acid were purchased from Sigma Aldrich. Silica gel (40-60 μm) was purchased from Agela Technologies and BDH. DMSO, toluene (low water), and acetic acid were purchased from Alfa Aesar, J. T. Baker, Fluke and BDH respectively.

All reactions were carried out under an inert $N_2$ atmosphere in oven-dried glassware. External bath temperatures were used to record all reaction temperatures. Flash column chromatography was carried out with silica gel. Proton and carbon NMR spectra ($^1H$ NMR and $^{13}C$ NMR) were recorded in dimethyl sulfoxide-$d_6$ (DMSO-$d_6$) on a Varian 400 MHz NMR spectrometer. The solvent residual peak (DMSO-$d_6$) was calibrated to 2.50 ppm for $^1H$ NMR and 39.52 ppm for $^{13}C$ NMR. Multiplicities are abbreviated as follows: s=singlet, d=doublet, dd=doublet of doublets, t=triplet, br=broad, m=multiplet.

Synthesis of 2-(3-(3-(pyridin-2-yl) phenoxy)phenyl) pyridine

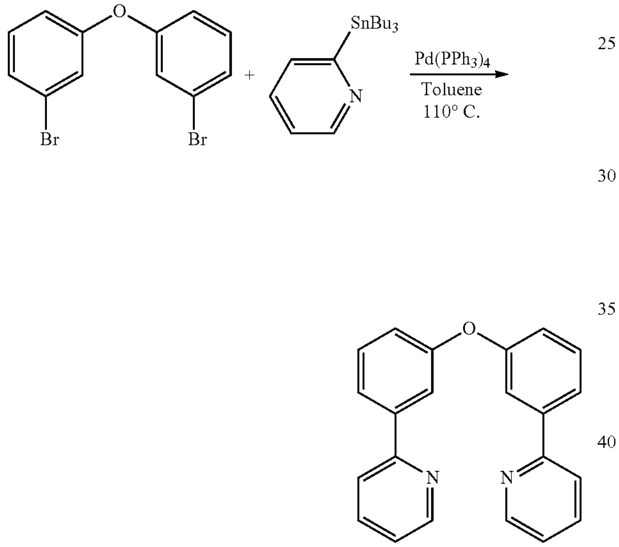

To a 100 mL three-neck round-bottom flask were added 1-bromo-3-(3-bromophenoxy)benzene (656 mg, 2 mmol) and 2-(tributylstannyl)pyridine (1.76 g, 4.8 mmol). The flask was evacuated and backfilled with nitrogen for three cycles. Tetrakis(triphenylphosphine) palladium (0) (115 mg, 0.1 mmol) and toluene (20 mL) were added under nitrogen, and the reaction mixture was stirred at 110° C. under nitrogen for 24 hours. After cooling to room temperature, the mixture was poured into 50 mL of water and extracted with ethyl acetate (3×100 mL), and the combined organic layers were dried with anhydrous $Na_2SO_4$ and concentrated under reduced pressure. Purification of the resulting residue by column chromatography (hexanes:ethyl acetate=5:1) afforded the desired product as a white solid (550 mg, 84%). $^1H$ NMR (DMSO-$d_6$, 400 MHZ): δ 7.16 (dd, J=8.0, 2.4 Hz, 2H), 7.33-7.38 (m, 2H), 7.54 (t, J=7.6 Hz, 2H), 7.79 (m, 2H), 7.85-7.91 (m, 4H), 7.98 (d, J=8 Hz, 2H), 8.63 (d, J=4.4 Hz, 2H).

Synthesis of Palladium (II) 2-(3-(3-(pyridin-2-yl) phenoxy)phenyl)pyridine

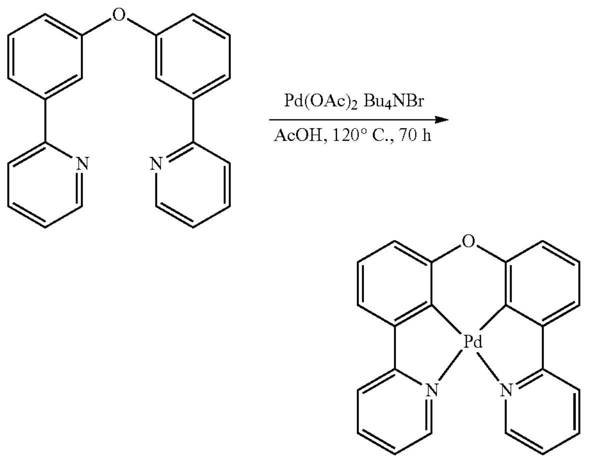

Figure 2:
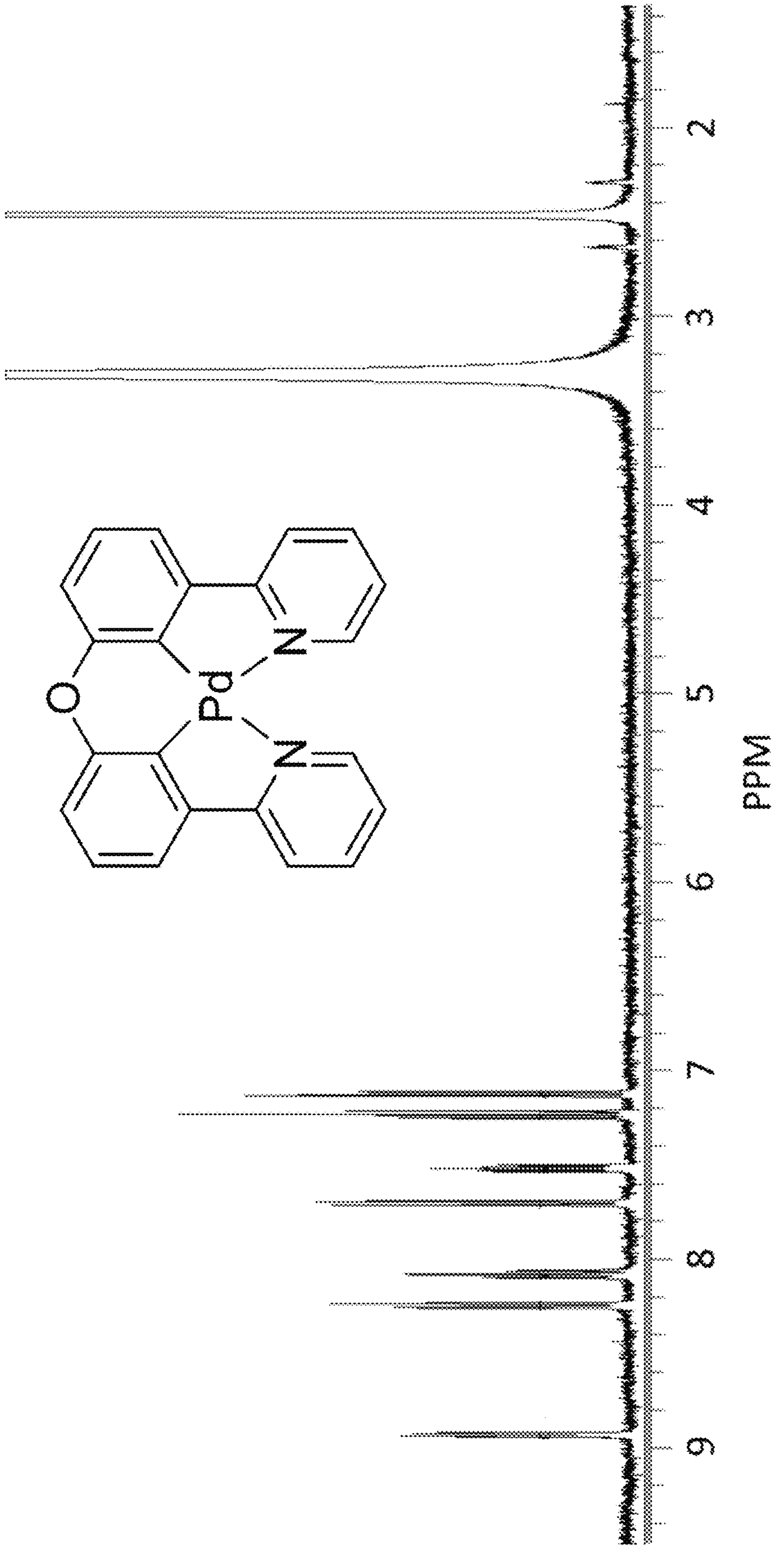
FIG. 2 shows a $^1$H NMR spectrum of Pd3O3 in DMSO-d6 at 400 MHz.

2-(3-(3-(pyridin-2-yl) phenoxy)phenyl)pyridine (470 mg, 1.45 mmol), $Pd(OAc)_2$ (348 mg, 1.55 mmol), and n-$Bu_4NBr$ (48 mg, 0.149 mmol) were added to a 100 mL three-neck round-bottom flask, then 30 mL acetic acid was added. The mixture was sparged with nitrogen for 30 minutes, then stirred at ambient temperature for 12 hours. The mixture was subsequently heated in an oil bath at a temperature of 110° C. for another 72 hours. 100 mL of water was added after the mixture was cooled down to room temperature. The resulting precipitate was collected through filtration, washed with water three times, then dried in air. The collected solid was purified through column chromatography on silica gel using dichloromethane as eluent to afford the desired Pd3O3 as a light yellow solid (390 mg, 63%). $^1H$ NMR (DMSO-d6, 400 MHz): δ 7.16 (d, J=7.6 Hz, 2H), 7.27 (dd, J=15.6, 8.0 Hz, 2H), 7.55 (dd, J=12.4, 6.4 Hz, 2H), 7.74 (d, J=7.2 Hz, 2H), 8.09-8.15 (m, 2H), 8.28 (d, J=8.4 Hz, 2H), 8.97 (d, J=5.2 Hz, 2H). MS (APCI+) m/z: [M]+ calcd for $C_{22}H_{15}ON_2OPd$ 429.0219, found 429.0232. The $^1H$ NMR spectrum of Pd3O3 (DMSO-$d_6$, 400 MHz) is shown in FIG. 2.

Devices

Materials: TAPC (di-[4-(N,N-di-toylyl-amino)-phenyl] cyclohexane), TrisPCz (9,9',9"-triphenyl-9H,9'H,9"H-3,3':6'3"-tercarbazole), 26mCPy (2,6-bis(N-carbazolyl)pyridine), DPPS (diphenyl-bis[4-(pyridin-3-yl)phenyl]silane), BmPyPB (1,3-bis[3,5-di(pyridin-3-yl)phenyl]benzene), and BPyTP (2,7-di(2,2'-bipyridin-5-yl)triphenylene) were all synthesized by methods known in the art. HATCN (1,4,5,8,9,11-hexaazatriphenylene-hexacarbonitrile), NPD (N,N'-diphenyl-N,N'-bis(1-naphthyl)-1,1'-biphenyl-4,4"-diamine), BAlq bis(2-methyl-8-quinolinolato) (biphenyl-4-olato)aluminum, and mCBP 3,3-di(9H-carbazol-9-yl)biphenyl were all provided from commercial suppliers. All materials were sublimed 1 or more times in a 4-zone thermal gradient furnace at pressures of $10^{-5}$ torr prior to use.

Device Fabrication and Characterization: Devices were fabricated on pre-patterned substrates of ITO on glass. Prior to deposition substrates were cleaned by a gentle scrub followed by subsequent sonication in water, acetone, and isopropanol. Organic layers were deposited by vacuum thermal evaporation in a custom made chamber by Travato Man. Inc. Base pressures were kept between $10^{-8}$-$10^{-7}$ torr and deposition rates were kept between 0.5-1.0 Å/s. A 1 nm LiF buffer layer was deposited at 0.2 Å/s. Al cathodes were deposited without breaking vacuum at 1-2 Å/s through a shadow mask defining a device area of 4 $mm^2$.

High efficiency devices were fabricated in the structure: ITO/HATCN (10 nm)/NPD (40 nm)/TAPC (10 nm)/x % Pt3O3:26mCPy (25 nm)/DPPS (10 nm)/BmPyPB (40 nm)/LiF/Al where x=5% or 10%. For stable devices the following structure was used: ITO/HATCN (10 nm)/NPD (40 nm)/TrisPCz (0 or 10 nm)/x % Pd3O3: Host (25 nm)/BA1q (10 nm)/BPyTP (40 nm)/LiF/Al where x=2% or 10% and the host is either 2,6 mCPy or mCBP. Current-voltage-luminance characteristics were taken with a Keithley 2400 Source-Meter and a Newport 818 Si photodiode inside a nitrogen-filled glove-box with all devices assumed to be Lambertian emitters. Accelerated lifetime testing was performed at a constant current of 20 $mA/cm^2$. EL spectra were taken at 1 $mA/cm^2$ using a calibrated ocean optics HR4000 spectrometer.

Figure 3:
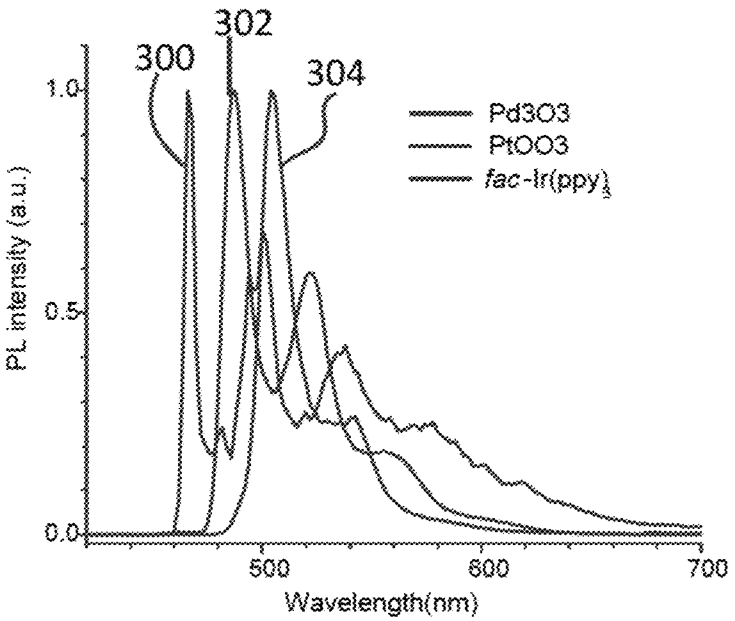
FIG. 3 shows photoluminescent spectra of Pd3O3, PtOO3, and fac-Ir(ppy)$_3$.

Low temperature emission spectra of Pd3O3 and its Pt and Ir analogs are shown in FIG. 3 as plots 300, 302, and 304, respectively. Although the three metal complexes employ the same cyclometalating ligand of phenyl pyridine, the incorporation of palladium has shifted the maximum emission wavelength of metal complexes from 504 nm for fac-Ir $(ppy)_3$ to 466 nm for Pd3O3, indicating the suitability of Pd3O3 as a phosphorescent emitter for blue and white OLED applications.

Figure 4:
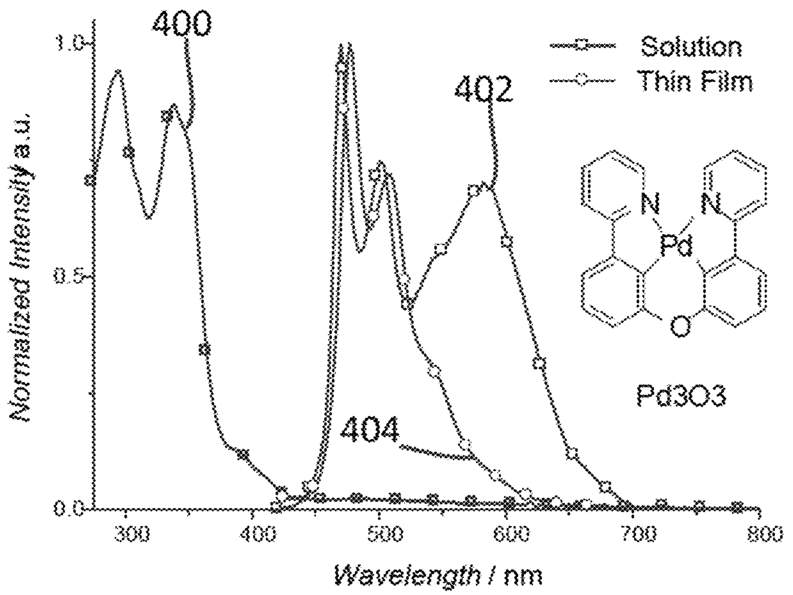
FIG. 4 shows absorption spectra of a solution of Pd3O3 in solution and in a dilute thin film.
Figure 5:
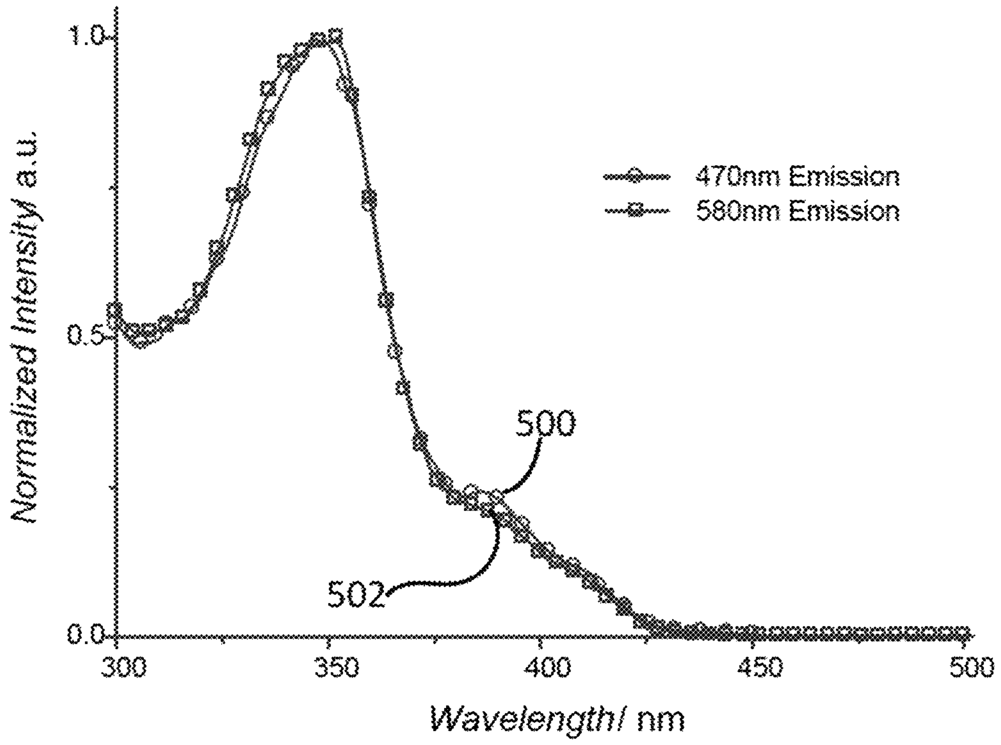
FIG. 5 shows excitation spectra of Pd3O3 in solution.

Both a dilute solution of Pd3O3 in dichloromethane (DCM) and a dilute thin film (1% by weight) of Pd3O3 in 2,6-bis(N-carbazolyl)pyridine (26mCPy) were prepared for spectral analysis. The normalized absorption and photoluminescent spectrum of the solution are shown in plots 400 and 402, respectively, and the photoluminescent spectrum of the thin film is shown in plot 404 of FIG. 4. The strong solution absorption peaks below ~360 nm are assigned to $^1\pi$-$\pi^*$ transitions, localized on the phenyl-pyridine ligands. The small shoulder in the 360-450 nm range is assigned to singlet metal to ligand charge transfer ($^1$MLCT) transitions. Both the solution and the thin film show molecular emission peaks in the 450-550 nm range. Plot 402 shows an emission onset near 450 nm with a primary emission peak at 477 nm and a second peak at 507 nm. Due to strong intermolecular interactions, all prepared solutions formed suspensions of small molecular aggregates. Consequently, plot 400 contained a large, broad aggregate emission which peaks at 582 nm. As shown in plots 500 and 502 of FIG. 5, this low energy emission band is attributed to excimer emission which is supported by the excitation spectra showing a shared origin for both the monomer and aggregate emission.

Figure 6:
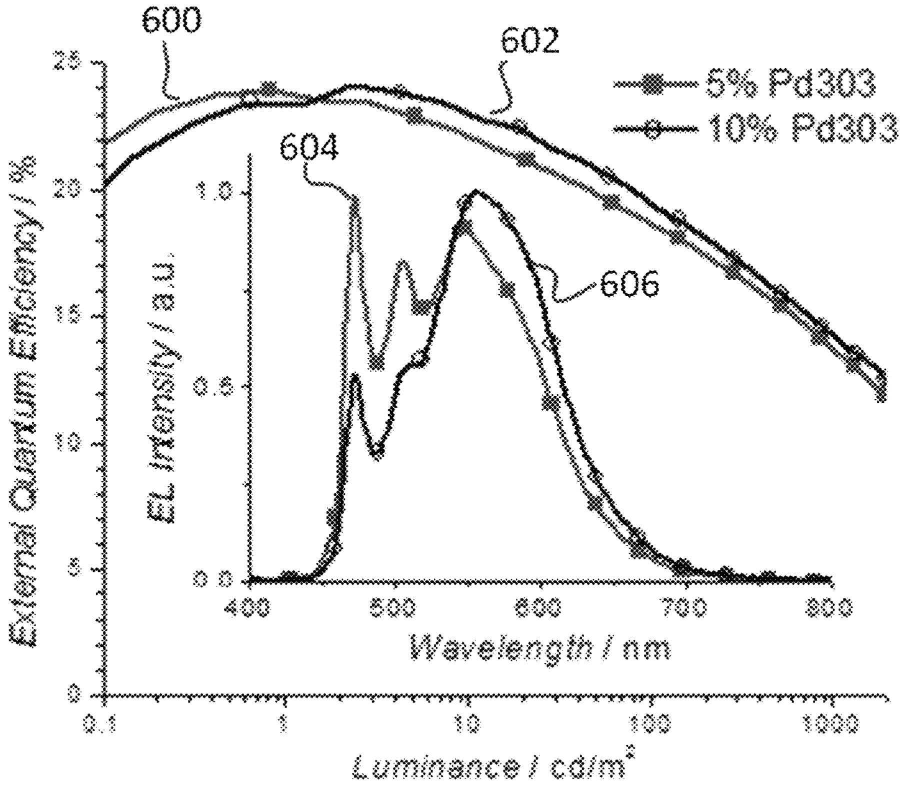
FIG. 6 shows external quantum efficiency versus luminance and electroluminescent spectra of devices with Pd3O3.

To evaluate the performance of Pd3O3 in a WOLED setting, devices were fabricated in a known efficient and charge confining structure: ITO/HATCN (10 nm)/NPD (40 nm)/TAPC (10 nm)/x % Pt3O3:26mCPy (25 nm)/DPPS (10 nm)/BmPyPB (40 nm)/LiF/Al for dopant concentrations of 5% and 10% Pt3O3 by mass. HATCN is 1,4,5,8,9,11-hexaazatriphenylene-hexacarbonitrile, NPD is N,N'-diphenyl-N,N'-bis(1-naphthyl)-1,1'-biphenyl-4,4"-diamine, TAPC is di-[4-(N,N-di-toylyl-amino)-phenyl]cyclohexane, 26mCPy is 2,6-bis(N-carbazolyl)pyridine, DPPS is diphenyl-bis[4-(pyridin-3-yl)phenyl]silane, and BmPyPB is 1,3-bis[3,5-di(pyridin-3-yl)phenyl]benzene. Plots 600 and 602 in FIG. 6 show external quantum efficiency (EQE) versus luminance for devices with 5% Pd3O3 and 10% Pd3O3, respectively, with high peak EQEs of 23.9% and 24.2%. Plot 600 shows an efficiency of the 5% doped device of 18.5% at 100 $cd/m^2$ and 13.8% at 1000 $cd/m^2$. Plot 602 shows an efficiency of the 10% doped device of 19.3% at 100 $cd/m^2$ and 14.3% at 1000 $cd/m^2$. This roll off may be due at least in part to the combination of charge balance at the high current density and the long PL emission lifetimes of many palladium complexes (in the range of tens and hundreds of microseconds or even longer).

Plots 604 and 606 show electroluminescent spectra for devices with 5% Pd3O3 and 10% Pd3O3, respectively, with a monomer emission peak at 472 nm and a broad excimer peak at 550-600 nm. As shown in plot 604, the excimer peak and monomer peak are of approximately equal height, yielding warm white light with CIE coordinates of (0.34, 0.47) and CRI of 53. As shown in plot 606, when the concentration of Pd3O3 is increased to 10% dopant concentration, the excimer emission broadens and increases to approximately twice the height of the monomer emission. Consequently, the emission is orange with CIE coordinates of (0.39, 0.50) and a CRI of 52. It should also be noted that the monomer to excimer emission balance occurs at a much lower dopant concentration than many of the reported platinum complexes, yielding an emission spectrum with non-ideal CIE coordinates. This may be due to the preferential stacking of Pd3O3 molecules which was also reflected in the poor solubility of Pd3O3. Furthermore, the excimer emission drops off rapidly at 600 nm, missing a significant portion of the red spectrum leading in part to the low CRI. Modifying the planar geometry nature of Pd3O3 molecules by adding steric substituents or using bulky bridging ligands may allow stronger molecular interaction between emissive materials and the host molecules and allow tuning of the monomer and excimer emission colors to yield more ideal white color.

Figure 7A:
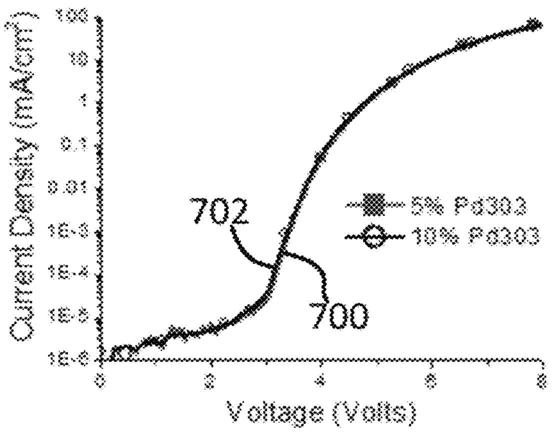
FIGS. 7A and 7B show current density-voltage characteristics and power efficiency, respectively, of devices with Pd3O3.
Figure 7B:
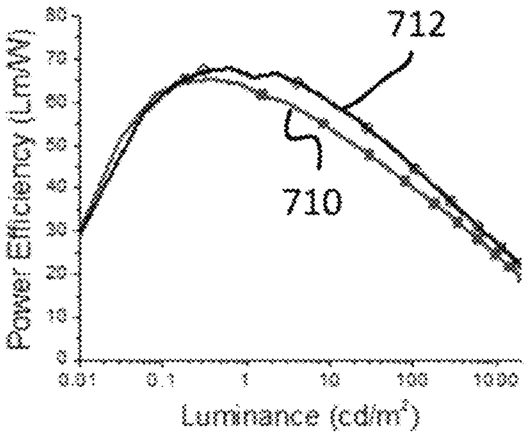

Plots 700 and 702 in FIG. 7A show current density versus voltage for Pd3O3 devices with 5% and 10% dopant concentration, respectively. Plots 710 and 712 in FIG. 7B show peak power efficiencies (PE) of 65.3 lm/W and 67.9 lm/W for Pd3O3 devices with 5% and 10% dopant concentration, respectively.

Due to the known instability of the TAPC and DPPS blocking materials, separate Pd3O3 devices were fabricated in four different stable device structures:

Device 1: ITO/HATCN/NPD/TrisPCz/10% Pd3O3:mCBP/BA1q/BPyTP/LiF/Al

Device 2: ITO/HATCN/NPD/10% Pd3O3:mCBP/BA1q/BPyTP/LiF/Al

Device 3: ITO/HATCN/NPD/TrisPCz/10% Pd3O3:26mCPy/BA1q/BPyTP/LiF/Al

Figure 8A:
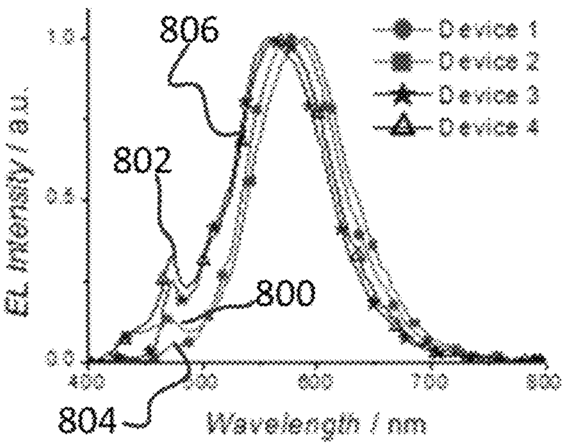
FIGS. 8A-8D show electroluminescent spectra, external quantum efficiency, power efficiency, and operational lifetimes, respectively, of devices with Pd3O3.
Figure 8B:
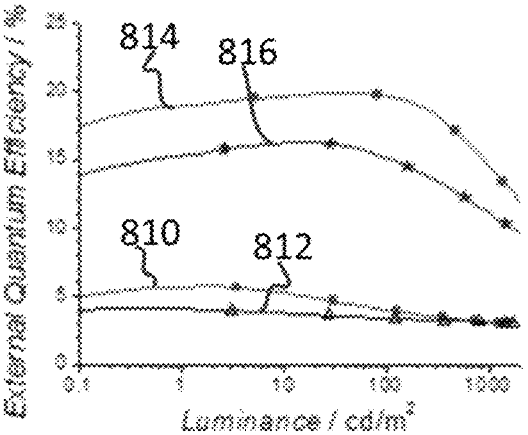
Figure 8C:
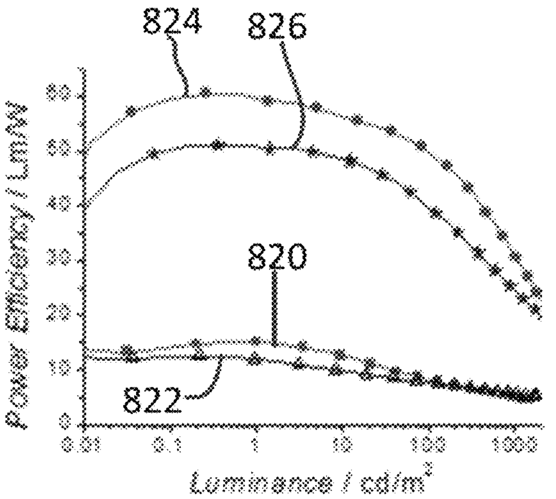

Device 4: ITO/HATCN/NPD/10% Pd3O3:26mCBP/BA1q/BPyTP/LiF/Al, where TrisPCz is 9,9',9"-triphenyl-9H,9'H,9"H-3,3': 6'3"-tercarbazole, mCBP is 3,3-di(9H-carbazol-9-yl)biphenyl, BA1q is bis(2-methyl-8-quinolinolato) (biphenyl-4-olato)aluminum, and BPyTP is 2,7-di(2,2'-bipyridin-5-yl)triphenylene. The devices were fabricated with a fixed dopant concentration of 10% in order to study the stability of OLEDs with emission originating primarily from the Pd3O3 emitters. As seen in FIG. 8A, the resulting spectra are dominated by the broad excimer emission, due at least in part to excimer formation at a moderate dopant concentration to achieve a balanced spectrum. Devices 2 and 4 had no TrisPCz blocking layer, while Devices 1 and 3 had TrisPCz. As shown in plots 800 and 802, Device 2 and Device 4 had significant emission in the 400-450 nm range. This indicates a partial NPD emission due to possible electron leakage or exciton energy transfer to the hole-transporting NPD layer. Plots 810 and 812 in FIG. 8B show low peak EQEs in the range of 4-6% for Devices 2 and 4, respectively. However, Devices 1 and 3 were very efficient. As shown in plot 814 in FIG. 8B, Device 1 reached a peak EQE of 19.9%. As shown in plot 824 in FIG. 8C, Device 1 had a peak power efficiency of 60.5 lm/W. As shown in plot 816 in FIG. 8B, Device 3 reached a peak EQE of 16.2%. As shown in plot 826 in FIG. 8C, Device 3 reached a peak power efficiency of 51.2 lm/W. The roll-off for these devices was also less significant than for the previous efficient structures. Referring back to plots 814 and 816 in FIG. 8B, Device 1 and Device 3 had EQE values of 14.6% and 11.1% at 1000 cd/$m^2$, respectively.

Figure 8D:
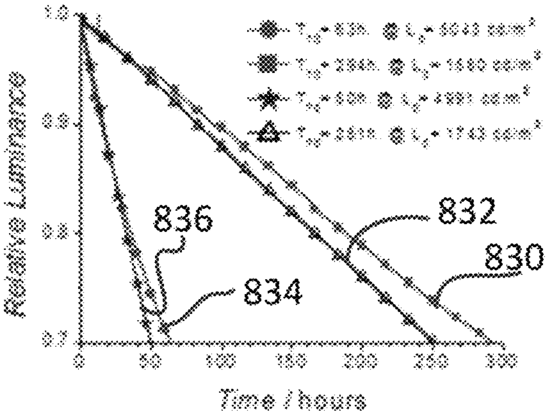

The device operational lifetimes of all four stable devices were measured at accelerated conditions by driving the devices at a constant current of 20 mA/$cm^2$. As shown in plot 830 in FIG. 8D, Device 2 demonstrated a long operational lifetime to 70% of initial luminance ($LT_{70}$) of 294 h at an initial luminance of 1560 cd/$m^2$. As shown in plot 832 in FIG. 8D, Device 4 demonstrated an operational lifetime to 70% of initial luminance ($LT_{70}$) of 251 h at an initial luminance of 1743 cd/$m^2$. When TrisPCz was used, the device operational lifetimes dropped due to possible charge build up at the interface of EML/EBL. Nevertheless, moderately high operational lifetimes were achieved. As shown in plots 834 and 836 in FIG. 8D, the operational lifetimes for Devices 1 and 3, respectively, were 63 h at 5043 cd/$m^2$ and 50 h at 4991 cd/$m^2$. Furthermore, approximating these accelerated testing results at practical luminance of 1000 cd/$m^2$ yields lifetimes of 986 h for Device 1 and 769 h for Device 3, respectively. These high lifetimes (close to 1000 h) and high power efficiency (close to 30 lm/W without any outcoupling enhancement) at practical luminance, approaches the minimum commercialization requirement with appropriate lamination quality. Furthermore, with incorporation of light outcoupling techniques, doubling the luminance at a given driving condition could be reasonably expected to yield lifetimes in the range of 2500-3500 h at 1000 cd/$m^2$.

Devices 5 and 6 were also fabricated:

Device 5: ITO/HATCN/NPD/TrisPCz/2% Pd3O3:mCBP/BA1q/BPyTP/LiF/Al

Figure 9:
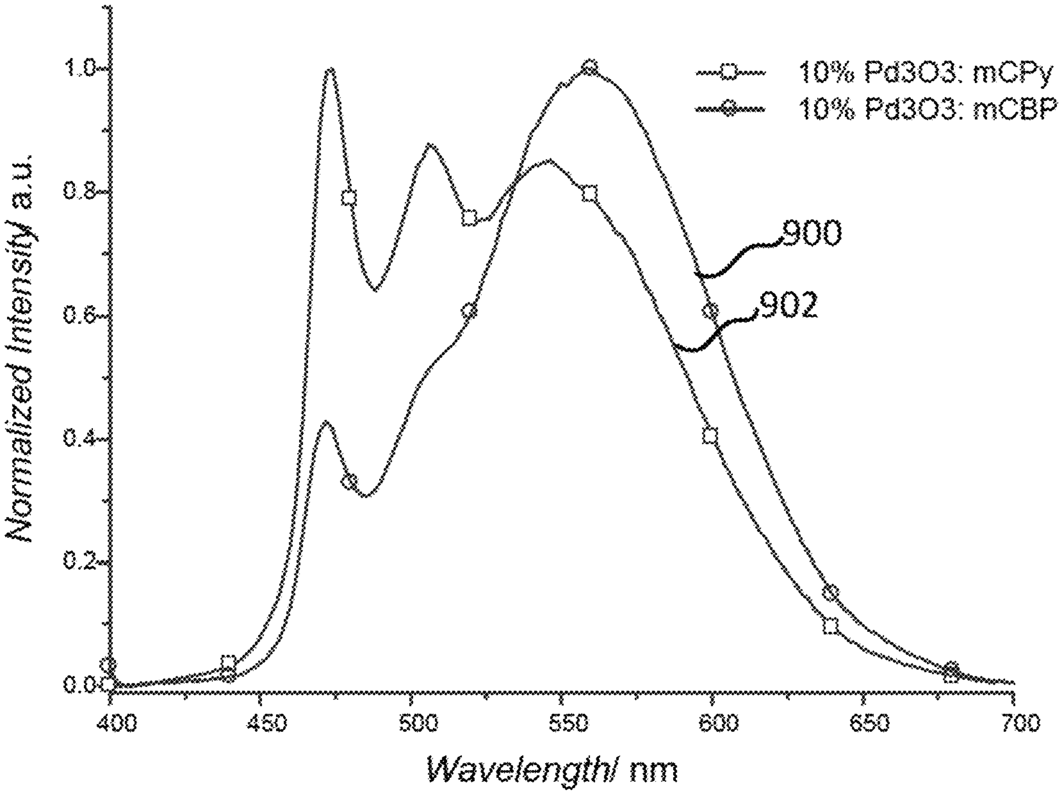
FIG. 9 shows photoluminescent spectra of doped thin films of Pd3O3.

Device 6: ITO/HATCN/NPD/2% Pd3O3:mCBP/BA1q/BPyTP/LiF/Al.

Where mCBP was selected as a host for both higher efficiencies and longer operational lifetimes, excimers were found to form more readily in mCBP than mCPy. This is shown in plots 900 and 902 in FIG. 9, which normalized intensity for devices with 10% Pd3O3 in mCBP and 10% Pd3O3 in mCPy, respectively. This difference may be due to a solid solubility effect, requiring a low concentration of 2% to balance the emission.

Figure 10:
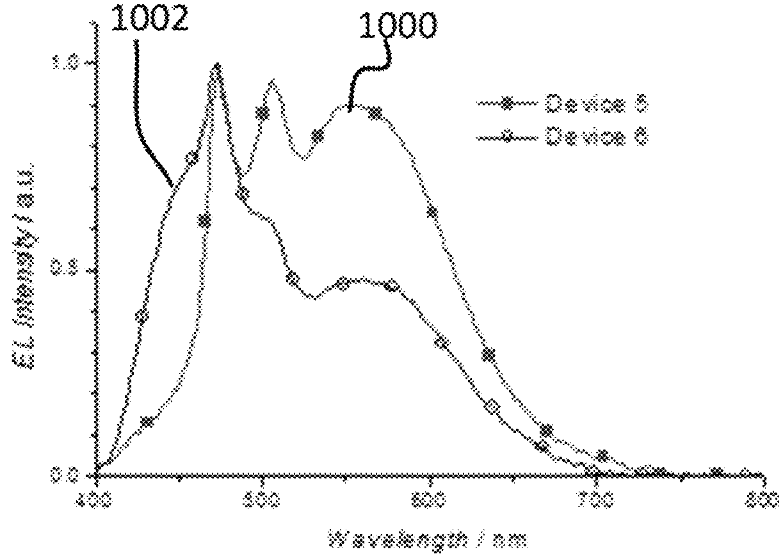
FIG. 10 shows electroluminescent spectra of Pd3O3 devices.

The resulting emission spectra are shown in FIG. 10. In plot 1000, Device 5, with a TrisPCz blocking layer, showed a nearly balanced emission spectrum resulting in color coordinates of (0.33, 0.44) and a CRI of 63. There is also emission in the 400-450 nm range that was not present in the 10% doped devices indicating some leakage processes in this device. As shown in plot 1130 in FIG. 11D, the consequence is a peak efficiency of only 5.4%. As shown in plot 1002 in FIG. 10, Device 6, which has no TrisPCz blocker, has an emission between 400-450 that increases substantially due at least in part to energy transfer into the NPD layer. As shown in plot 1132 in FIG. 11D, this drops the peak efficiency to 1.8%. However, the additional blue emission did improve the CRI to 80 and CIE coordinates of (0.27, 0.30).

Figure 11A:
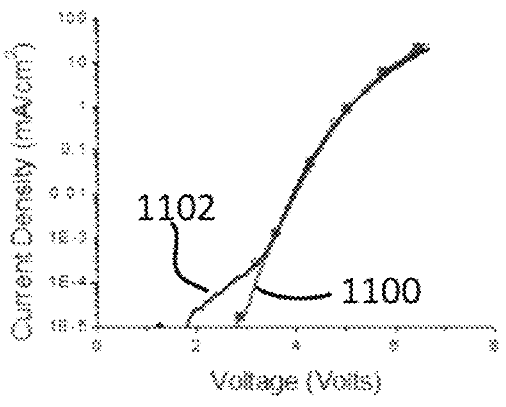
FIGS. 11A-11D show current density-voltage characteristics, operational lifetimes, power efficiency, and external quantum efficiency, respectively, of devices with Pd3O3.
Figure 11B:
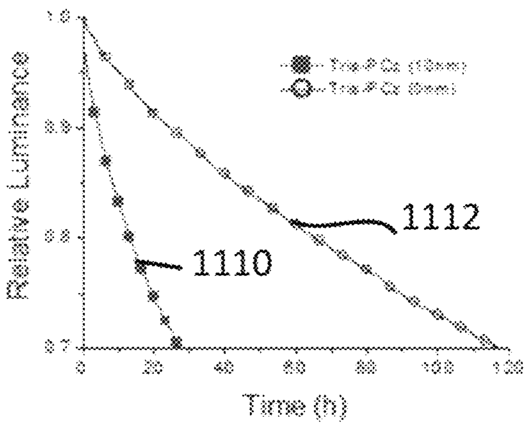
Figure 11C:
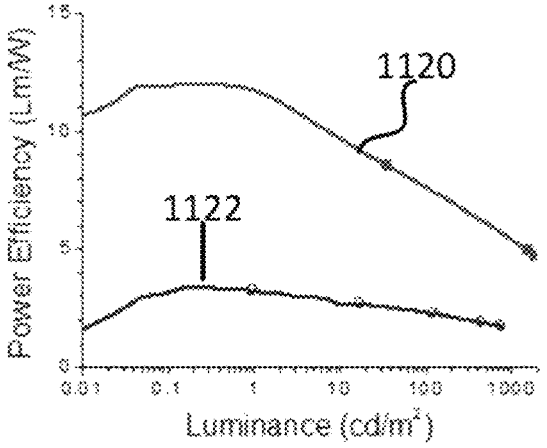
Figure 11D:
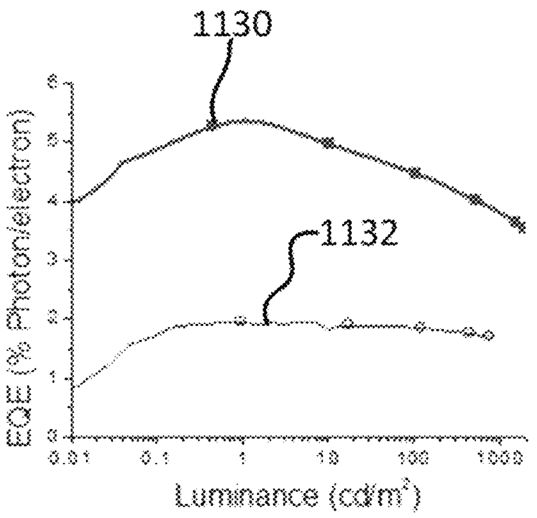

Plots 1100 and 1102 in FIG. 11A show current density versus voltage for Devices 5 and 6, respectively. Plots 1120 and 1122 in FIG. 11C show power efficiency versus luminance for Devices 5 and 6, respectively. As shown in FIG. 11C, the peak power efficiency of Device 5 is about 12.1 lm/W, and the peak power efficiency of Device 6 is about 3.3 lm/W.

The device operational lifetime at accelerated testing conditions of 20 mA/$cm^2$ were also collected for these 2% doped devices. Plot 1110 in FIG. 11B shows a resulting $LT_{70}$ for Device 5 of 28 h. Plot 1112 in FIG. 11B shows a $LT_{70}$ for Device 6 of 117 h. This is nearly a third of those with a 10% dopant concentration. Approximated lifetimes at 1000 cd/$m^2$ are only 86 h and 70 h for Devices 5 and 6, respectively. These results reflect the challenge in balancing color, efficiency, and operational stability when molecular aggregation is too favorable and the optimal emission color of white OLED is realized at a low dopant concentration.

Table 1 summarizes the device performance of Devices 1-6 as described herein.

TABLE 1

Summary of device performance for stable devices of Pd3O3

| | | | EQE (%) | | PE (lm/W) | | $L_0$ | $LT_{70}$ | |
|---|---|---|---|---|---|---|---|---|---|
| Device | CRI | CIE | peak | 1000 cd/$m^2$ | peak | 1000 cd/$m^2$ | (cd/$m^2$) | @$L_0$ | @1000 cd/$m^2$ |
| 1 | 48 | (0.48, 0.50) | 19.9 | 14.6 | 60.5 | 30.8 | 5043 | 63 | 986 |
| 2 | 57 | (0.47, 0.46) | 5.7 | 3.1 | 15.1 | 5 | 1560 | 294 | 626 |
| 3 | 48 | (0.42, 0.52) | 16.2 | 11.1 | 51.2 | 24.5 | 4991 | 50 | 769 |
| 4 | 56 | (0.41, 0.48) | 4.1 | 3.1 | 12.5 | 5.7 | 1743 | 251 | 645 |
| 5 | 63 | (0.33, 0.44) | 5.4 | 3.8 | 12 | 5.4 | 1930 | 28 | 86 |
| 6 | 80 | (0.27, 0.30) | 1.9 | — | 3.4 | — | 740 | 117 | 70 |

Figure 12:
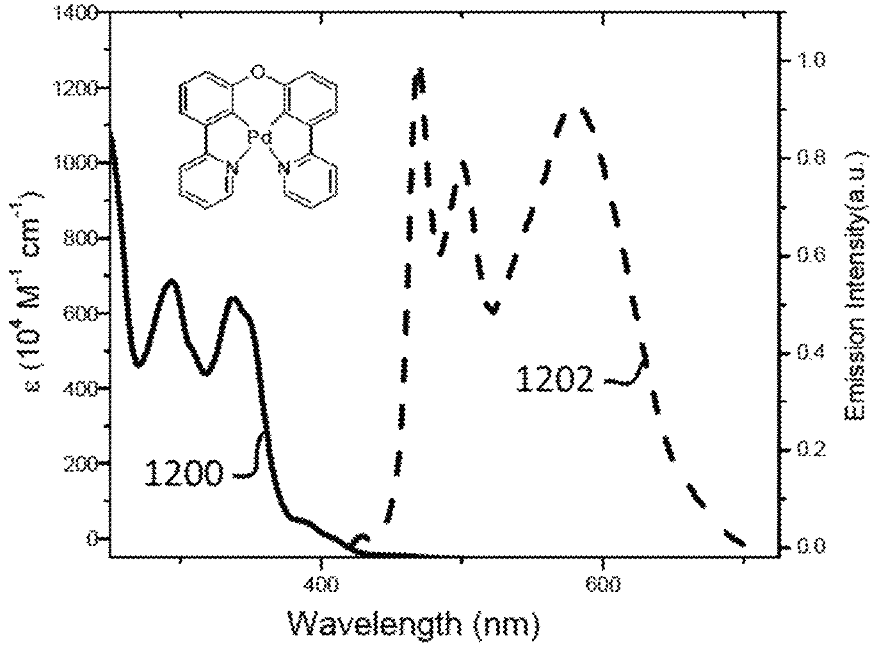
FIG. 12 shows an absorption spectrum and an emission spectrum of Pd(II) 2-(3-(3-pyridin-2-yl) phenoxy)phenyl) pyridine.

Pd3O3 was tested as an emitter in a device having the following structure: ITO/HATCN (10 nm)/NPD (40 nm)/TrisPCZ (10 nm)/Pd3O3:mCBP (25 nm)/mCBT (8 nm)/BPyTP (40 nm)/LiF/Al. Plots 1200 and 1202 in FIG. 12 show electroluminescence spectra of this device and a device using mCPy as a host material, respectively.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A compound of General Formula I:

General Formula I

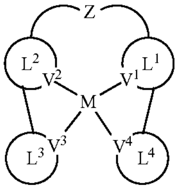

wherein:

M is $Pd^{2+}$, $Ir^{+}$, $Rh^{+}$, or $Au^{3+}$;

each of $V^1$, $V^2$, $V^3$, and $V^4$ is coordinated to M and is independently N, C, P, B, or Si;

each of $L^1$, $L^2$, $L^3$, and $L^4$ is independently a substituted or unsubstituted aryl, cycloalkyl, cycloalkenyl, heterocyclyl, heteroaryl, carbene, or N-heterocyclic carbene;

wherein at least one of $L^1$, $L^2$, $L^3$, and $L^4$ comprises the N-heterocyclic carbene of a formula:

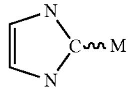

that is bonded to M by way of the wavy line; and

Z is O, S, NR, $CR_2$, $SiR_2$, BR, PR,

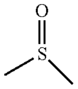 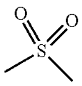 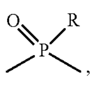, or 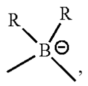, where each R is independently substituted or unsubstituted $C_1$-$C_4$ alkyl or substituted or unsubstituted aryl.

2. The compound of claim 1, wherein the compound has the following structure:

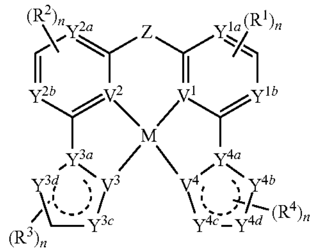

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 3, valency permitting; and each of $Y^{1a}$, $Y^{2a}$, $Y^{1b}$, $Y^{2b}$, $Y^{3a}$, $Y^{3c}$, $Y^{3d}$, $Y^{4a}$, $Y^{4b}$, $Y^{4c}$, $Y^{4d}$ is independently N, $NR^{4a}$, or $CR^{4b}$, where each $R^{4a}$ and $R^{4b}$ is independently hydrogen, hydroxyl, amino, nitro, thiol, or substituted or unsubstituted $C_1$-$C_4$ alkyl, alkoxy, or aryl.

3. The compound of claim 2, wherein the compound has one of the following structures:

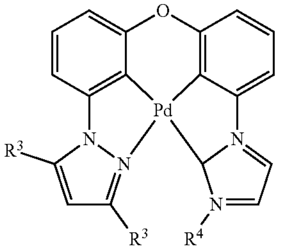

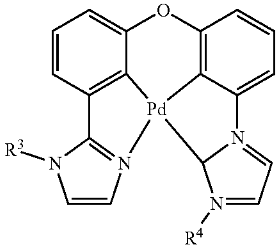 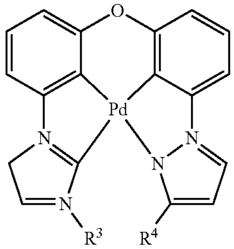

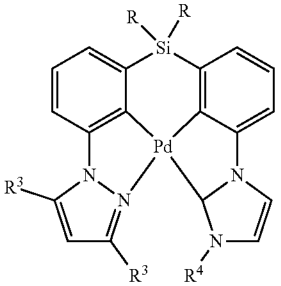

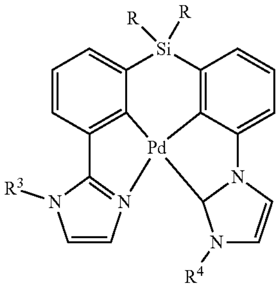 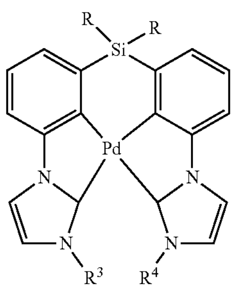

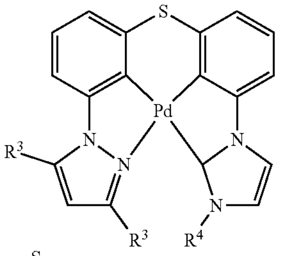

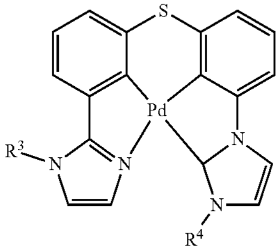 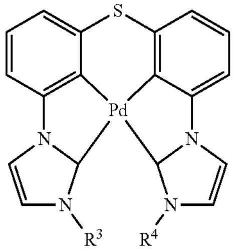

-continued
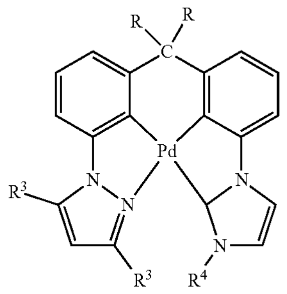
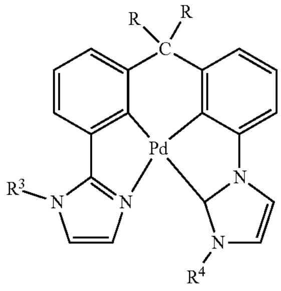
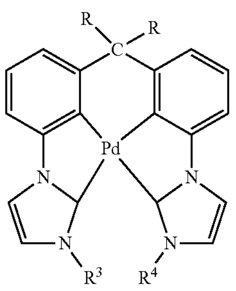
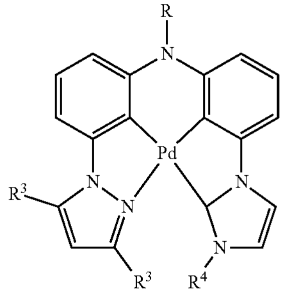
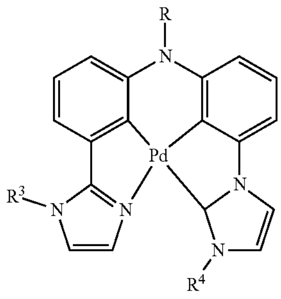
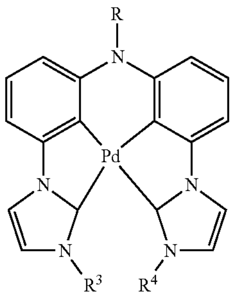
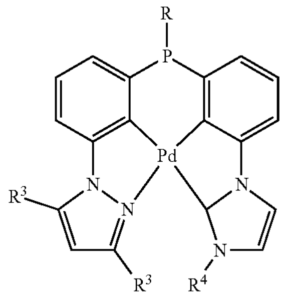
-continued
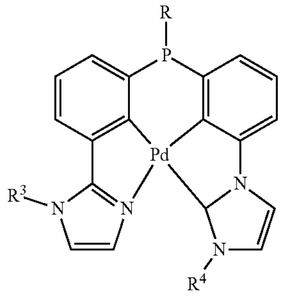
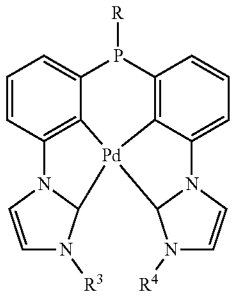
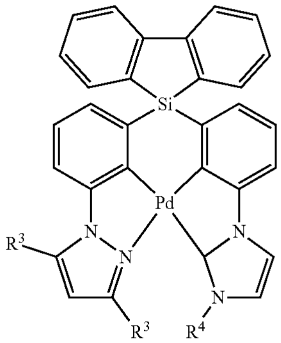
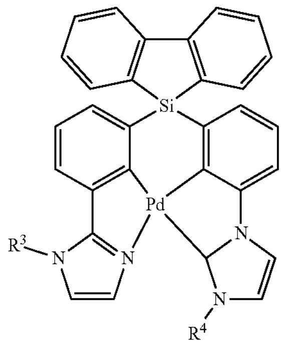
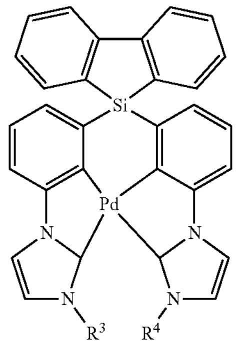
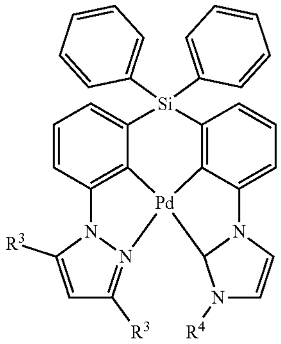
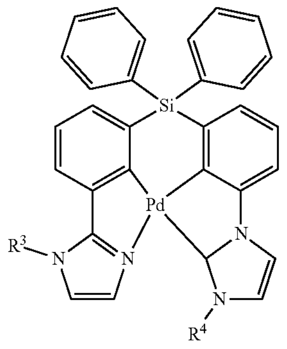
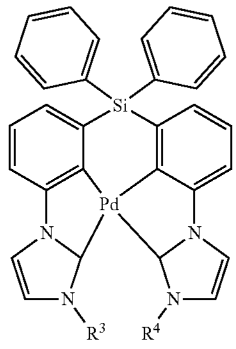

-continued
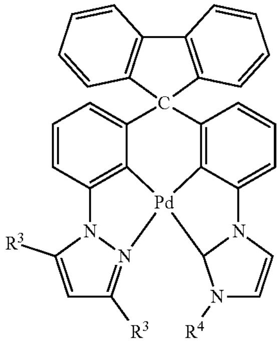
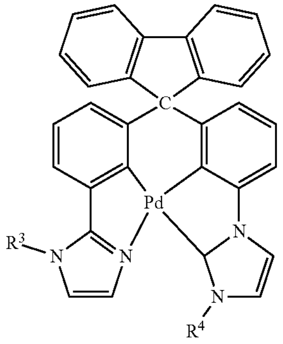
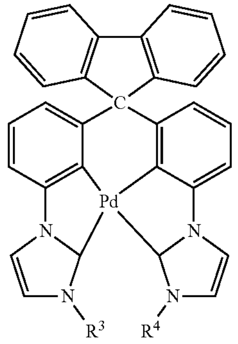
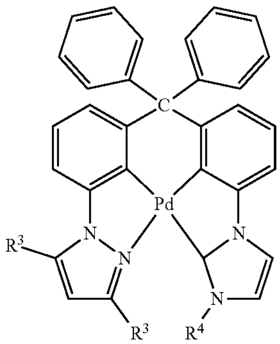
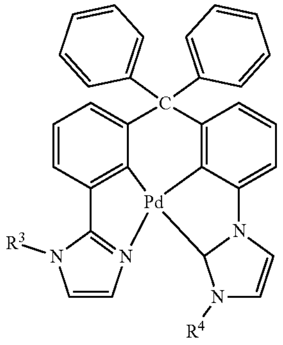
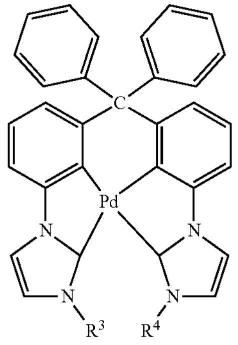
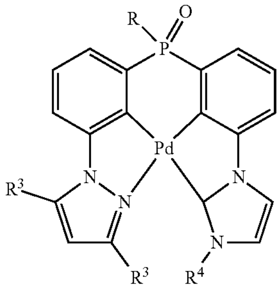
-continued
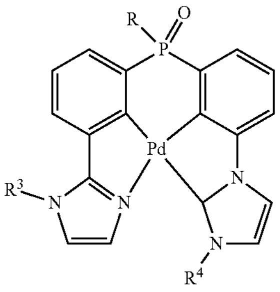
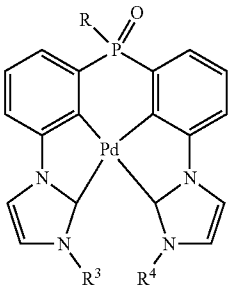
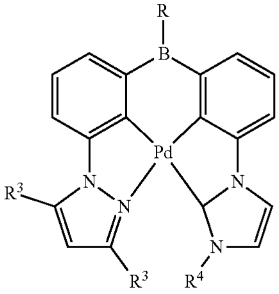
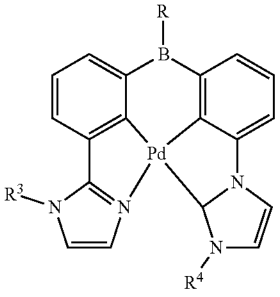
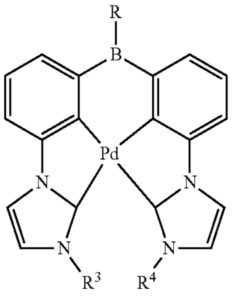
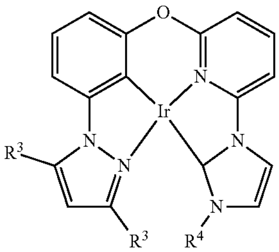
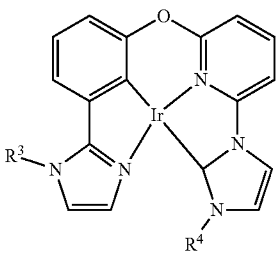
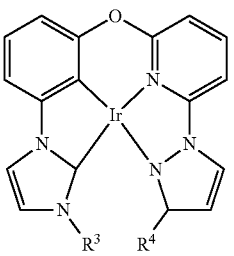
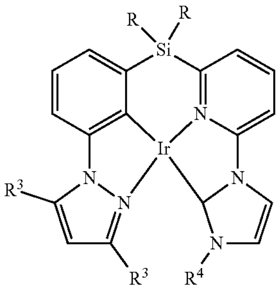

-continued
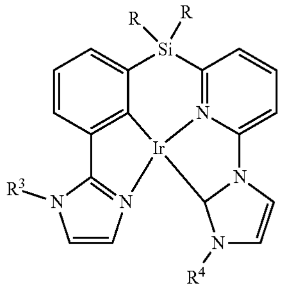
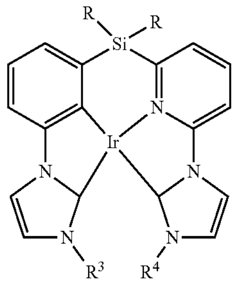
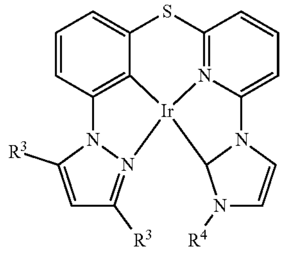
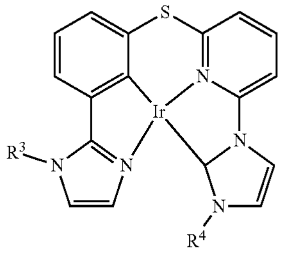
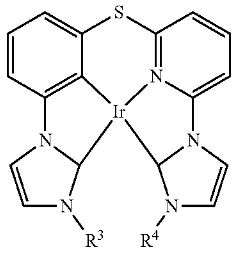
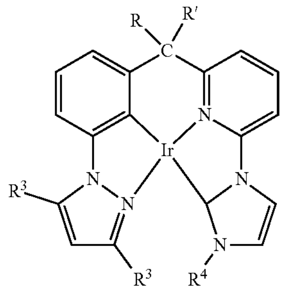
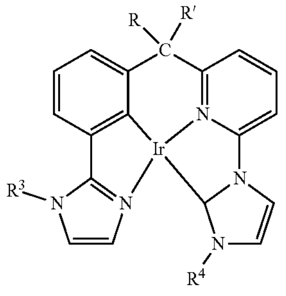
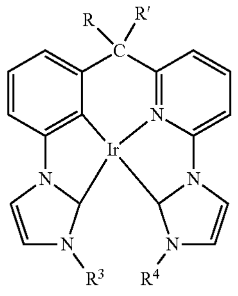
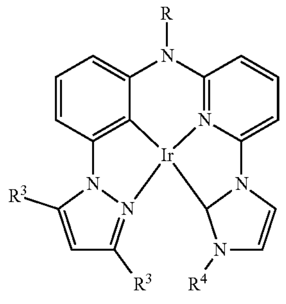
-continued
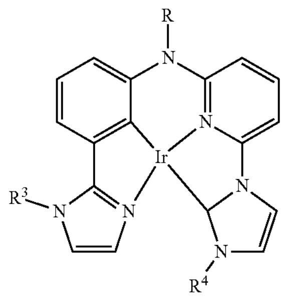
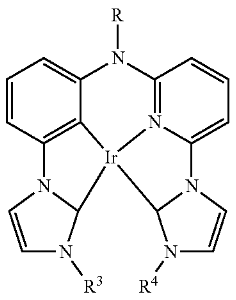
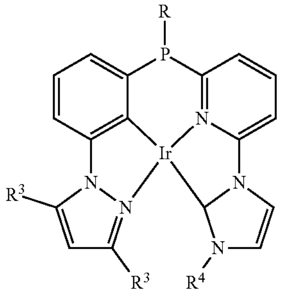
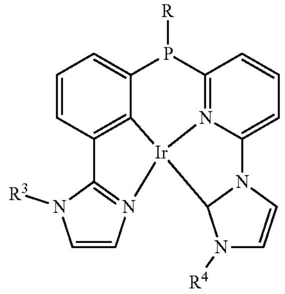
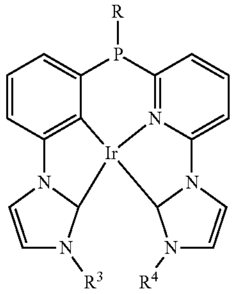
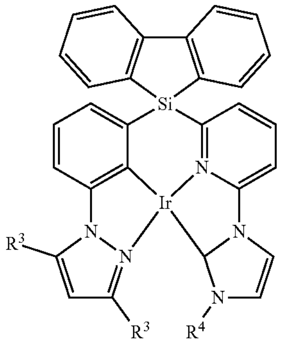
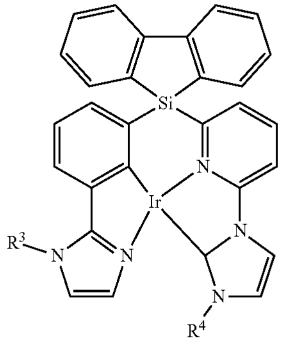
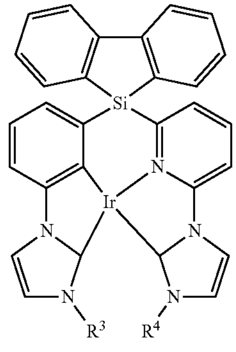

-continued
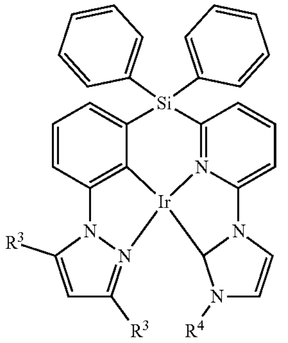
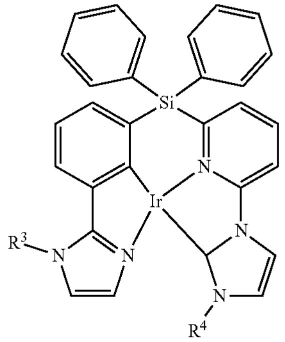
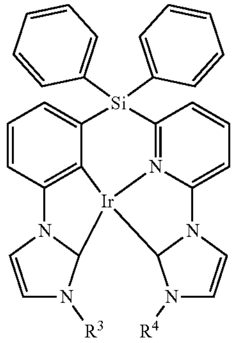
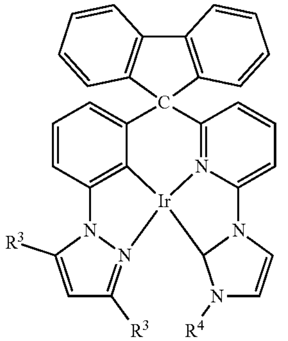
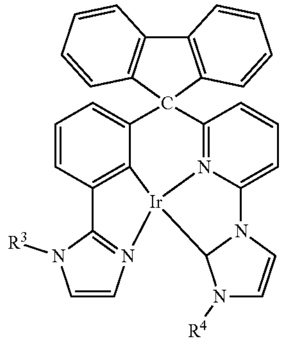
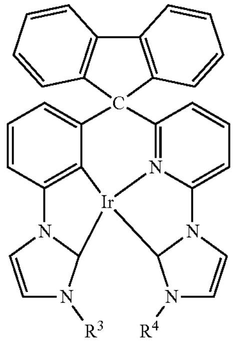
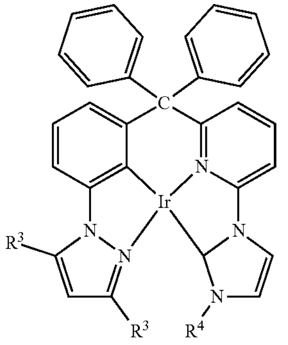
-continued
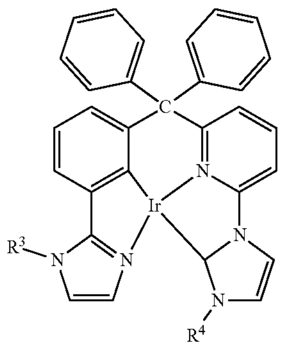
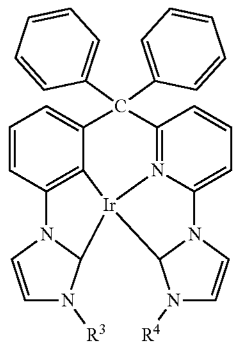
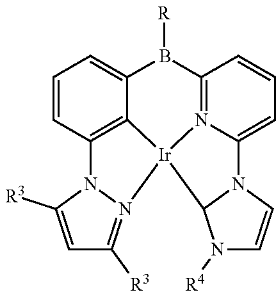
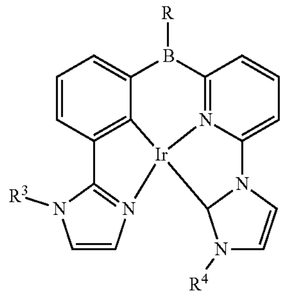
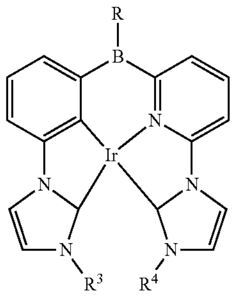
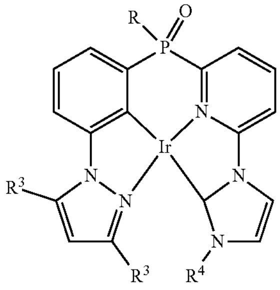
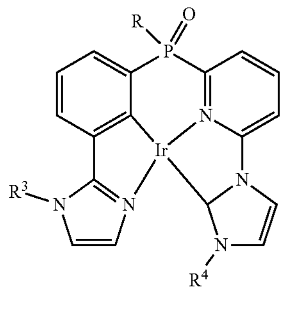
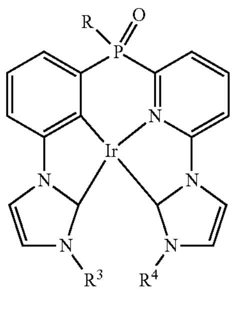

-continued

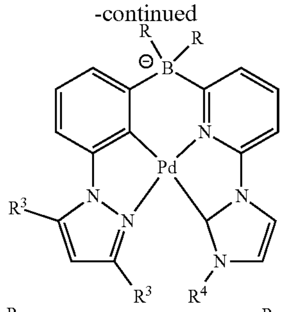

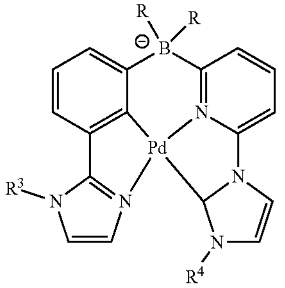

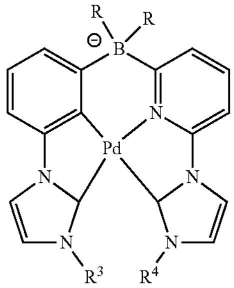

.

4. The compound of claim 1, wherein the compound has the following structure:

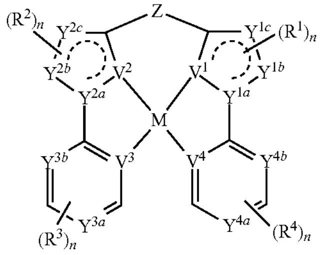

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{1c}$, $Y^{2a}$, $Y^{2b}$, $Y^{2c}$, $Y^{3a}$, $Y^{3b}$, $Y^{4a}$, $Y^{4b}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, substituted or unsubstituted aryl.

5. The compound of claim 1, wherein the compound has the following structure:

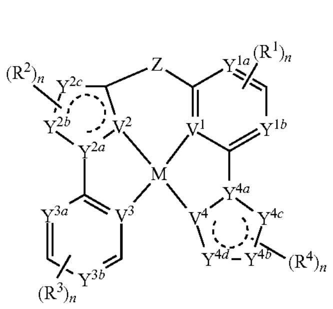

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$, $Y^{3a}$, $Y^{3b}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, thiol, or substituted or unsubstituted $C_1$-$C_4$ alkyl, alkoxy, or aryl, hydroxyl, amino, nitro, or thiol.

6. The compound of claim 5, wherein the compound has one of the following structures:

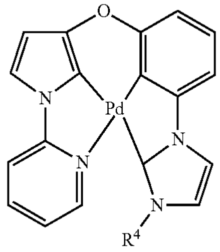

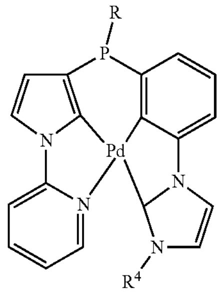

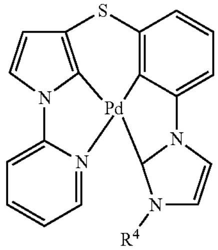

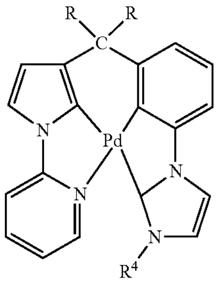

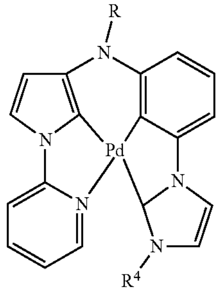

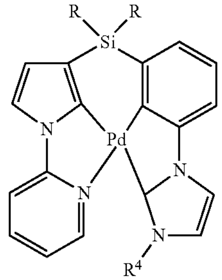

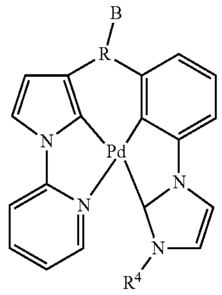

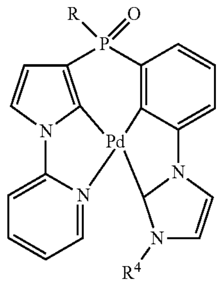

-continued

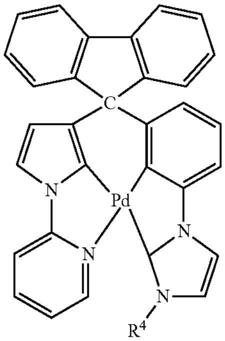

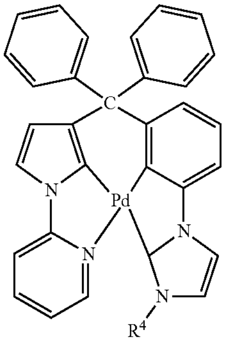

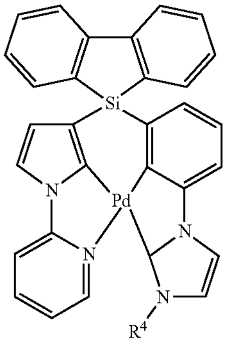

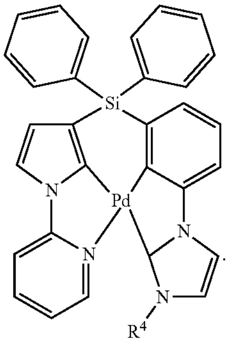

7. The compound of claim 1, wherein the compound has the following structure:

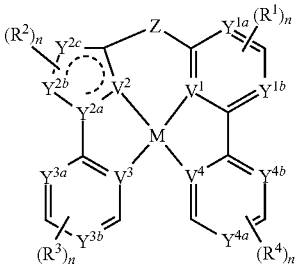

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{2c}$, $Y^{3a}$, $Y^{3b}$, $Y^{4a}$, $Y^{4b}$, is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

8. The compound of claim 1, wherein the compound has the following structure:

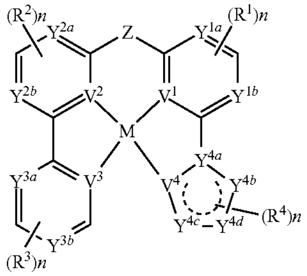

wherein:

each $R^1$, $R^2$, $R^3$, and $R^4$ represents a non-hydrogen substituent and is independently substituted or unsubstituted $C_1$-$C_4$ alkyl or substituted or unsubstituted aryl;

each n is independently an integer of 0 to 4, valency permitting; and each of $Y^{1a}$, $Y^{1b}$, $Y^{2a}$, $Y^{2b}$, $Y^{3a}$, $Y^{3b}$, $Y^{4a}$, $Y^{4b}$, $Y^{4c}$, and $Y^{4d}$ is independently N, $NR^{4a}$, or $CR^{4b}$, wherein each $R^{4a}$ and $R^{4b}$ is independently hydrogen, hydroxyl, amino, nitro, or thiol, or substituted or unsubstituted $C_1$-$C_4$ alkyl, alkoxy, or aryl.

9. The compound of claim 8, wherein the compound has one of the following structures:

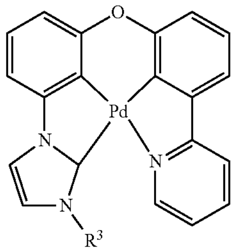

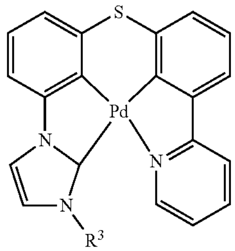

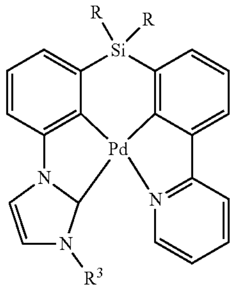

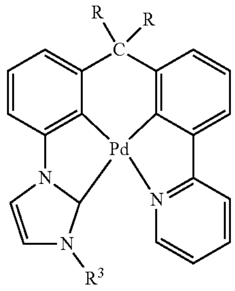

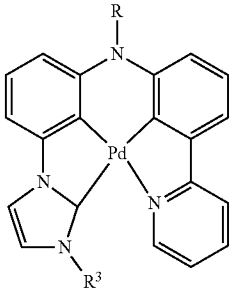

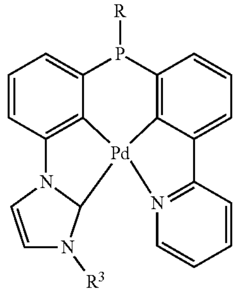

-continued
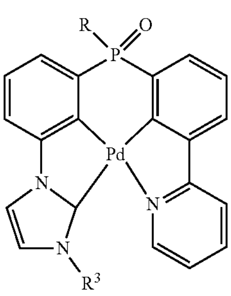
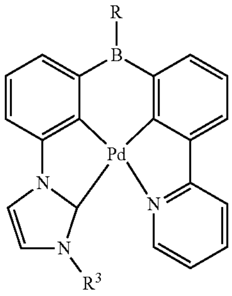
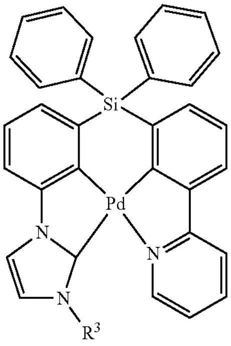
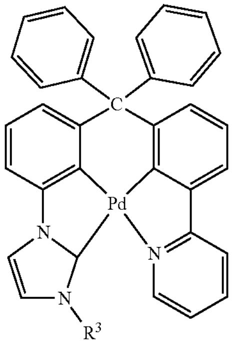
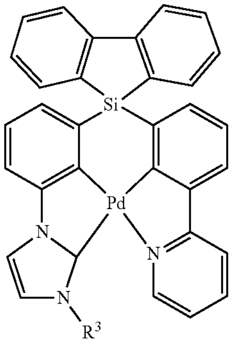
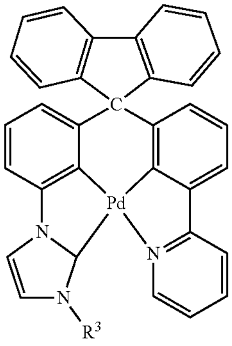
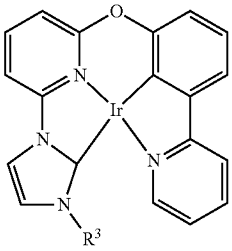
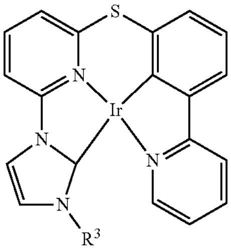
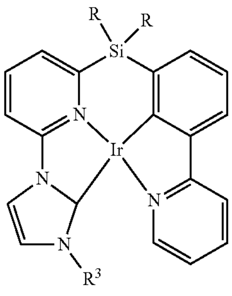
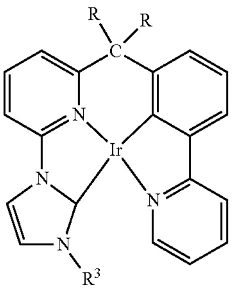
-continued
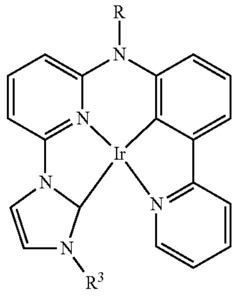
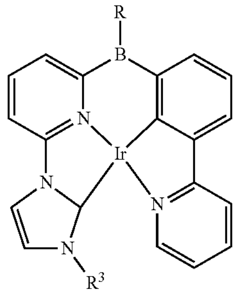
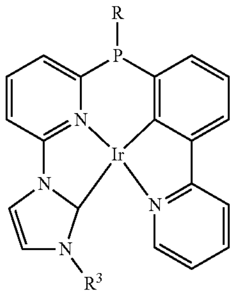
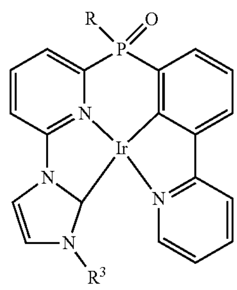
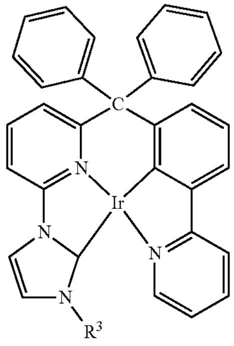
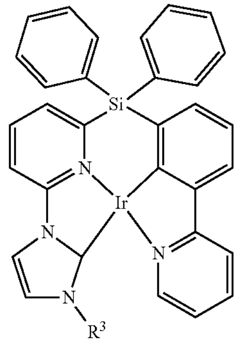
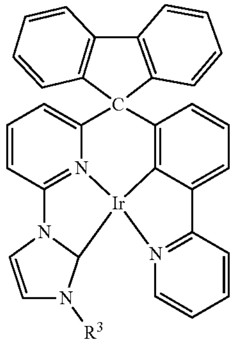
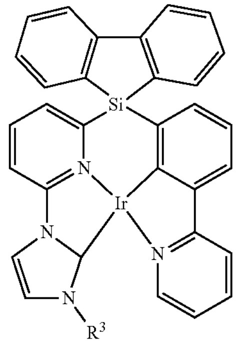
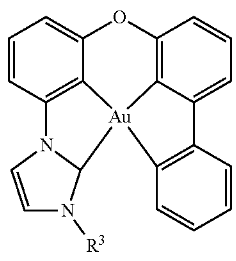
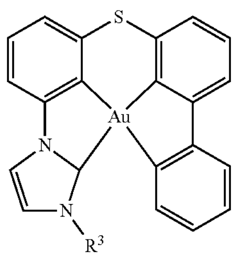

-continued
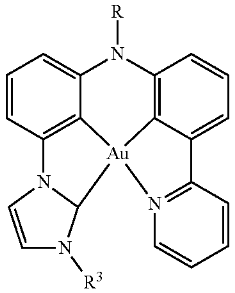
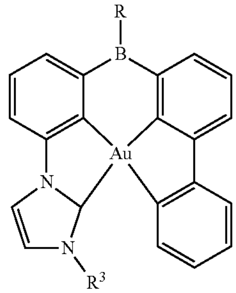
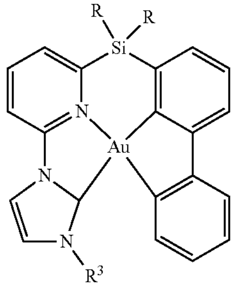
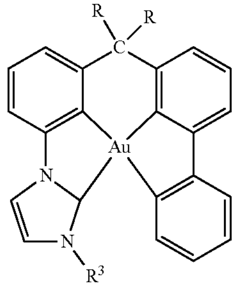
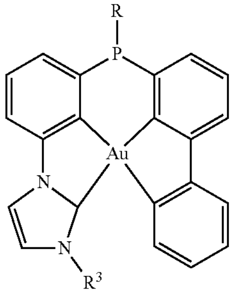
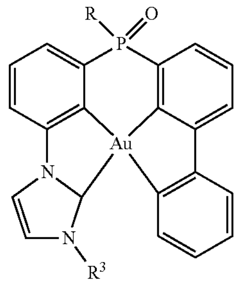
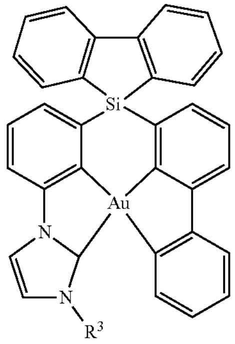
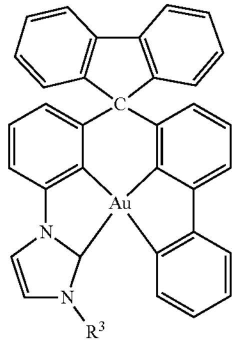
-continued
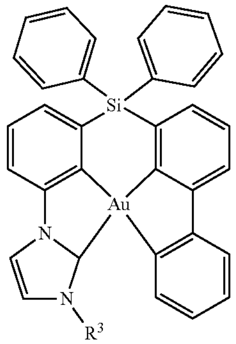
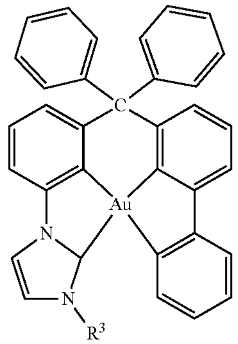
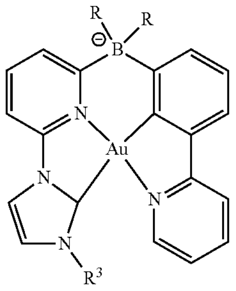
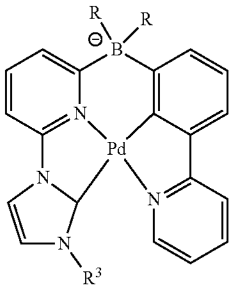
.
10. A light emitting device comprising the compound of claim 1.
11. An OLED device comprising the compound of claim 1.
12. The OLED device of claim 10, wherein the device is a phosphorescent OLED device.
13. A photovoltaic device comprising the compound of claim 1.
14. A luminescent display device comprising the compound of claim 1.
* * * * *